US008263772B2

(12) United States Patent
Arnold et al.

(10) Patent No.: US 8,263,772 B2
(45) Date of Patent: Sep. 11, 2012

(54) MCH RECEPTOR ANTAGONISTS

(75) Inventors: Macklin Brian Arnold, Morgantown, IN (US); Yen Dao, Indianapolis, IN (US); Kevin Matthew Gardinier, Fishers, IN (US); David Joseph Garmene, Indianapolis, IN (US); Steven James Green, Indianapolis, IN (US); Erik James Hembre, Indianapolis, IN (US); Jianliang Lu, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 610 days.

(21) Appl. No.: 12/298,792

(22) PCT Filed: Jun. 8, 2007

(86) PCT No.: PCT/US2007/070662
§ 371 (c)(1),
(2), (4) Date: Oct. 28, 2008

(87) PCT Pub. No.: WO2007/146758
PCT Pub. Date: Dec. 21, 2007

(65) Prior Publication Data
US 2009/0093456 A1 Apr. 9, 2009

Related U.S. Application Data

(60) Provisional application No. 60/811,841, filed on Jun. 8, 2006.

(51) Int. Cl.
*C07D 515/04* (2006.01)
*A61K 31/4365* (2006.01)
(52) U.S. Cl. ........................ 546/114; 514/301
(58) Field of Classification Search .................. 546/114; 514/301
See application file for complete search history.

(56) References Cited

U.S. PATENT DOCUMENTS 7,902,356 B2 * 3/2011 Amegadzie et al. ......... 544/105
2002/0099073 A1 * 7/2002 Andersen et al. ............ 514/301

FOREIGN PATENT DOCUMENTS

| WO | WO 03/033476 | | 4/2003 |
| WO | WO 03033476 A1 | * | 4/2003 |
| WO | WO 2005/047293 | | 5/2005 |
| WO | WO 2005042541 A1 | * | 5/2005 |
| WO | WO 2006066174 A1 | * | 6/2006 |
| WO | WO 2007/093364 | | 8/2007 |
| WO | WO 2007093366 A1 | * | 8/2007 |

OTHER PUBLICATIONS

Patani et. al. "Bioisosterism: A Rational Approach in Drug Design" Chemical Reviews 1996, 96, 3147-3176.*
Hertzog et. al. "The discovery and optimization of pyrimidinone-containing MCH R1 antagonists" Bioorganic & Medicinal Chemistry Letters Jul. 25, 2006, 16, 4723-4727.*
Dyck, et al., "A Thienopyridazinone-based Melanin-Concentrating Hormone Receptor 1 Antagonist with Potent in Vivo Anorectic Properties," *Journal of Medicinal Chemistry, American Chemical Society*, vol. 49, No. 13, pp. 3753-3756 (2006).

* cited by examiner

*Primary Examiner* — David K O Dell
(74) *Attorney, Agent, or Firm* — Elizabeth A. Dingess-Hammond

(57) ABSTRACT

The present invention relates to a melanin concentrating hormone antagonist compound of formula (1): wherein $R^1$, $R^a$, $R^b$, $R^2$, $L^1$, $R^3$, $R^4$ and $R^5$ are as defined, or a pharmaceutically acceptable salt, enantiomer, diastereomer or mixture of diasteromers thereof useful in the treatment, obesity and related diseases.

2 Claims, No Drawings

MCH RECEPTOR ANTAGONISTS

This application claims the benefit of U.S. Provisional Application Ser. No. 60/811,841, filed 8 Jun. 2006 and PCT Application Serial No. PCT/US2007/070662, filed 8 Jun. 2007, each hereby incorporated by reference in their entirety.

FIELD OF INVENTION

The present invention is in the field of medicine, particularly in the field of treating obesity and related diseases.

BACKGROUND OF THE INVENTION

Melanin concentrating hormone (MCH) is a 19 amino acid neuropeptide produced in the lateral hypothalamic area and zona incerta. Extensive evidence supports the orexigenic activity of MCH. MCHR1$^{-/-}$ mice have been reported to be lean and hyper metabolic, indicating that the R1 isoform mediates at least some of the metabolic effects of MCH.

PCT International publication WO 03/033476 A1 discloses pyrimidinones as melanin concentrating hormone receptor antagonists. PCT international publications WO2005/047293 A1 discloses compounds said to be useful as MCH antagonists. Dyck, B et al (*Journal of Medicinal Chemistry* (2006) 49(13) 3753-3756) entitled "*A Thienopyridazinone-Based Melanin-Concentrating Hormone Receptor 1 Antagonist with Potent In Vivo Anorectic Properties*" discloses thienopyridazinone compounds said to be useful as MCH antagonists.

There is a need for potent, selective and therapeutically effective agents to better control dietary habits, minimize the preponderance of obesity, treat, and/or ameliorate the effects of obesity and Related Diseases. The present invention provides particularly preferred compounds having high potency, selectivity and/or in-vivo efficacy as MCH antagonists useful for the treatment of obesity and related diseases.

SUMMARY OF INVENTION

The present invention relates to a compound of formula

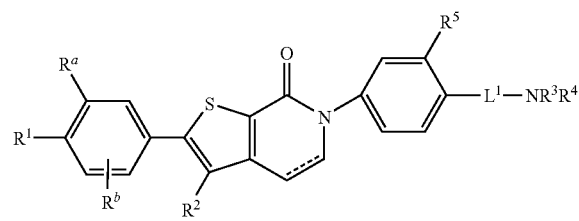

wherein:
"-----" is optionally a bond to form a double bond;
$R^1$ is independently selected from the group consisting of hydrogen, $C_1$-$C_4$ alkyl, halo, hydroxy, $C_1$-$C_4$ haloalkyl, $C_1$-$C_4$ alkoxy, $C_1$-$C_4$ haloalkoxy, —O—$C_3$-$C_4$ cycloalkyl, —$SO_2C_1$-$C_4$ alkyl, and —$NR^9R^{9'}$;
$R^a$ and $R^b$ are independently hydrogen, fluoro, chloro, or methoxy;
$R^2$ is hydrogen or $C_1$-$C_2$ alkyl;
$L^1$ is selected from the group consisting of a bond, —$OCH_2CH_2$—, —$OCH_2CH_2CH_2$—, —$CF_2CH_2CH_2$—, $CHFCH_2CH_2$—, —$CH(OH)CH_2CH_2$—, —$NHC(O)CH_2$—, $OCH_2CH$=$CH_2$, —$NHC(O)CH_2CH_2$, —$C(O)CH_2CH_2$—, —$C(O)NHCH_2CH_2$—, —$NH(CO)CH_2CH_2CH_2$—, and —$C(O)NHCH_2CH_2CH_2$;

$R^3$ and $R^4$ combine together with the nitrogen atom to which they are attached to form an optionally substituted 4 to 7-member nitrogen containing heterocyclic ring; or one of $R^3$ and $R^4$ combine with $L^1$ at a position α, β, γ, or, δ to the nitrogen of $NR^3R^4$ to form a 4 to 7-member nitrogen containing heterocyclic ring with $L^1$; wherein each 4 to 7-member nitrogen containing heterocyclic ring formed by the combination of $R^3$ and $R^4$ or $L^1$ and either of $R^3$ and $R^4$ is optionally substituted with one or two groups independently selected from oxo, hydroxy, —$OR^6$, halo, $C_1$-$C_4$ alkyl, —$C(O)C_1$-$C_4$ alkyl, $C_3$-$C_6$ cycloalkyl, and $NR^6R^{6'}$;
$R^5$ is hydrogen, chloro, fluoro, cyano, methyl, trifluoromethoxy, or methoxy;
$R^6$ and $R^{6'}$ are independently selected from the group consisting of hydrogen, and $C_1$-$C_4$ alkyl;
$R^9$ and $R^{9'}$ are independently selected from the group consisting of hydrogen, and $C_1$-$C_3$ alkyl;
or a pharmaceutically acceptable salt, or enantiomer, diastereomer or mixture of diastereomers thereof.

The present invention also relates to a pharmaceutical composition comprising a compound of formula I.

In another embodiment, the pharmaceutical composition of the present invention may be adapted for use in treating obesity and related diseases.

The present invention also relates to a method for treating obesity and related diseases comprising administering a therapeutically effective amount of a compound of the invention to a patient in need thereof.

The present invention relates to the use of a compound of formula 1 for the treatment of obesity and related diseases.

The present invention relates to the use of a compound of formula 1 as an appetite suppressant.

The present invention relates to the use of a compound of formula I for therapy.

The present invention is related to the use of a compound of the invention for the manufacture of a medicament for treating obesity and related diseases.

The present invention relates to a compound of formula:

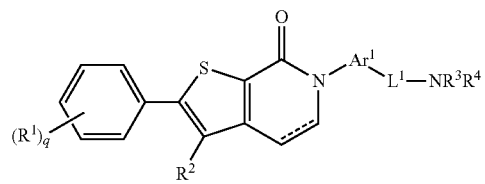

wherein:
"-----" is optionally a bond to form a double bond
q is 1 or 2;
$R^1$ is independently selected from the group consisting of hydrogen, $C_1$-$C_4$ alkyl, halo, hydroxy, $C_1$-$C_4$ haloalkyl, $C_1$-$C_4$ alkoxy, $C_1$-$C_4$ haloalkoxy, —O—$C_3$-$C_8$ cycloalkyl, amino, —$SO_2C_1$-$C_4$ alkyl, and $C_1$-$C_4$ alkyl$NR^6R^{6'}$;
$R^2$ is hydrogen or $C_1$-$C_4$ alkyl;
$Ar^1$ is phenyl optionally substituted with one or two groups independently selected from the group consisting of $C_1$-$C_4$ alkyl, —$OC_1$-$C_4$ alkyl, halo, $C_1$-$C_4$ haloalkyl, and —$OC_1$-$C_4$ haloalkyl;
$L^1$ is selected from the group consisting of a bond, —$OCH_2$—, —$OCHR^7CH_2$—, —$OCH_2CHR^7$—, —$OCHR^7CH_2CH_2$—, —$OCH_2CHR^7CH_2$—, $NR^7CH_2CH_2$, —$NR^7CH_2CH_2CH_2$, —$C(O)NR^7CHR^8$—, —$C(O)NR^7CH_2CHR^8$—, and —$C(O)NR^7CHR^8CH_2$;

$R^3$ and $R^4$ are independently selected from the group consisting of hydrogen, $C_1$-$C_4$ alkyl, or $R^3$ and $R^4$ combine together with the nitrogen atom to which they are attached to form an optionally substituted 5 to 7-member heterocyclic ring; or one of $R^3$ and $R^4$ combine with $L^1$ at a position α, β, γ, or, δ to the nitrogen of $NR^3R^4$ to form a nitrogen containing 5 to 7-member heterocyclic group with $L^1$ said heterocyclic group being optionally substituted with one to three substituent independently selected from oxo, hydroxy, —$OR^6$, $C_1$-$C_4$ alkyl, —$C(O)OC_1$-$C_4$ alkyl and CO—$C_4$ alkyl$NR^6R^{6'}$;

each $R^6$ and $R^{6'}$ is independently selected from the group consisting of hydrogen, $C_1$-$C_4$ alkyl, benzyl, $C_3$-$C_8$ cycloalkyl, and $C_4$-$C_8$ alkylcycloalkyl;

each $R^7$ is independently selected from the group consisting of hydrogen and $C_1$-$C_4$ alkyl or each $R^7$ combines with one or both of $R^3$ and $R^4$ to form a 5-7 member nitrogen containing heterocycle;

each $R^8$ is independently selected from the group consisting of hydrogen and $C_1$-$C_4$ alkyl or each $R^8$ combines with one or both of $R^3$ and $R^4$ to form a 5-7 member nitrogen containing heterocycle; or a pharmaceutically acceptable salt, or enantiomer, diastereomer or mixture of diastereomers thereof.

DETAILED DESCRIPTION

For the purposes of the present invention, as disclosed and/or claimed herein, the following terms and definitions apply unless otherwise stated.

General chemical terms used in the description of compounds herein described bear their usual meanings. For example, the term "$C_1$-$C_4$ alkyl" refers to a straight or branched aliphatic chain of 1 to 4 carbon atoms and isomers thereof including but not limited to methyl, ethyl, propyl, iso-propyl, n-butyl. Similarly, the term "$C_1$-$C_4$ alkyl" encompasses the terms $C_1$-$C_3$ alkyl, $C_1$-$C_2$ alkyl, $C_2$-$C_3$ alkyl, and $C_2$-$C_4$ alkyl each having the indicated number of carbon atoms.

The term "$C_3$-$C_6$ cycloalkyl" refers to a saturated carbocyclic ring having from 3 to 6 carbon atoms including cyclopropyl, cyclobutyl, cyclopentyl and cyclohexyl. Similarly, the term "$C_3$-$C_4$ cycloalkyl" refers to the group consisting of cyclopropyl, and cyclobutyl. The term $C_3$-$C_6$ haloalkyl encompasses the term $C_3$-$C_5$ haloalkyl, etc.

The term "halo" refers to a halogen, i.e., chloro, bromo, iodo and fluoro.

The term "$C_1$-$C_4$ haloalkyl" refers to a $C_1$-$C_4$ alkyl group substituted with one, two, three or more halogen atoms as indicated or chemically appropriate. Examples of $C_1$-$C_4$ haloalkyl include but are not limited to trifluoromethyl, chloroethyl, and 2-chloropropyl. Similarly, a "$C_2$-$C_3$ haloalkyl" is a methyl or ethyl group substituted with from one to the maximum applicable number of halogen atoms, preferably chloro or fluoro. One of skill in the art is aware that a $C_1$-$C_4$ haloalkyl encompasses a $C_1$-$C_3$ haloalkyl, and a $C_2$-$C_3$ haloalkyl.

A "$C_1$-$C_4$ alkoxy" group is a $C_1$-$C_4$ alkyl (or as indicated) moiety connected through an oxy linkage. Examples of alkoxy groups include but are not limited to methoxy (—OMe), ethoxy(—OEt), propoxy (—OPr), isopropoxy (—OiPr), butoxy (—OBu), etc. Similarly, the term "$C_1$-$C_3$ alkoxy" includes methoxy (—OMe), ethoxy(—OEt), propoxy (—OPr), isopropoxy (—OiPr). Likewise, $C_1$-$C_2$ alkoxy includes OMe and OEt groups.

The term "$C_1$-$C_4$ haloalkoxy" encompasses $C_1$-$C_4$ alkoxy wherein one or more of the hydrogen atoms on the alkyl portion have been replaced with halogens. Examples of haloalkoxy groups include difluoromethoxy, trifluoromethoxy, 2-haloethoxy, 2,2,2-trifluoroethoxy, 4,4,4-trifluorobutoxy, up to and including like groups having the indicated number of carbon atoms. For example, $C_1$-$C_2$ haloalkoxy includes $OCF_3$ and $OCH_2CH_2F$ groups and others having one or two carbon atoms and appropriate number of halogens.

The term "$C_1$-$C_3$ alkylalcohol" encompasses a monovalent radical alcohol including methanol, ethanol, propanol and isopropanol used as a terminal appendage to the group to which it is attached. Similar terms encompass alcohols having the indicated number of carbon atoms. For example, $C_1$-$C_2$ alkylalcohol includes methanol and ethanol.

The invention also contemplates that the term $C_1$-$C_4$ alkyl encompasses the specified alkyl which may result in chirality as appended. Such resulting chiral compounds are also objects of the present invention.

The terms "α", "β", "γ", or "δ" refer respectively to a position 1, 2, 3, or 4 atom-positions from the nitrogen of $NR^3R^4$ counting backward on formula I. The terms "α", "β", "γ", or "δ" designate the position on a compound of formula I where one of $R^3$ and $R^4$ forms a heterocyclic ring with an atom on the $L^1$ chain (linker $L^1$). One of skill in the art is aware that the combination of $R^3$ and $R^4$ or combination of $R^3$ or $R^4$ with $L^1$ to form a 4 to 7 member nitrogen containing heterocyclic ring, as disclosed and used herein requires an implied abstraction of one or two hydrogen atoms from a CH, or $CH_2$ group as necessary from one or both combining groups. Furthermore, as used herein, it is contemplated that when one of $R^3$ and $R^4$ combines with $L^1$ to form a (4 to 7 member) nitrogen containing heterocyclic ring the other of $R^3$ and $R^4$ is either a hydrogen atom or an optional substituent on said ring wherein optional substituents are as defined below or as indicated for the particular group of compounds of formula I.

The term "nitrogen containing heterocyclic" means a saturated, partially unsaturated, fully unsaturated, or aromatic 4, 5, 6 or 7 membered (or as otherwise specified) optionally having additional heteroatoms selected from nitrogen and oxygen. Representative heterocyclic groups include azetidinyl, morpholinyl, piperidinyl, piperazinyl, diazepanyl, and pyrrolidinyl. Thus as used herein the term 4 to 7 member nitrogen containing heterocyclic group encompasses separately and/or collectively 4 to 6, to 6, 5 to 7, and 4 to 7 member nitrogen containing heterocyclic groups.

The term "oxo" as used herein implies an oxygen atom attached to a carbon atom which is part of a ring or a chain to form a carbonyl group.

The present invention provides chemically stable compounds and one of skill in the art is aware of the particular combination of substituents within the scope defined and/or exemplified herein that leads to chemical stability including implied addition or subtraction of hydrogen atoms to achieve the described and/or intended chemically stable compound.

The term "suitable solvent" refers to any solvent, or mixture of solvents, inert to the ongoing reaction, that sufficiently solubilizes the reactants to afford a medium within which to effect the desired reaction.

As used herein, the term "patient" refers to humans, companion animals (e.g. dogs and cats and the like), and livestock animals.

The terms "treatment" "treat" and "treating" include ameliorating, halting, restraining, slowing, and reversing the progression of, or reducing the severity of pathological symptoms of obesity and related diseases.

As used herein, the term "therapeutically effective amount" means an amount of a compound of the present invention that is capable of treating the symptoms of the various pathological conditions herein described.

The term "pharmaceutically acceptable" is used herein as an adjective and means substantially non-deleterious to the recipient patient.

The terms "diseases related to obesity" or "related diseases" as used herein refer to symptoms, diseases or conditions caused by, exacerbated by, induced by, or adjunct to the condition of being obese. Such diseases, conditions and/or symptoms include but are not limited to eating disorders (bulimia, anorexia nervosa, etc.), diabetes, diabetic complications, diabetic retinopathy, depression, anxiety, hypertension, cerebral hemorrhage, congestive heart failure, atherosclerosis, rheumatoid arthritis, stroke, hyperlipidemia, hypertriglycemia, hyperglycemia, and hyperlipoproteinemia.

Pharmaceutically acceptable salts and methodologies for preparing them are well known to one of skill in the art. See, e.g. P. Stahl, et al. Handbook of Pharmaceutical Salts: Properties, Selections and Use (VCHA/Wiley-VCH, 200); S. M. Berge, et al., "Pharmaceutical Salts" Journal of Pharmaceutical Sciences, Vol. 66, No. 1, January 1977.

Preferred Compounds of the Invention

Certain compounds of the invention are particularly interesting and preferred. The following listing sets out several groups of preferred compounds. It will be understood that each of the listings may be combined with other listings or groupings described herein to create additional groups of preferred compounds within the scope of the invention as defined.

Preferred $R^1$ groups are independently selected from the group consisting of chloro, fluoro, methyl, trifluoromethyl, trifluoromethoxy, propoxy, —N(CH$_3$), —SO$_2$CH$_3$, and cyclopropoxy. More preferably, $R^1$ is selected from the group consisting of fluoro, chloro, cyclopropoxy, trifluoromethoxy, and methoxy. Most preferred $R^1$ is chloro or methoxy.

Preferably $R^a$ and $R^b$ are independently hydrogen, fluoro, or methoxy.

$R^2$ is preferably hydrogen.

Preferably $L^1$ is selected from the group consisting of a bond, —OCH$_2$CH$_2$—, —CF$_2$CH$_2$CH$_2$—, —CHFCH$_2$CH$_2$—, CH(OH)CH$_2$CH$_2$—, —OCH$_2$CH$_2$CH$_2$—, —OCH$_2$CH=CH$_2$—, —NHC(O)CH$_2$—, —NHC(O)CH$_2$CH$_2$—, —C(O)CH$_2$CH$_2$—, —C(O)NHCH$_2$CH$_2$—, and —C(O)NHCH$_2$CH$_2$CH$_2$.

Preferred are $R^3$ and $R^4$ groups which combine with each other and the nitrogen atom to which they are attached to form an optionally substituted 4 to 7 member nitrogen containing heterocyclic ring; or where one of $R^3$ and $R^4$ combine with $L^1$ at a position α, β, or γ to the nitrogen of NR$^3$R$^4$ to form an optionally substituted 4 to 7 member nitrogen containing heterocyclic ring selected from the group consisting of azetidinyl, morpholino, pyrrolidinyl, imidazolyl, piperazinyl, diazepanyl, and piperidinyl and wherein each 4 to 7-member nitrogen containing heterocyclic ring formed by $R^3$ and $R^4$ or the combination of $L^1$ and either of $R^3$ and $R^4$ is optionally substituted with one or two groups independently selected from methyl, oxo, hydroxy, halo, amino, N-methylamine and N,N-dimethylamine.

A preferred $R^5$ group is hydrogen, chloro, fluoro, trifluoromethoxy, methoxy or cyano. More preferably, $R^5$ is hydrogen, fluoro, chloro, or methoxy. Most preferably, $R^5$ is methoxy, chloro or fluoro.

A preferred $R^6$ or $R^{6'}$ is independently selected from hydrogen, and $C_1$-$C_2$ alkyl. More preferably, $R^6$ and $R^{6'}$ groups are independently selected from hydrogen, and methyl.

Preferably $R^9$ and $R^{9'}$ are independently selected from the group consisting of hydrogen and methyl.

A preferred compound of the invention is a compound of formula I wherein:

"-----" is optionally a bond to form a double bond
$R^1$ is independently selected from the group consisting of hydrogen, $C_1$-$C_3$ alkyl, halo, $C_1$-$C_3$ alkoxy, —OC$_3$-$C_4$ cycloalkyl, and $C_1$-$C_3$ haloalkyl;
$R^a$ and $R^b$ are independently hydrogen, or chloro;
$R^2$ is hydrogen;
$L^1$ is selected from the group consisting of a bond, —OCH$_2$CH$_2$—, —CF$_2$CH$_2$CH$_2$—, —CHFCH$_2$CH$_2$—, CH(OH)CH$_2$CH$_2$—, —OCH$_2$CH$_2$CH$_2$—, —OCH$_2$CH=CH$_2$—, —NHC(O)CH$_2$—, —NHC(O)CH$_2$CH$_2$—, —C(O)CH$_2$CH$_2$—, —C(O)NHCH$_2$CH$_2$—, and —C(O)NHCH$_2$CH$_2$CH$_2$;
$R^3$ and $R^4$ combine together and with the nitrogen atom to which they are attached form an optionally substituted 4 to 7 member nitrogen containing heterocyclic ring; or one of $R^3$ and $R^4$ combine with $L^1$ at a position α, β, γ, or, δ to the nitrogen of NR$^3$R$^4$ to form a 4 to 7 member nitrogen containing heterocyclic ring with $L^1$; wherein each 4 to 7-member nitrogen containing heterocyclic ring formed by the combination of $R^3$ and $R^4$ or $L^1$ and either of $R^3$ and $R^4$ is selected from the group consisting of azetidinyl, morpholino, pyrrolidinyl, imidazolyl, piperazinyl, and piperidinyl and each is optionally substituted with one or two groups independently selected from the group consisting of oxo, halo, hydroxy, —OR$^6$, —C$_1$-C$_4$ alkyl, —C(O)C$_1$-C$_4$ alkyl, and —NR$^6$R$^{6'}$;
$R^5$ is selected from the group consisting of —OMe, chloro, fluoro, and cyano;
$R^6$ and $R^{6'}$ are independently selected from the group consisting of hydrogen, and —C$_1$-C$_4$ alkyl; and
$R^9$ and $R^{9'}$ are independently hydrogen or methyl.

Also preferred is a compound of formula I wherein:
$R^1$ is methyl, chloro, methoxy, fluoro, trifluoromethyl, or cyclopropoxy;
$R^a$ and $R^b$ are independently hydrogen, chloro, fluoro, or methoxy;
$R^2$ is hydrogen;
$L^1$ is a bond;
$R^3$ and $R^4$ combine together and with the nitrogen atom to which they are attached form an optionally substituted 4 to 7 member nitrogen containing heterocyclic ring selected from the group consisting of pyrrolidinyl, morpholino, piperidinyl, piperazinyl, imidazolyl, and azetidinyl and each is optionally substituted with one or two groups independently selected from hydroxy, methyl, fluoro, —N-methylamine, N,N-dimethylamine, oxo, cyclopropyl and cyclobutyl;
$R^5$ is hydrogen, —OCH$_3$, cyano, fluoro, or chloro.

Also preferred is a compound of formula I wherein:
$R^1$ is methyl, chloro, methoxy, fluoro, trifluoromethyl, or cyclopropoxy;
$R^a$ and $R^b$ are independently hydrogen, fluoro, or methoxy;
$R^2$ is hydrogen;
$L^1$ is selected from the group consisting of a bond, —OCH$_2$CH$_2$—, —NHC(O)CH$_2$CH$_2$—, —NHC(O)CH$_2$—, —CH$_2$—CH=CH$_2$—, —C(O)CH$_2$CH$_2$—, and —C(O)NHCH$_2$CH$_2$—;
$R^3$ and $R^4$ combine together and with the nitrogen atom to which they are attached form an optionally substituted 4 to 7 member nitrogen containing heterocyclic ring; or one of $R^3$ and $R^4$ combine with $L^1$ at a position α, β, or γ to the nitrogen of NR$^3$R$^4$ to form a 4 to 7 member nitrogen containing heterocyclic ring with $L^1$; wherein each 4 to 7-member nitrogen containing heterocyclic ring formed by the combination of $R^3$ and $R^4$ or $L^1$ and either of $R^3$ and $R^4$ is selected from the group consisting of pyrrolidinyl, morpholino, piperidinyl, piperazinyl, imidazolyl, and azetidinyl and each is optionally substituted with one or two groups independently selected from hydroxy, methyl, fluoro, —N-methylamine, N,N-dimethylamine, oxo, cyclopropyl and cyclobutyl;
$R^5$ is hydrogen, —$OCH_3$, cyano, fluoro, or chloro.

Also preferred is a compound of formula I wherein:
$R^1$ is chloro, methoxy, or trifluoromethoxy;
$R^a$ and $R^b$ are both hydrogen;
$R^2$ is hydrogen;
$L^1$ is selected from the group consisting of —$CF_2CH_2CH_2$—, —$CHFCH_2CH_2$—, and —$CH(OH)CH_2CH_2$—;
$R^3$ and $R^4$ combine together and with the nitrogen atom to which they are attached form an optionally substituted 4 to 7 member nitrogen containing heterocyclic ring; or one of $R^3$ and $R^4$ combine with $L^1$ at a position α, β, or γ to the nitrogen of $NR^3R^4$ to form a 4 to 7 member nitrogen containing heterocyclic ring with $L^1$; wherein each 4 to 7-member nitrogen containing heterocyclic ring formed by the combination of $R^3$ and $R^4$ or $L^1$ and either of $R^3$ and $R^4$ is selected from the group consisting of pyrrolidinyl, piperidinyl, and piperazinyl wherein each 4 to 7 member nitrogen containing heterocyclic ring formed by the combination of $R^3$ and $R^4$ or $L^1$ and either of $R^3$ and $R^4$ is optionally substituted with one or two groups independently selected from methyl, fluoro, —N-methylamine, N,N-dimethylamine, and cyclobutyl;
$R^5$ is selected from the group consisting of hydrogen, methoxy, chloro, and fluoro.

Also preferred is a compound of formula I wherein:
$R^1$ is chloro, trifluoromethyl, or methoxy;
$R^a$ and $R^b$ are independently selected from hydrogen, fluoro, and chloro;
$R^2$ is hydrogen;
$L^1$ is a bond or —$OCH_2CH_2$—, —$OCH_2CH_2CH_2$—;
$R^3$ and $R^4$ combine together and with the nitrogen atom to which they are attached form a 4 to 7-member nitrogen containing heterocyclic ring selected from the group consisting of pyrrolidinyl, morpholino, piperidinyl, piperazinyl, imidazolyl, and azetidinyl wherein each 4 to 7 member nitrogen containing heterocyclic ring is optionally substituted with one or two groups selected from hydroxy, methyl, fluoro, —N-methylamine, N,N-dimethylamine, oxo, cyclopropyl and cyclobutyl;
$R^5$ is hydrogen, —$OCH_3$, cyano, fluoro, or chloro.

Also preferred is a compound of formula I wherein:
$R^1$ is chloro, methoxy, trifluoromethyl, or trifluoromethoxy;
$R^a$ and $R^b$ are both hydrogen;
$R^2$ is hydrogen;
$L^1$ is selected from the group consisting of —$NHC(O)CH_2$—, —$NHC(O)CH_2CH_2$—, —$NHC(O)CH_2CH_2$, —$C(O)CH_2CH_2$—, $C(O)NHCH_2CH_2$, and —$C(O)NHCH_2CH_2CH_2$—;
$R^3$ and $R^4$ combine together and with the nitrogen atom to which they are attached form an optionally substituted 4 to 7-member nitrogen containing heterocyclic ring; or one of $R^3$ and $R^4$ combine with $L^1$ at a position α, β, or γ to the nitrogen of $NR^3R^4$ to form a 4 to 7 member nitrogen containing heterocyclic ring with $L^1$; wherein each 4 to 7-member nitrogen containing heterocyclic ring formed by the combination of $R^3$ and $R^4$ or $L^1$ and either of $R^3$ and $R^4$ is selected from the group consisting of pyrrolidinyl, morpholino, piperidinyl, piperazinyl, imidazolyl, and azetidinyl and is optionally substituted with one or two groups independently selected from hydroxy, methyl, fluoro, —N-methylamine, N,N-dimethylamine, cyclobutyl, and oxo;
$R^5$ is selected from the group consisting of hydrogen, methoxy, cyano, and chloro.

Also preferred is a compound of formula I wherein:
$R^1$ is chloro, fluoro, methoxy, trifluoromethyl, or trifluoromethoxy;
$R^a$ and $R^b$ are both hydrogen;
$R^2$ is hydrogen;
$L^1$ is a bond;
$R^3$ and $R^4$ combine to form a 4 to 7 member nitrogen containing heterocyclic ring selected from the group consisting of pyrrolidinyl, piperidinyl, diazepanyl, and morpholino and wherein each 4 to 7 member nitrogen containing heterocyclic ring is optionally substituted with a group selected from the group consisting of —OH, —$NHCH_3$, —$N(CH_3)_2$, —$CH_3$, cyclobutyl, and fluoro; and
$R^5$ is hydrogen, methyl, methoxy, cyano or chloro.

Also preferred is a compound of formula I wherein:
$R^1$ is chloro, fluoro, methoxy, trifluoromethyl or trifluoromethoxy;
$R^a$ and $R^b$ are both hydrogen;
$R^2$ is hydrogen;
$L^1$ is —$OCH_2CH_2$—, —$OCH_2CH_2CH_2$—;
$R^3$ and $R^4$ combine to form a 4 to 7 member nitrogen containing heterocyclic ring selected from the group consisting of pyrrolidinyl, piperidinyl, diazepanyl, and morpholino and wherein each 4 to 7 member nitrogen containing heterocyclic ring is optionally substituted with a group selected from the group consisting of —OH, —$NHCH_3$, —$N(CH_3)_2$, —$CH_3$, cyclobutyl, and fluoro; and
$R^5$ is hydrogen, methyl, methoxy or cyano.

Also preferred is a compound of formula I wherein:
$R^1$ is chloro, fluoro, methoxy, trifluoromethyl or trifluoromethoxy:
$R^a$ and $R^b$ are independently selected from hydrogen, fluoro, and chloro;
$R^2$ is hydrogen;
$L^1$ is selected from the group consisting of a —$NHC(O)CH_2$—, —$NHC(O)CH_2CH_2$—$C(O)NHCH_2CH_2$—, $NHC(O)CH_2CH_2CH_2$, and —$C(O)NHCH_2CH_2CH_2$—;
$R^3$ and $R^4$ combine together and with the nitrogen atom to which they are attached form an optionally substituted 4 to 7-member nitrogen containing heterocyclic ring; or one of $R^3$ and $R^4$ combine with $L^1$ at a position α, β, or γ to the nitrogen of $NR^3R^4$ to form a 4 to 7 member nitrogen containing heterocyclic ring with $L^1$; wherein each 4 to 7-member nitrogen containing heterocyclic ring formed by the combination of $R^3$ and $R^4$ or $L^1$ and either of $R^3$ and $R^4$ is selected from the group consisting of pyrrolidinyl, piperidinyl, and morpholino and wherein each 4 to 7 member nitrogen containing heterocyclic ring formed by the combination of $R^3$ and $R^4$ or $L^1$ and either of $R^3$ and $R^4$ is optionally substituted with a group selected from the group consisting of —OH, —$NHCH_3$, —$N(CH_3)_2$, —$CH_3$, cyclobutyl, and fluoro; and
$R^5$ is hydrogen, chloro, fluoro, or methoxy.

Preparing Compounds of the Invention

The compounds of the invention (i.e. formula I) can be prepared by a variety of procedures known in the art and those described below. The products of each step in the schemes below can be recovered by conventional methods including extraction, evaporation, precipitation, chromatography, filtration, triturating, crystallization, and the like. In the schemes below all substituents, unless otherwise indicated, are as previously defined and suitable reagents are well known and appreciated in the art.

Scheme 1

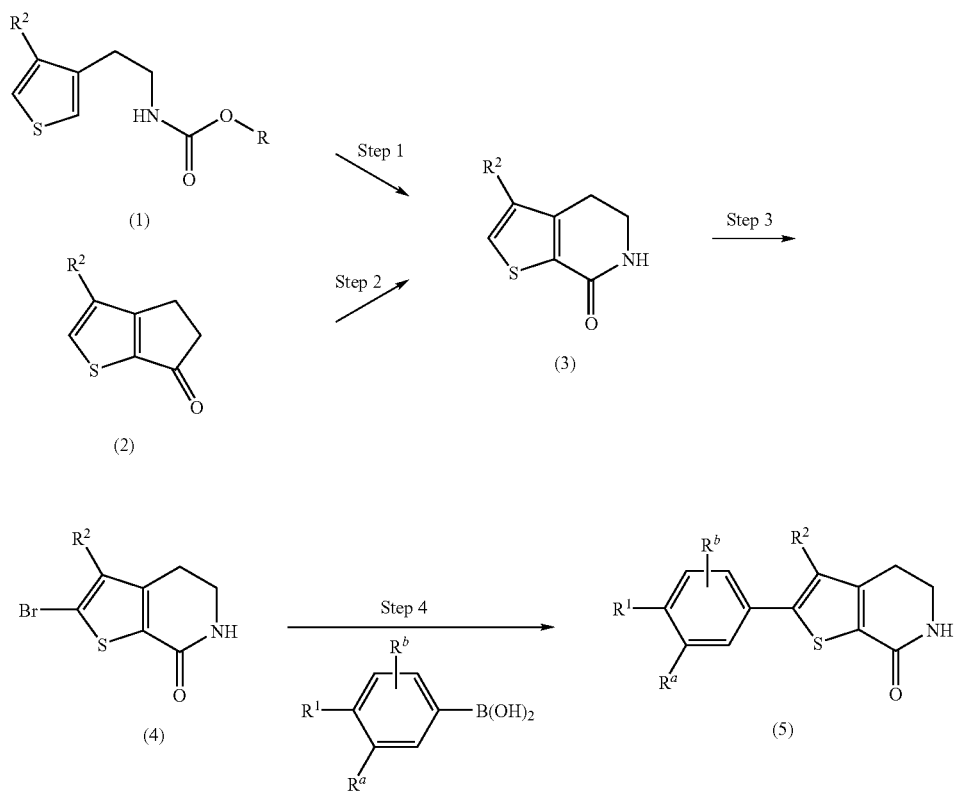

Formation of an intermediate of formula (5) can be carried out in accordance with reactions as depicted in Scheme 1.

In Scheme 1, Step 1, a carbamate of formula (I) is converted to a lactam of formula (3) using a Friedel-Crafts acylation. For example, carbamate (1) is dissolved in excess phosphorous oxychloride and treated with phosphorous pentoxide at about 100-130° C.

Alternatively, in Step 2, the lactam of formula (3) can be obtained by ring expansion of a ketone of formula (2) by treating with hydroxylamine and excess sodium acetate in an alcohol solvent such as MeOH or EtOH. The intermediate imine is isolated by filtration and treated with a strong acid, such as polyphosphoric acid at about 100-150° C. to provide the lactam (3).

The bromination of the thiophene ring to provide bromo-thiophene (4) is achieved by treatment with bromine, in a suitable solvent such as acetic acid, water, or carbon tetrachloride.

The bromo-thiophene of formula (4) is functionalized in Step 4 to an aryl thiophene of formula (5) by using a suitable metal-catalyzed cross-coupling reaction well known to those skilled in the art. For example, the bromo-thiophene (4) is treated with an aryl boronic acid in a solvent such as acetonitrile, DMF, toluene, water, etc. Included in the arylation reaction is a base such as potassium carbonate and a palladium catalyst such as Pd(OAc)$_2$, Pd(PPh$_3$)$_4$, or Pd(PPh$_3$)$_2$Cl$_2$, etc., typically with the addition of a phosphine ligand, such as PPh$_3$.

As will be appreciated, compounds of formula (1) and (2) can be readily prepared by methods similar to those described herein using procedures that are well-known and appreciated in the art. For example, compounds of formula (1) are prepared by reduction of a thiophene-3-acetonitrile to the amine and subsequent reaction with ethyl chloroformate. The ketone of formula (2) is readily prepared according to Aparajithan, K., et. al. *J. Heterocyclic Chem.* 1966, 3, 466.

Scheme 2

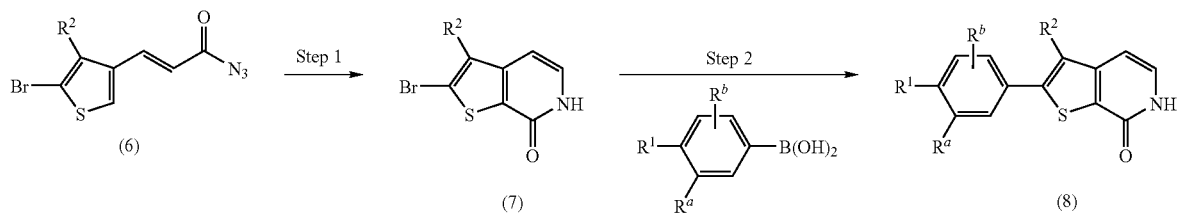

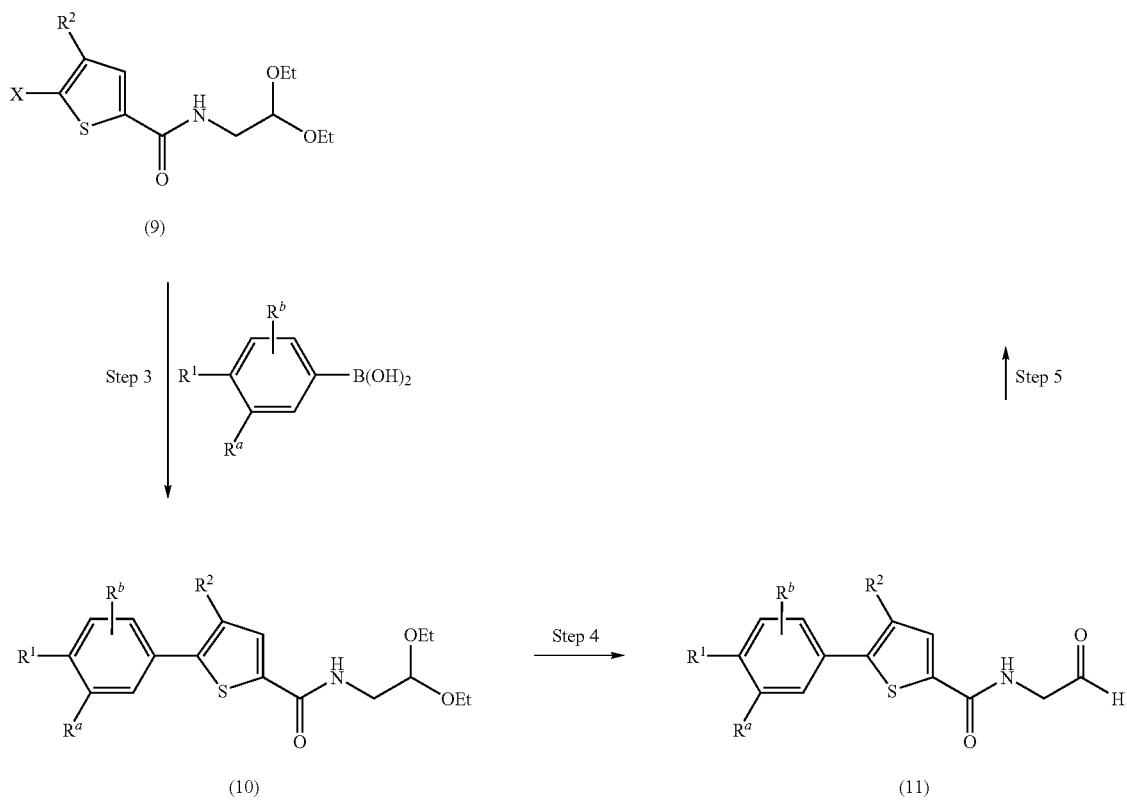

Formation of compounds of formula (8) can be carried out in accordance with methods depicted in Scheme 2. An appropriate compound of formula (9) is one in which X=Cl or Br and $R^2$ is as defined for formula (I). An appropriate compound of formula (8) is one in which $R^1$, $R^a$, $R^b$, and $R^2$ are as defined for formula (1).

In Scheme 2, Step 1, an acyl azide of formula (6) is cyclized under thermal conditions to a thienopyridinone of formula (7). For example, the acyl azide (6) is dissolved in dioxane and added dropwise to a preheated flask (230° C.) containing Dowtherm A®. The bromo-thienopyridinone of formula (7) is functionalized to an aryl-thienopyridinone using a metal-catalyzed cross-coupling reaction as described for Scheme 1, Step 4, above.

In Scheme 2, compounds of formula (8) can also be obtained by methods depicted in Steps 3, 4, and 5. In Step 3, a 5-halothiophene of formula (9) is converted to an aryl-thiophene of formula (10) using a metal catalyzed cross coupling reaction with an arylboronic acid. For example, a 5-halothiophene of formula (9), wherein X=Cl is dissolved in a solvent such as ethanol and treated with an arylboronic acid in the presence of a base such as sodium, potassium, or cesium carbonate. A palladium catalyst is added such as [1,3-bis(2,6-diisopropylphenyl)imidazol-2-ylidene)(3-chloropyridyl)] palladium (II) dichloride and the reaction carried out at a temperature range of about room temperature to about the reflux temperature of the chosen solvent.

In Step 4, an acetal of formula (10) is converted to an aldehyde of formula (11) using acidic conditions commonly known in the art. The preferred conditions use trifluoroacetic acid.

In Scheme 2, Step 5, an aldehyde of formula (11) is cyclized in an intramolecular condensation to afford a thienopyridinone of formula (8) under acidic conditions. The preferred conditions use trifluoromethane sulfonic acid as solvent at a temperature range of about 50 to 150° C. for about 1 to 5 h. The product is isolated by pouring the reaction onto cold water followed by filtration.

As will be readily appreciated compounds of formula (6) and (9) can be prepared by methods and procedures that are described herein or that are known in the art. For example, compounds of formula (6) are prepared by conversion of the corresponding acid (Gronowitz, S.; Ander, I. *Chemica Scripta* 1980, 15, 145) to the acid chloride and subsequent reaction with sodium azide to obtain the acyl azide of formula (6). Compounds of formula (9) are prepared by acylation of a 5-halothiophene-2-carboxylic acid with 2,2-diethoxyethylamine.

Scheme 3

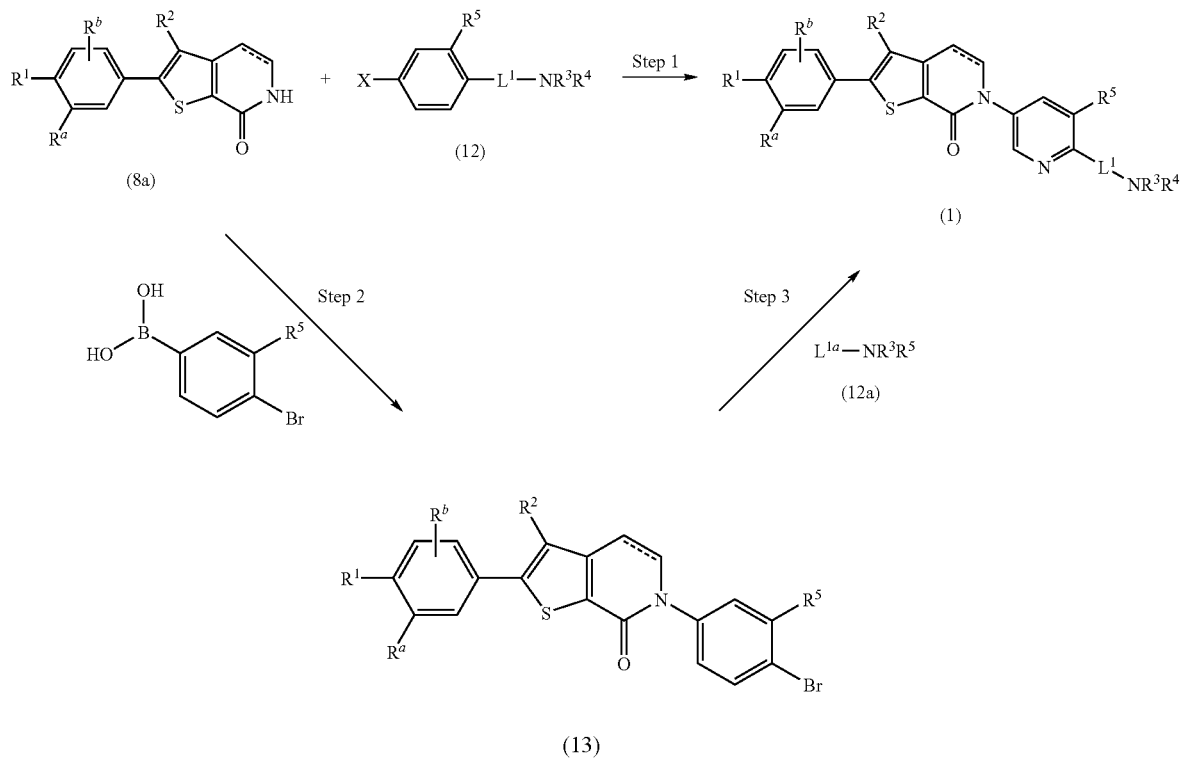

Formation of compounds of formula (I) can be carried out in accordance with methods depicted in Scheme 3. An appropriate compound of formula (8a) is one in which $R^1$, $R^a$, $R^b$, and $R^2$ are as defined for formula (I) and an appropriate compound of formula (12) is one in which $L^1$, $R^3$, $R^4$ and $R^5$ are as defined for formula (I) and X is bromide or iodide. A compound of formula (12a) is one in which $L^{1a}$ is defined as instances of $L^1$ wherein $L^1$ is a bond or $L^1$ contains an appropriate terminal primary or secondary amine, alcohol, or primary amide ($H_2NC(O)$—) to undergo the coupling reaction.

For example, in Step 1, a compound of formula (8a) is reacted with a compound of formula (12) using catalytic cross-coupling conditions, such as Buchwald arylation of an amide (Yin, J.; Buchwald, S. J. *J. Am. Chem. Soc.* 2002, 124(21), 6043-6048). The coupling reaction uses a base, for example $Cs_2CO_3$, a palladium reagent, for example $Pd_2dba_3$, and a phosphine ligand, for example Xantphos, in a non-protic solvent such as dioxane, toluene, or benzene. The reaction is generally carried out at a temperature range of about RT to about the reflux temperature of the chosen solvent.

Alternatively, the reaction is performed using copper-mediated conditions. For example, a compound of formula (8a) is dissolved in toluene or dioxane and treated with a compound of formula (12) (1 eq), $K_2CO_3$ (2 eq), N,N'-dimethyl-ethane-1,2-diamine (0.2 eq), and CuI (0.1 to 0.25 eq). The reaction is stirred at a temperature between about 80-110° C.

In Scheme 3, compounds of formula (I) can also be obtained by methods depicted in Steps 2 and 3. In Step 2, a lactam or pyridinone of formula (8a) is converted to a bromophenyl amide of formula (13) by coupling with a 4-bromophenylboronic acid. Preferred conditions use copper acetate, in the presence of 4A molecular sieves in an inert solvent, such as dichloromethane at about room temperature to the refluxing temperature of the solvent.

In Step 3, a bromophenylamide of formula (13) is elaborated to compounds of formula (I) by a copper or palladium mediated cross-coupling reaction with a secondary or primary amine, an alcohol, or a primary amide ($H_2NC(O)$—) contained within $L^{1a}$ using methods that are well known in the art. For example, a primary amide is reacted with a compound of formula (13) in the presence of copper iodide and cesium carbonate in an inert solvent such as dioxane at a temperature of about 80° C. to the reflux temperature of the solvent.

As will be recognized by the skilled artisan, compounds of formula (12) or (12a) can be readily prepared using procedures that are well-known and established in the art. For example, compounds of formula (12) are prepared by alkylation of a phenol with an alkyl halide or Mitsunobu reaction of a phenol with an alcohol. An amide linkage is prepared by acylation of a benzoic acid with an alkyl amine. The benzoic acid is obtained by conversion of the phenol to a triflate followed by carbonylation. It will be appreciated that the nature and sequence of reactions depends on the nature of $L^1$. Also, it is recognized that the steps required to prepare a compound of formula (12) can be carried out in any order, including after reaction of a partial compound of formula (12) with a compound of formula (I), such that the later carried out carbonylations, alkylations, acylations, arylations, etc., provide a compound of formula (I).

Scheme 4

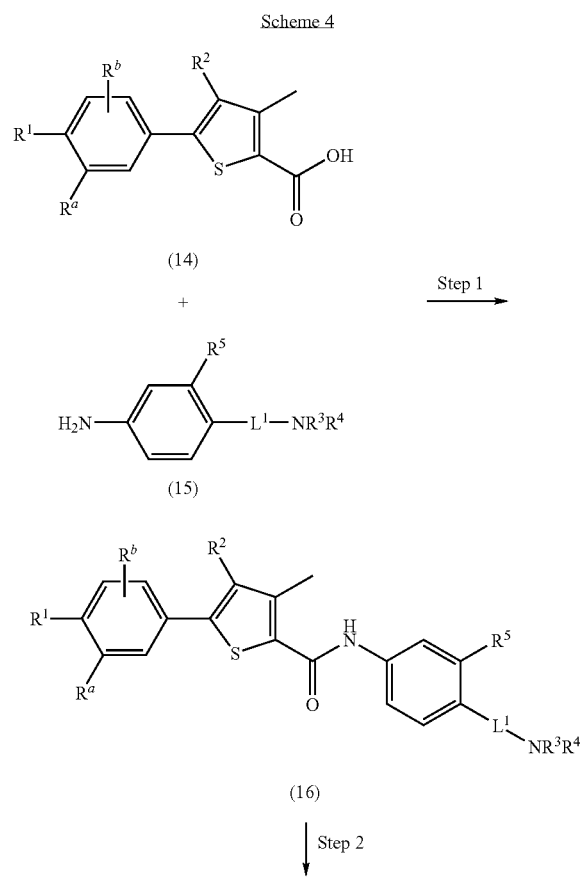

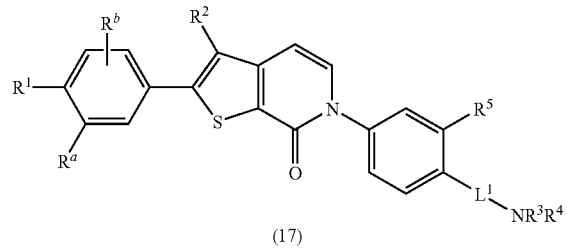

Formation of compounds of formula (17) can be carried out in accordance with methods depicted in Scheme 4.

In Scheme 4, Step 1, a methyl-thiophene carboxylic acid of formula (14) is acylated with an aniline of formula (15) to provide a methylthiophenylamide of formula (16). Acylating conditions are well known in the art. The preferred conditions use oxalyl chloride to form the acyl chloride followed by reaction with the aniline.

A methylthiophenylamide of formula (16) is treated with about 2.0 to 2.3 eq of a strong base, such as n-BuLi, t-BuLi, or LDA, at a temperature of about –70° C. or below. The solution is then treated with DMF and gradually warmed to room temperature and stirred for about 0.5-2 h to afford the thienopyridinone of formula (17).

As will be recognized by the skilled artisan, compounds of formula (14) and (15) can be readily prepared using procedures known in the art. For example, beginning with 2-bromo-4-methyl-thiophene and coupling with an aryl boronic acid, followed by carboxylation provides an carboxylic acid of formula (14). Compounds of formula (15) are prepared by nucleophilic aromatic displacement of a p-halo-nitrobenzene, such as a p-chloro or p-fluoronitro benzene, with an alcohol or amine. Subsequent reduction of the nitro group provides an aniline of formula (15). It will be readily apparent that it is possible to do the acylation with only a partial structure of formula (15), for example with an aniline containing a silyl-protected hydroxyl group which is subsequently deprotected and elaborated to compounds of formula (17).

Scheme 5

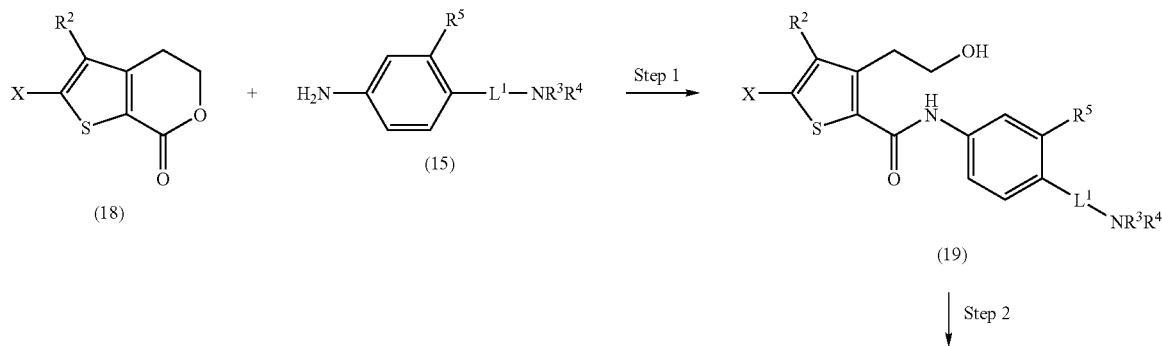

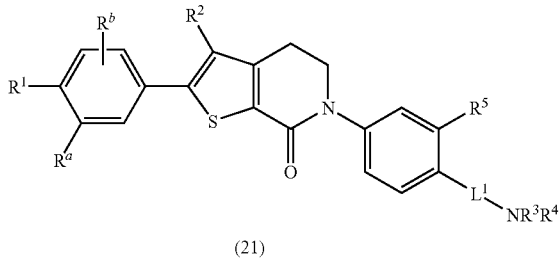

(21)

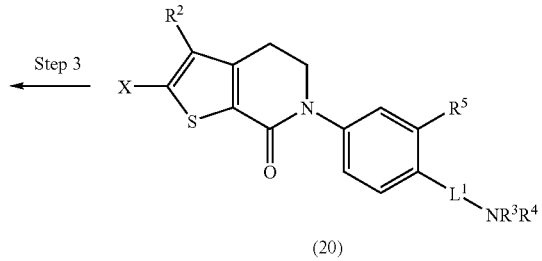

(20)

Formation of thiophenyl-lactams of formula (21) can be carried out in accordance with methods depicted in Scheme 5. An appropriate compound of formula (18) is one in which $R^2$ is as defined for formula (1), and X is Br or I.

In Scheme 5, Step 1, a thiophene lactone of formula (18) is converted to an amide of formula (19) using a typical Weinreb protocol (Basha, Anwer; Lipton, M.; Weinreb, Steven M. *Tetrahedron Letters*, 1977, 48, 4171). For example, an amine of formula (15) is dissolved in an aprotic solvent such as $CH_2Cl_2$ or toluene, and treated with a 2-2.5M solution of $Me_3Al$ in hexanes. The resulting solution is stirred at a temperature from about 0° C. to room temperature for about 5 to 60 min and then treated with a lactone of formula (18). The resulting solution is stirred at a range of between about room temperature and 110° C. for about 3 to 24 hours to provide the amide (19).

In Scheme 5, Step 2, the cyclization reaction to form the lactam of formula (20) can be carried out by at least two variants as discussed below.

In the first variant, the alcohol of formula (19) is converted to a leaving group, preferably mesylate, by reaction with methanesulfonyl chloride in the presence of a suitable base, like triethylamine. The intermediate mesylate is isolated by aqueous work-up and immediately dissolved in a polar anhydrous solvent such as DMF and treated with a base such as sodium hydride (1.5 eq) from about 0-25° C.

In a second variant, Mitsunobu conditions (Maligres, P. E.; et. al. *J. Het. Chem.* 2003, 40(2), 229-241) can also be employed. For example, the alcohol of formula (19) is dissolved in a suitable anhydrous solvent like THF, $CH_2Cl_2$, or toluene, and treated with a trialkyl- or triarylphosphine such as $Me_3P$, $Bu_3P$, or $Ph_3P$ and a dialkylazo-dicarboxylate, such as DEAD or DIAD, at a temperature of about 0° C. to room temperature.

In Scheme 5, Step 3, the lactam of formula (20) is further functionalized using a metal-catalyzed cross-coupling reaction as described for Scheme 1, Step 4.

As will be appreciated compounds of formula (18) can be readily prepared by methods similar to those described herein using procedures that are well-known and established in the art. For example, a 2-thiophen-3-yl-ethanol can be converted to the chloroformate using triphosgene, followed by cyclization to the lactone (thiophene lactone) using a Lewis acid, such as $AlCl_3$. The thiophene lactone is then halogenated, for example, by treatment with iodine and bis(trifluoroacetoxy) iodobenzene to afford a compound of formula (18). Halogenation of the thiophene lactone to afford compound (18) results in a mixture of 2- and 3-halogeno-thiophene latones. The desired 2-halogeno thiophene lactone fraction (18, $R^2$=H) may be isolated by chromatography (confirmable by $H^1NMR$). Compounds of formula (18) wherein $R^2$ is $C_1$-$C_4$ alkyl may be prepared by use of the 3-halogeno thiophene lactone fraction from above. The 3-halogenothiophene lactone is alkylated with an appropriately substituted alkyl substrate using a coupling method such as for example, Suzuki coupling (with alkyl boronic acid) to afford the 3-alkylthiophene lactone. The 3-alkylthiophene lactone is then halogenated to afford the desired compound of formula (18) wherein $R^2$ is $C_1$-$C_4$ alkyl.

Scheme 6

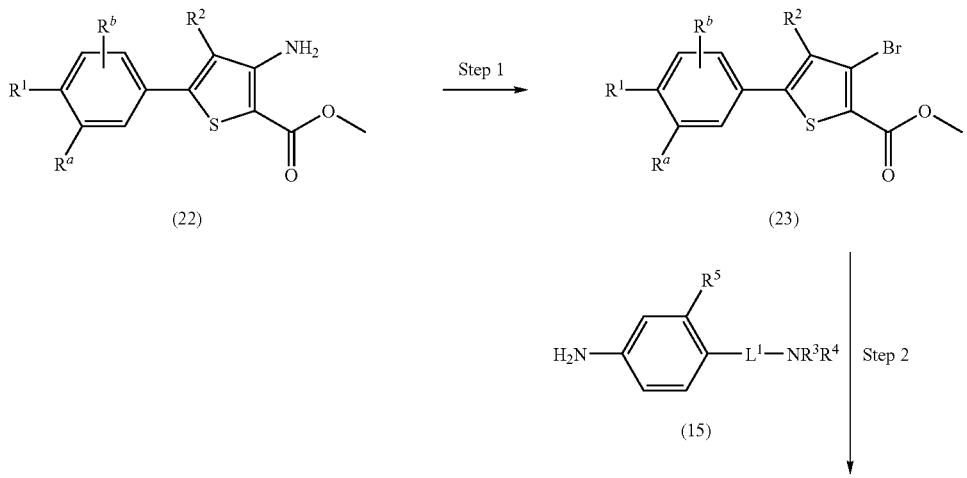

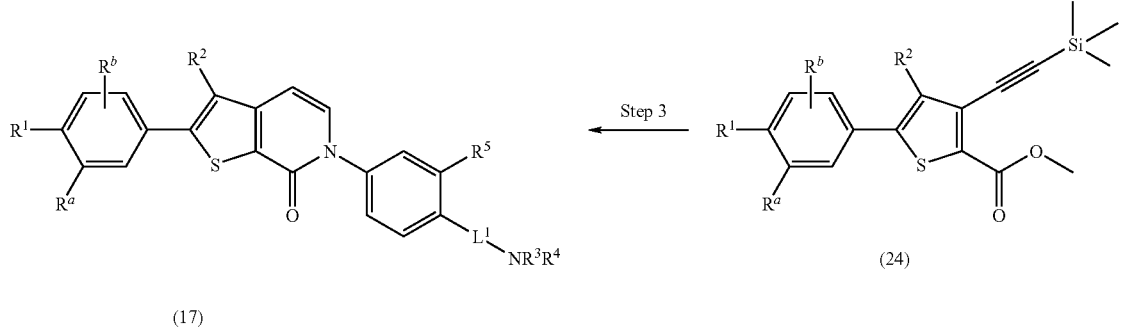

(17)        (24)

Formation of compounds of formula (17) can be carried out in accordance with methods depicted in Scheme 6. An appropriate compound of formula (22), (15), and (17) is one in which all variables are as defined in formula (1).

In Scheme 6, Step 1, an aminothiophene of formula (22) is converted to a bromothiophene of formula (23) using a Sandmeyer-like reaction. Preferred conditions use $CuBr_2$ and tert-butyl nitrite in the presence of an inert solvent, such as acetonitrile, from about room temperature to the reflux temperature of the solvent.

In Step 2, a bromothiophene of formula (23) is reacted with (trimethylsilyl)acetylene in a palladium mediated cross-coupling reaction to afford an ethynylthiophene of formula (24). For example, the bromo-thiophene (23) is treated with (trimethylsilyl)acetylene in an inert solvent, for example, acetonitrile, DMF, or toluene with addition of a base, such as diisopropylamine and a palladium catalyst such as $Pd(OAc)_2$, $Pd(PPh_3)_4$, or $Pd(PPh_3)_2Cl_2$, etc., typically with the addition of a phosphine ligand, such as $PPh_3$. Preferred conditions use DMF and $Pd(PPh_3)_2Cl_2$ with the addition of CuI at a temperature of about 50 to 150° C. Most preferred is to run the reaction in a microwave reactor for about 30 min.

In Scheme 6, Step 3, an ethynylthiophene of formula (24) is reacted with an aniline of formula (15) to afford an amide and subsequently cyclized in situ to afford a thienopyridinone of formula (17). Typical conditions use the Weinreb protocol as described for Scheme 5, Step 1, using $Me_3Al$ in an inert solvent such as toluene.

As will be readily understood, the steps to prepare the compounds of formula (1), (17) and (21), as depicted in the previous schemes, are dependent upon the particular compound being synthesized, the starting compound, and the relative lability of the substituted moieties. Also contemplated are various protection and deprotection steps as may be required or beneficial for carrying out the reactions above. For example, intermediates of formula (12) and (15) need not be fully elaborated prior to the various coupling or acylation steps described herein. Such intermediates may also have protected amine or hydroxyl functionality that is subsequently deprotected and further reacted to obtain compounds of the invention. The selection and use of suitable protecting groups is well known and appreciated in the art (see for example, *Protecting Groups in Organic Synthesis*, Theodora Greene (Wiley-Interscience)).

Demonstration of Function

All ligands, radioligands, solvents and reagents useful in these assays are readily available from commercial sources or can be readily prepared by those skilled in the art.

The full-length cDNA for human MCHR1 is cloned from a human adult brain cDNA library (Edge Biosystems, Cat. 38356) by standard polymerase chain reaction (PCR) methodology employing the following primers: sense, 5'-GC-CACCATGGACCT GGAAGCCTCGCTGC-3'; anti-sense, 5'-TGGTGCCCTGACTTGGAGGTGTGC-3'. The PCR reaction is performed in a final volume of 50 µL containing 5 µL of a 10× stock solution of PCR buffer, 1 µL of 10 mM dNTP mixture (200 µM final), 2 µl of 50 mM $Mg(SO_4)$ (2 mM final), 0.5 µL of 20 µM solutions of each primer (0.2 µM final), 5 µL of template cDNA containing 0.5 ng DNA, 0.5 µL of Platinum Taq High Fidelity DNA polymerase (Gibco Life Technologies) and 36 µL of $H_2O$. PCR amplification is performed on a Perkin Elmer 9600 thermocycler. Perform denaturation for 90 sec at 94° C., and repeat an amplification sequence consisting of 94° C. for 25 sec, 55° C. for 25 sec and 72° C. for 2 min 30 times, followed by a final elongation step at 72° C. for 10 min. The desired PCR product (1.1 Kb) is confirmed by agarose gel electrophoresis and the band is extracted from the gel by Geneclean (Bio101) following the manufacturer's instructions. Following extraction, clone the cDNA fragment was into pCR2.1-TOPO plasmid (Invitrogen Corp) to confirm the identity and sequence.

In order to generate cell lines stably expressing MCHR1, subclone the insert into the Xba I and Not I sites of pcDNA (+)-3.1-neomycin (Invitrogen). Purify by Qiagen Maxi-prep kit (QIAGEN, Inc.), transfect the plasmid by Fugene 6 (Roche Applied Science) into AV12 cells that has been previously transfected with the promiscuous G protein $G_{\alpha15}$. The transfected cells are selected by G418 (800 µg/mL) for 10-14 days and single colonies are isolated from culture plates. The G418-resistant colonies are further selected for MCHR1 expression by measuring MCH-stimulated $Ca^{2+}$ transients with a fluorometric imaging plate reader (FLIPR, Molecular Devices).

Typically, individual clones are plated out in 96-well plates at 60,000 cells per well in 100 µL of growth medium (Dulbecco's modified Eagle's medium (DMEM), 5% fetal bovine serum, 2 mM L-glutamine, 10 mM HEPES, 1 mM sodium pyruvate, 0.5 mg/mL Zeocin, and 0.5 mg/mL Geneticin). After 24 h at 37° C., remove medium and replace with 50 µL of dye loading buffer (Hank's balanced salt solution (HBSS) containing 25 mM HEPES, 0.04% Pluronate 127 and 8 µM Fluo3 Both from Molecular Probes)). After a 60 min incubation with the dye loading buffer at room temperature, aspirate the dye loading buffer and replace with 100 µL of HEPES/HBBS. Place the cell plate and the compound plate containing 2 µM MCH in buffer in the FLIPR and take a basal reading for 10 sec. The FLIPR then transfers 100 µl of the 2 µM MCH (for a final concentration in the assay of 1 µM MCH) to the cell plate and reads for 105 sec for a complete calcium flux peak in response to the agonist (1 µM MCH). To correct for variations between clones in numbers of cells per well, normalize the MCH response to the response induced by epinephrine.

Both the $^{125}$I-MCH binding and functional GTP$\gamma^{35}$S binding assays employ membranes isolated from a clone designated as clone 43. Typically, cells from 20 confluent T225 flasks are processed by washing the monolayers in cold phosphate-buffered saline (PBS), scraping the cells into same and re-suspending the cell pellet in (10 ml/gram of paste) in membrane prep buffer, pH 7.4 (250 mM Sucrose, 50 mM HEPES, pH 7.5, 1 mM MgCl$_2$, and protease inhibitors (1 Complete® tablet-EDTA (Roche Diagnostics), per 100 ml of membrane prep buffer). The cells were homogenized with a motor-driven Teflon-glass Potter-Elvehjem homogenizer using 5-10 strokes, followed by centrifugation at 260×g for 15 min at 4° C. The supernatant is collected and the pellets are resuspended in the membrane prep buffer and rehomogenized and centrifuged again at 260×g for 15 min at 4° C. for a total of 3 times. The pellets may then be discarded. The combined supernates are centrifuged at 30,000×g for 60 min at 4° C. The membrane pellet is resuspended in membrane prep buffer, to achieve a protein concentration of ~3-5 mg/mL (Pierce BCA assay with Bovine serum albumin as standard). Store aliquots at −80° C.

Binding of compounds to MCHR1 is assessed in a competitive binding assay employing $^{125}$I-MCH, compound and clone 43 membranes. Perform assays in 96-well Costar 3632 white clear bottom plates in a total volume of 200 µL containing 25 mM HEPES, pH 7.4, 10 mM CaCl$_2$, 2 mg/ml bovine serum albumin, 0.5% dimethyl sulfoxide (DMSO), 4-12 µg of clone 43 membranes, 200 µM $^{125}$I-MCH (NEN), 2.5 mg/mL of wheat germ agglutinin scintillation proximity assay beads (WGA-SPA beads, Amersham Inc., now GE Healthcare) and a graded dose of test compound. Non-specific binding is assessed in the presence of 0.1 µM unlabeled MCH. Bound $^{125}$I-MCH is determined by placing sealed plates in a Microbeta Trilux (Perkin Elmer Life and Analytical Sciences Inc.) and counting after a 12 h delay.

IC$_{50}$ values (defined as the concentration of test compound required to reduce specific binding of $^{125}$I-MCH by 50%) are determined by fitting the concentration-response data to a 4-parameter model (max response, min response, Hill coefficient, IC$_{50}$) using Excel® (Microsoft Corp.). K$_i$ values are calculated from IC$_{50}$ values using the Cheng-Prusoff approximation as described by Cheng et al. (Relationship between the inhibition constant (K$_i$) and the concentration of inhibitor which causes 50% inhibition (IC$_{50}$) of an enzymatic reaction, *Biochem. Pharmacol.*, 22: 3099-3108 (1973)). Exemplified compounds show a Ki of <1 µM under the binding assay conditions. Specifically, the compound of Example 58 exhibits an average MCHR1Ki of about 3 nM.

Functional antagonism of MCH activity is assessed by measuring the ability of test compound to inhibit MCH-stimulated binding of GTP$\gamma^{35}$S to clone 43 membranes. Perform assays in Costar 3632 white clear bottom plates in a total volume of 200 µl containing 50 mM Hepes, pH 7.4, 5 mM MgCl$_2$, 10 µg/mL saponin, 1.0 mg/mL bovine serum albumin, 100 mM NaCl, 3 µM GDP, 0.3 nM GTP$\gamma^{35}$S, 10 nM MCH (approximately equal to EC$_{90}$), 0.4 mg/ml of clone 43 membranes, 5.0 mg/ml of wheat germ agglutinin scintillation proximity assay beads (WGA-SPA beads, Amersham Inc., now GE Healthcare) and a graded dose of test compound. Seal the plates and leave for 16-18 h at 4° C. After a 1 h delay to allow plates to equilibrate to ambient temperature, determine bound GTP$\gamma^{35}$S by counting in a Microbeta Trilux (Perkin Elmer Life and Analytical Sciences Inc).

Determine IC$_{50}$ values (defined as the concentration of test compound required to reduce MCH-stimulated GTP$\gamma^{35}$S binding by 50%) by fitting the concentration-response data to a 4-parameter model (max response, min response, Hill coefficient, IC$_{50}$) using Excel (Microsoft). After verifying competitive antagonism by Schild analysis, calculate K$_b$ values from the IC$_{50}$ values for each antagonist and the EC$_{50}$ for MCH (determined independently) using a modification of the Cheng-Prusoff approximation as described by Leff and Dougal (*Trends Pharmacol. Sci.* (1993) 14: 110-112). Exemplified compounds show K$_b$ values of <1 µM under the functional assay conditions disclosed herein. Specifically, the compound of example 69 shows a MCHR1 Kb value of about 20 nM.

To demonstrate in vivo efficacy, administer compounds of the invention by oral gavage to diet-induced obese male Long-Evans rats (Harlan, Ind.) weighing 450-500 g. Vehicle consisted of 10% acacia and 0.15% saccharin in water.

House animals individually in a temperature regulated room (24° C.) with a reverse 12 hour light/dark cycle (dark 10:00/22:00). Make water and food (Teklad 95217, Harlan, Wis.) available ad libitum. Dose compounds orally once a day before onset of dark for 3 days. Measure daily food intake and body weight change for the 3 day period. The compound of Example 25 produces an average body weight reduction of about 6 grams@10 mg/Kg versus vehicle control.

Utility

As antagonists of the MCHR1 binding, a compound of the present invention is useful in treating conditions in human and non-human (especially companion) animals in which the MCHR1 receptor has been demonstrated to play a role. By inhibiting MCH activity the compounds of the present invention provide anorexic effects. That is, the compounds of the invention are useful as appetite suppressants and/or weight loss agents for the treatment of obesity. The compounds are thus useful for treating conditions caused, exacerbated, resulting from, or adjunct to obesity.

In treating non-human, non-companion animals, the compounds of the present invention are useful for reducing weight gain and/or improving the feed utilization efficiency and/or increasing lean body mass.

The compounds of this invention may be administered by a variety of routes including oral, rectal, transdermal, subcutaneous, intravenous, intramuscular, and intranasal. These compounds preferably are formulated prior to administration, the selection of which will be decided by the attending physician. Thus, another aspect of the present invention is a pharmaceutical composition comprising an effective amount of a compound of the invention, or a pharmaceutically acceptable salt thereof, and a pharmaceutically acceptable carrier, diluent, or excipient.

The specific dose administered is determined by the particular circumstances surrounding each situation. These circumstances include, the route of administration, the prior medical history of the patient, the pathological condition or symptom being treated, the severity of the condition/symptom being treated, and the age and sex of the recipient. However, it will be understood that the therapeutic dosage administered will be determined by the physician in the light of the relevant circumstances, or by the veterinarian for non-human recipients.

Generally, an effective minimum daily dose of a compound of the invention is about 10 to 200 mg per day. Typically, an effective maximum dose is about 200 to 1000 mg per day. The exact dose may be determined, in accordance with the standard practice in the medical arts of "dose titrating" the recipient; that is, initially administering a low dose of the compound, and gradually increasing the dose until the desired therapeutic effect is observed.

The pharmaceutical compositions of the present invention may be adapted for these various routes and may be administered to the patient, for example, in the form of tablets, capsules, cachets, papers, lozenges, wafers, elixirs, ointments, transdermal patches, aerosols, inhalants, suppositories, solutions, and suspensions. The total active ingredients in such composition comprises from 0.1% to 99.9% by weight of the formulation (see *Remington's Pharmaceutical Sciences*, 18th Edition, Mack Publishing Co. (1990) for a general discussion of formulations, drug delivery methods, etc.).

EXAMPLES

The following examples are only illustrative of the preparation protocols and applicants' ability to prepare compounds of the present invention based on the schemes presented and/or known modifications thereof. The examples are not intended to be exclusive or exhaustive of compounds made or obtainable. The abbreviations used herein are defined according to Aldrichimica Acta, Vol 17, No. 1, 1984 and are generally known to one of skill in the art or may be readily ascertained with minimal effort. Other abbreviations used in the experimentals are: N-methyl-2-pyrrolidinone (NMP), methyl t-butyl ether (MTBE), and room temperature (RT). The names of the compounds of the present invention are provided by ChemDraw Ultra®, version 7.0.1. Salts are named as the free base plus the conjugate acid.

Preparation 1

Triisopropyl-(2-methoxy-4-nitro-phenoxy)-silane

Dissolve 4-nitroguiacol (50.0 g, 295.6 mmol) in DMF (anhydrous, 1000 mL) and cool the solution to 0-5° C. Slowly add NaH (60% in mineral oil, 13.4 g, 335.0 mmol) keeping the temperature<10° C. Stir the yellow-orange solution mechanically at RT for 30 min and then cool to 0-5° C. Treat the mixture with triisopropylsilyl triflate (90.0 mL, 334.8 mmol), keeping the temperature<10° C. Stir at RT overnight. Quench the mixture with 14% aqueous $NH_4Cl$ (1000 mL) and then extract with EtOAc (3×1000 mL). Combine the organic solutions, wash with brine (1000 mL), and concentrate in vacuo to give a light yellow oil. Purify the oil by flash chromatography, using 100% hexanes then 10% EtOAc/hexanes, to provide 95.8 g (99.6%) of the title compound as a yellow oil. MS/ES m/z 326.2 $[M+H]^+$.

Preparation 2

1-[2-(2-Methoxy-4-nitro-phenoxy)-ethyl]-pyrrolidine

Add NaH (3.2 g, 80 mmol) portionwise to a 0° C. solution of 2-pyrrolidin-1-yl-ethanol (9.4 mL, 80 mmol) in DMF (180 mL). Stir the reaction 15-20 min until gas evolution ceases. Add a solution of 1-chloro-2-methoxy-4-nitro-benzene (15.0 g, 80 mmol) in DMF (100 mL) via cannula. Warm the reaction to 130° C. and stir for approximately 18 h. Cool to RT and dilute with EtOAc (300 mL). Wash with water (2×100 mL). Extract the organic layer with 1 N HCl (3×150 mL). Wash this acidic layer with EtOAc (100 mL) then basify by adding 1 N NaOH (500 mL) until pH=8-9. Extract the now basic aqueous layer with $CH_2Cl_2$ (3×150 mL). Dry the organic layer over $Na_2SO_4$ and concentrate to provide 8.5 g (40%) of the desired product as an orange solid. MS/ES m/z 267.3 $[M+H]^+$.

Preparation 3

3-Methoxy-4-triisopropylsilanyloxy-phenylamine

Dissolve triisopropyl-(2-methoxy-4-nitro-phenoxy)-silane (95.7 g, 294.0 mmol) in EtOH (1800 mL) and add 5% Pd/C (10.0 g). Hydrogenate the slurry at RT under 50 psi hydrogen for 8 h. Filter the slurry through a pad of Celite® and rinse with EtOH. Concentrate the filtrate in vacuo to give a brown oil. Purify the oil by flash chromatography, using a gradient from 100% hexanes to 20% EtOAc/hexanes, to provide 67.4 g (77.6%) of the title compound as a brown solid. MS/ES m/z 296.2 $[M+H]^+$.

Preparation 4

3-Methoxy-4-(2-pyrrolidin-1-yl-ethoxy)-phenylamine

Prepare the title compound by essentially following the procedure as described in Preparation 3, using 1-[2-(2-methoxy-4-nitro-phenoxy)-ethyl]-pyrrolidine. MS/ES m/z 237.3 $[M+H]^+$.

Preparation 5

4,5-Dihydro-thieno[2,3-c]pyran-7-one

Dissolve 2-thiophen-3-yl-ethanol (65.2 mL, 590.5 mmol) in $CH_2Cl_2$ (anhydrous, 1480 mL) and cool to 0-5° C. followed by addition of triphosgene (87.7 g, 295.5 mmol). Stir the mixture at 0-5° C. for about 5 min and then slowly add diisopropyethylamine (102.8 mL, 590.2 mmol) over a period of about 1.5 h, keeping the temperature<8° C. Stir the solution mechanically at 0-5° C. for 4.5 h, and then quench with 1 N HCl (890 mL). Separate the organic solution and extract the aqueous layer with $CH_2Cl_2$ (2×600 mL). Combine the organic solutions, wash with brine (900 mL), and concentrate in vacuo to provide 125.3 g (78.0% yield corrected for 70% HPLC purity) of the chloroformate as an oil.

Mix $AlCl_3$ (68.0 g, 510.0 mmol) and toluene (560 mL) and slowly add over a period of approximately 30 min, a solution of the chloroformate (125.2 g gross, 87.8 g net, 460.5 mmol) in toluene (1000 mL) keeping the temperature<40° C. Stir the mixture mechanically at RT for 1 h. Cool the mixture to 0-5° C. and slowly quench with aqueous saturated Rochelle's salt (potassium sodium tartrate) (800 mL) over 30 min, keeping the temperature<22° C. Separate the organic solution. Treat the aqueous layer with EtOAc (500 mL) and Celite® (130 g), stirring the mixture at RT for 10-15 min. Filter and rinse the filter cake with EtOAc. Separate the organic solution and extract the aqueous phase with additional EtOAc (2×500 mL). Combine all organic portions and wash with brine (1000 mL), then concentrate in vacuo to give an oil weighing 111.7 g that partially solidifies upon standing. Recrystillize the semi-solid from EtOAc/hexanes and dry under vacuum to give 67.2 g (94.6%) of the title compound. MS/ES m/z 155.1 $[M+H]^+$.

Preparation 6a

3-Iodo-4,5-dihydro-thieno[2,3-c]pyran-7-one and

Preparation 6b

2-Iodo-4,5-dihydro-thieno[2,3-c]pyran-7-one

Suspend 4,5-dihydro-thieno[2,3-c]pyran-7-one (1.1 g, 7.14 mmol) in $CCl_4$ (7 mL). Warm the resulting slurry to 65°

C. Add I₂ (1.08, 4.28 mmol) followed by bis-(trifluoroacetoxy)iodobenzene (1.84 g, 4.28 mmol, Aldrich). Continue heating for 10 min, then cool to RT. Pour into aqueous 1 N Na₂S₂O₃ (200 mL) and extract with CH₂Cl₂ (2×200 ml). Wash the combined organic layers with brine (200 ml). Dry the organic portion over Na₂SO₄, filter, and concentrate. Purify the resulting residue via silica gel chromatography (EtOAc/hexanes) to give 684 mg (34%) of the 3-iodo isomer. $R_f$=0.37 in 1 EtOAc/3 hexanes (UV visual). ES/MS m/z 281.0 [M+H]⁺. ¹H NMR (CDCl₃) δ 2.91 (t, 2H, J=6.2 Hz), 4.62 (t, 2H, J=6.2 Hz), 7.80 (s, 1H). Isolate a second spot to give 333 mg (17%) of the 2-iodo isomer. $R_f$=0.21 in 1 EtOAc/3 hexanes (UV visual). ES/MS m/z 281.0 [M+H]⁺. ES/MS m/z 281.0 [M+H]⁺. ¹H NMR (CDCl₃) δ 2.97 (t, 2H, J=6.1 Hz), 4.55 (t, 2H, J=6.1 Hz), 7.18 (s, 1H).

Preparation 7

3-Methyl-4,5-dihydro-thieno[2,3-c]pyran-7-one

Mix 3-iodo-4,5-dihydro-thieno[2,3-c]pyran-7-one (1.0, 3.57 mmol) and methyl boronic acid (428 mg, 7.14 mmol) in 7:3:1 dimethoxyethane:water:EtOH (10 mL) and add 2.0 M Na₂CO₃ (3.5 mL). Bubble dry argon gas through the reaction mixture for 10-15 min to remove oxygen. Add Pd(PPh₃)₄ (210 mg, 0.18 mmol) and heat using microwave irradiation to 130° C. for 45 min. Pour into 1 N NaOH (50 mL) and wash with hexanes (50 mL). Acidify the aqueous layer with 5N HCl until pH=1 and extract with EtOAc (3×50 mL). Wash the combined organic extracts with brine (50 mL). Concentrate, then add toluene (35 mL) to the crude intermediate. Add p-toluenesulfonic acid monohydrate (339 mg, 1.8 mmol) and heat to 80° C. overnight. Cool to RT, pour into aqueous NaHCO₃ (100 mL) and extract with EtOAc (3×100 mL). Wash the combined extracts with brine (100 mL). Dry the organic portion, filter and concentrate. Purify using silica gel chromatography (0-50% EtOAc/hexanes) to provide 133 mg (22%) of the desired product. ES/MS m/z 169.3 [M+H]⁺.

Preparation 8

2-Iodo-3-methyl-4,5-dihydro-thieno[2,3-c]pyran-7-one

Prepare the titled compound by essentially following procedures as described in Preparation 6a/6b, using 3-methyl-4,5-dihydro-thieno[2,3-c]pyran-7-one. ES/MS m/z 295.0 [M+H]⁺.

Preparation 9

3-Bromo-5-(4-chloro-phenyl)-thiophene-2-carboxylic acid methyl ester

Stir CuBr₂ (1.0 g, 4.44 mmol) and tert-butyl nitrite (0.66 mL, 5.55 mmol) in CH₃CN (915 mL) at RT for 30 min and add 3-amino-5-(4-chloro-phenyl)-thiophene-2-carboxylic acid methyl ester (1.0 g, 3.7 mmol). Stir the reaction at 70° C. for 4 h. Cool the mixture to RT, pour into 20% HCl (200 mL), and extract with CH₂Cl₂ (200 mL). Wash the organic layer with 20% HCl then dry and concentrate. Purify the crude material by chromatography, eluting with 10% EtOAc in hexane to give 65 g (53%) of the title compound. LC-MS/ES m/z (³⁵Cl, ⁸¹Br) 332.0 [M⁺].

Preparation 10

5-(4-Chloro-phenyl)-3-vinyl-thiophene-2-carboxylic acid methyl ester

Dissolve 3-bromo-5-(4-chloro-phenyl)-thiophene-2-carboxylic acid methyl ester (570 mg, 1.72 mmol) in toluene (10 mL) and add tributylvinyltin (0.55 mL, 1.89 mmol), and tetrakis(triphenylphosphine)palladium (40 mg, 0.034 mmol). Heat the mixture to 110° C. for 17 h. Cool the mixture to room temperature and concentrate in vacuo. Purify by chromatography eluting with 5% ethyl acetate/hexane to give 0.37 g (77%) of the title compound. LC-MS/ES m/z (³⁵Cl) 279.0 [M+H]⁻.

Preparation 11

5-(4-Chloro-phenyl)-3-(2-hydroxy-ethyl)-thiophene-2-carboxylic acid methyl ester Dissolve 5-(4-chloro-phenyl)-3-vinyl-thiophene-2-carboxylic acid methyl ester (5.35 g, 19.19 mmol) in tetrahydrofuran (220 mL) and cool to 0° C. Slowly add 9-borabicyclo[3.3.1]nonane (112 mL, 0.5 M, 56 mmol), warm the reaction to room temperature with stirring for 16 h. Cool the mixture to 0° C. and slowly add hydrogen peroxide (74 mL, 721 mmol) followed by 5 N sodium hydroxide (74 mL, 370 mmol). Add water (14 mL) and extract with ethyl acetate (3×150 mL). Dry the solution over Na₂SO₄, filter and evaporate. Purify by chromatography eluting with 50% ethyl acetate/hexane to afford 5.70 g (100%) of the title compound. LC-MS/ES m/z (³⁵Cl) 296.7.0 [M+H]⁺.

Preparation 12

2-(4-Chloro-phenyl)-4,5-dihydro-thieno[2,3-c]pyran-7-one

Dissolve 5-(4-chloro-phenyl)-3-(2-hydroxy-ethyl)-thiophene-2-carboxylic acid methyl ester (3.4 g, 11.46 mmol) in toluene (60 mL) and add p-toluenesulfonic acid monohydrate (0.3 g, 1.58 mmol) and heat to 80° C. for one hour. Cool the mixture to room temperature and dilute with ethyl acetate (50 mL). Wash the solution with 1 N NaOH and extract the aqueous portion twice with ethyl acetate. Combine the organic fractions, dry over Na₂SO₄, filter, and concentrate. Triturate the solid with ether and then filter and dry under vacuum to give 1.3 g (43%) of the title compound. LC-MS/ES m/z (³⁵Cl) 265.0 [M+H]⁺.

Preparation 13

2-(4-Chloro-phenyl)-3-methyl-4,5-dihydro-thieno[2,3-c]pyran-7-one

Add 4-chlorophenyl boronic acid (215 mg, 1.38 mmol) to a slurry of 2-iodo-3-methyl-4,5-dihydro-thieno[2,3-c]pyran-7-one (135 mg, 0.46 mmol) in CH₃CN (2 mL). Add PPh₃ (37 mg, 0.14 mmol) followed by 2.0 M Na₂CO₃ (0.69 mL). Bubble dry argon through the reaction for 15 min. Add Pd(OAc)₂ (12 mg, 0.05 mmol) and heat using microwave irradiation to 100° C. for 45 min. Pour the reaction into 1N HCl (50 mL) and extract with EtOAc (3×50 mL). Wash the combined organic extracts with brine (50 mL). Concentrate, dissolve the crude residue in toluene (5 mL) and treat with p-toluenesulfonic acid monohydrate (50 mg, 0.26 mmol). Heat to 80° C. for 8 h. Cool to RT, pour into aqueous NaHCO₃

(50 mL) and extract with EtOAc (3×50 mL). Wash the combined extracts with brine (50 mL) and concentrate. Purify the resulting residue using silica gel chromatography (0-50% EtOAc/hexanes) to provide 111 mg (87%) of the desired product.

Preparation 14

3-(2-Hydroxy-ethyl)-5-iodo-thiophene-2-carboxylic acid [3-methoxy-4-(2-pyrrolidin-1-yl-ethoxy)-phenyl]-amide

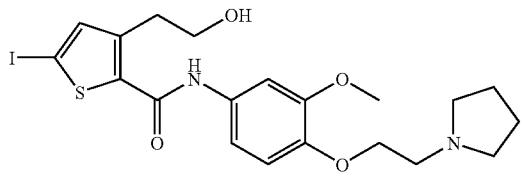

Dissolve 3-methoxy-4-(2-pyrrolidin-1-yl-ethoxy)-phenylamine (Preparation 4) (266 mg, 1.13 mmol) in toluene (8 mL) and add trimethylaluminum (2.0M solution in toluene, 565 μL, 1.13 mmol). Stir 5-10 min at RT and add 2-iodo-4,5-dihydro-thieno[2,3-c]pyran-7-one (315 mg, 1.13 mmol). Warm the reaction to 50° C. overnight. Cool to RT, add an aqueous solution of Rochelle's salt (100 mL), and stir for 1 h. Add 1N NaOH (50 mL) and extract with EtOAc (3×100 mL). Combine the organic layers and wash with brine (100 mL). Concentrate the organic portion to give a crude solid. Triturate with diethyl ether, filter and collect 370 mg (63%) of the product as a white solid. MS/ES m/z 517.0 [M+H]$^+$.

Prepare the intermediates in the table below by essentially following procedures as describe in Preparation 14 using the appropriate 4,5-dihydro-thieno[2,3-c]pyran-7-one and corresponding phenylamine.

| Prep | Chemical Name | MS/ES (m/z) |
|---|---|---|
| 15 | 5-(4-Chloro-phenyl)-3-(2-hydroxy-ethyl)-4-methyl-thiophene-2-carboxylic acid [3-methoxy-4-(2-pyrrolidin-1-yl-ethoxy)-phenyl]-amide | 515.2 [M + H]$^+$ |
| 16 | 3-(2-Hydroxy-ethyl)-thiophene-2-carboxylic acid (3-methoxy-4-triisopropylsilanyloxy-phenyl)-amide | 450.4 [M + H]$^+$ |

Preparation 17

2-Iodo-6-[3-methoxy-4-(2-pyrrolidin-1-yl-ethoxy)-phenyl]-5,6-dihydro-4H-thieno[2,3-c]pyridin-7-one Add TEA (576 μL, 4.14 mmol) to a 0° C. slurry of 3-(2-hydroxy-ethyl)-5-iodo-thiophene-2-carboxylic acid [3-methoxy-4-(2-pyrrolidin-1-yl-ethoxy)-phenyl]-amide (1.64 g, 3.19 mmol) in 20 mL CH$_2$Cl$_2$. Add methanesulfonyl chloride (320 μL, 4.14 mmol) and stir overnight. Add more methanesulfonyl chloride if needed to consume all the alcohol. When the mesylate is completely formed by MS, pour into 1 N NaOH (250 mL) and extract with CH$_2$Cl$_2$ (2×200 mL). Wash the combined organic layers with 100 mL brine, dry over Na$_2$SO$_4$, filter, and concentrate. Dissolve the crude mesylate in DMF (20 mL). Cool to 0° C. and add NaH (192 mg, 4.79 mmol). Stir overnight while warming to RT. Repeat the same aqueous workup as done for the mesylate step. Purify the crude product via silica gel chromatography using a 0-10% gradient of (2N NH$_3$ in MeOH)/CHCl$_3$ to give 1.07 g (68%) of the desired product. MS/ES m/z 499.2 [M+H]$^+$.

Preparation 18

6-(3-Methoxy-4-triisopropylsilanyloxy-phenyl)-5,6-dihydro-4H-thieno[2,3-c]pyridin-7-one Prepare the title compound by essentially following the procedures as described in Preparation 17, using 3-(2-hydroxy-ethyl)-thiophene-2-carboxylic acid (3-methoxy-4-triisopropylsilanyloxy-phenyl)-amide. MS/ES m/z 432.1 [M+H]$^+$.

Preparation 19

5,6-Dihydro-4H-thieno[2,3-c]pyridin-7-one

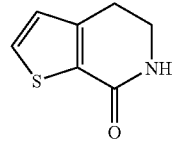

Prepare the title compound by essentially following procedures as found in Aparajithan, K.; Thompson, A. C.; Sam, J. J. Heterocyclic. Chem. 1966, 3, 466. Dissolve 4,5-dihydro-cyclopenta[b]thiophen-6-one (Bonini, B. F.; et. al. Eur. J. Org. Chem. 2004, 4442 and references cited therein) (0.658 g, 4.77 mmol) in MeOH (50 mL), and add hydroxylamine hydrochloride (0.365 g, 5.25 mmol) and NaOAc (2.35 g, 28.62 mmol). Stir the reaction at RT overnight. Remove the organic solvent in vacuo, and treat the residue with EtOAc (60 mL). Filter through silica gel, wash with EtOAc, and concentrate. Treat the residue with PPA (30 g), heating to 130° C. in an oil bath and with occasional stirring over 30 min. Allow the reaction to cool to RT and pour into ice water (100 mL). Extract with CH$_2$Cl$_2$ (3×150 mL). Wash the combined organic layers with 0.1 M NaOH (100 mL), dry over Na$_2$SO$_4$ and concentrate. Purify the material by chromatography, eluting with 75% EtOAc/hexanes to give the title compound (0.521 g, 71%). MS/ES m/z 154.1 [M+H]$^+$ Alternate Procedure:

Step 1. 2-Thiophene-3-yl-ethylamine hydrochloride

Slowly add borane methyl sulfide complex (30.4 mL, 304.4 mmol) to a solution of thiophen-3-yl-acetonitrile (25.0 g, 203.0 mmol) in tetrahydrofuran (450 mL). Heat the reaction at reflux for 16 h and then cool to RT. Slowly quench the reaction with methanol (50 mL) until no foaming is observed. To this mixture slowly add methanol (100 mL) which is saturated with hydrogen chloride. Stir the mixture at RT for 20 min before concentrating in vacuo. Add methanol (100 mL) to the mixture and concentrate in vacuo. Suspend the resulting solid in diethyl ether (200 mL) and filter to afford 31.1 g (94%) of the crude title compound. MS/ES m/z 128.3 [M+H]$^+$.

Step 2. (2-Thiophen-3-yl-ethyl)-carbamic acid ethyl ester

Add diisopropylethylamine (54.0 g, 418.0 mmol) to a suspension of 2-thiophene-3-yl-ethylamine hydrochloride in dichloromethane (400 mL) and stir the mixture for 40 min at RT. Cool the mixture to 0° C. and add dropwise ethyl chloroformate (22.7 g, 209.0 mmol) over 15 min. After the addition is complete, stir the reaction for 1 h at 0° C. Wash with 10% sodium bisulfate (500 mL). Extract the aqueous portion with dichloromethane (2×100 mL) and dry the combined organic portions over $Na_2SO_4$, filter and concentrate in vacuo. Purify the resulting residue by silica gel chromatography, using an eluent of 100% dichloromethane to give 22.6 g (60%) of the title compound. MS/ES m/z 200.3 $[M+H]^+$.

Step 3. 5,6-Dihydro-4H-thieno[2,3-c]pyridin-7-one

Add phosphorus pentoxide (32.1 g, 225.8 mmol) to a solution of 2-thiophen-3-yl-ethyl)-carbamic acid ethyl ester (22.5 g, 112.9 mmol) in phosphorus oxychloride (167 ml) and heat the reaction at 110° C. for 3 h 45 min. Cool the mixture to RT and concentrate in vacuo. Dissolve the residue in dichloromethane (50 mL) and pour into 300 g of ice. Adjust the mixture to pH=7 with 5 N sodium hydroxide and extract with dichloromethane (4×100 mL). Dry the combined organic portions ($Na_2SO_4$), filter, and concentrate in vacuo. Purify the resulting residue by silica gel chromatography, eluting with 0% to 70% ethyl acetate/hexane to afford 8.38 g (48%) of the title compound. MS/ES m/z 154.3 $[M+H]^+$.

Preparation 20

2-Bromo-5,6-dihydro-4H-thieno[2,3-c]pyridin-7-one

Dissolve 5,6-dihydro-4H-thieno[2,3-c]pyridin-7-one (4.80 g, 31.37 mmol) in HOAc (40 mL) and water (30 mL). Cool to 0° C. and add $Br_2$ (1.8 mL, 34.51 mmol) dropwise. Stir the reaction at 0° C. for 1 h. Dilute the reaction mixture with water (100 mL) and extract with EtOAc (3×100 mL). Wash the combined organic layers with 5% $Na_2SO_3$ (2×50 mL), saturated $NaHCO_3$ (2×100 mL), dry over $Na_2SO_4$, filter, and concentrate to give 6.198 g (85%) of the title compound. MS/ES m/z ($^{81}Br$) 233.9 $[M+H]^+$; $^1H$-NMR (400 MHz, $CDCl_3$) δ 2.87 (t, J=6.9 Hz, 2H), 3.59 (t, J=6.9 Hz, 2H), 6.21 (bs, 1H), 6.93 (s, 1H).

Preparation 21

2-(4-Methoxy-phenyl)-5,6-dihydro-4H-thieno[2,3-c]pyridin-7-one

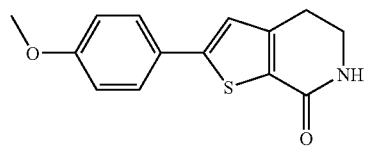

Combine 2-bromo-5,6-dihydro-4H-thieno[2,3-c]pyridin-7-one (1.024 g, 4.42 mmol), 4-methoxyphenyl boronic acid (0.671 g, 4.42 mmol), $Na_2CO_3$ (0.94 g, 8.83 mmol), in water (10 mL), dimethoxyethane (75 mL) and $CH_3OH$ (50 mL). Purge with nitrogen for 5 min. Add $Pd(PPh_3)_4$ (0.153 g, 0.1325 mmol) and reflux the resulting mixture overnight. Cool the reaction to RT and dilute with water (100 mL). Extract with EtOAc (3×100 L), and concentrate. Treat the residue with EtOAc (40 mL), collect the solid and wash with EtOAc (20 mL) and $Et_2O$ (2×20 mL) to give the title compound (0.950 g). Concentrate the filtrate and purify the resulting residue by chromatography to give additional product (0.140 g). The overall yield is 1.090 g (95%). MS/ES m/z 260.0 $[M+H]^+$.

Preparation 22

2-(4-Fluoro-phenyl)-5,6-dihydro-4H-thieno[2,3-c]pyridine-7-one

Add tetrakis(triphenylphosphine) palladium(0) (0.075 g, 0.065 mmol) to a degassed solution of 2-bromo-5,6-dihydro-4H-thieno[2,3-c]pyridin-7-one (0.5 g, 2.15 mmol), 4-fluorophenylboronic acid (0.30 g, 2.15 mmol), and sodium carbonate (0.46 g, 4.30 mmol) in N,N-dimethylformamide (21 mL), methanol (5 mL) and water (1 mL). Heat the reaction at 90° C. for 16 h. Allow the reaction to cool to RT and pour into water (75 mL). Filter the resulting solid and dry in vacuo at 80° C. to give 0.40 g (75%) of the title compound. MS/ES m/z 248.0 $[M+H]^+$.

Prepare the intermediates in the table below by following the procedure of the Suzuki coupling essentially as described in Preparation 21 (for Preparation 23) or 22 (for Preparation 24) using the appropriate arylboronic acid.

| Prep | Chemical Name | MS/ES (m/z) |
|---|---|---|
| 23 | 2-(4-Chloro-phenyl)-5,6-dihydro-4H-thieno[2,3-c]pyridin-7-one | ($^{35}Cl$) 264.8 $[M + H]^+$ |
| 24 | 2-(4-Trifluoromethoxy-phenyl)-5,6-dihydro-4H-thieno[2,3-c]pyridine-7-one | 314.0 $[M + H]^+$ |

Preparation 25

2-Bromo-6H-thieno[2,3-c]pyridin-7-one

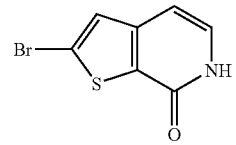

Suspend (E)-3-(5-bromo-thiophen-3-yl)-acrylic acid (Gronowitz, S.; Ander, I. Chemica Scripta 1980, 15, 145) (2.04 g, 8.79 mmol) in $CH_2Cl_2$ (30 mL). Treat with oxalyl chloride (1.5 mL, 17.58 mmol) followed by the addition of DMF (3 drops). Stir the reaction at RT for 30 min to obtain a clear solution and continue stirring for 1.5 h. Remove the excess reagent and solvent in vacuo. Dissolve the resulting residue in 1,4-dioxane (10 mL), place in an addition funnel, and add dropwise to a solution of $NaN_3$ (1.8 g, 26.37 mmol) in water (10 mL) and acetone (10 mL) at 0° C. During the addition, maintain the internal temperature below 5° C. Stir the mixture at 0° C. for 1 h. Dilute with water (15 mL), and extract with EtOAc (3×30 mL). Combine the organic layers and concentrate in vacuo without heating. Dissolve the resulting residue in EtOAc (50 mL), and wash with water (30 mL) and brine (20 mL). Dry over $Na_2SO_4$, filter, and concentrate in vacuo without heat to give the crude acyl azide intermediate.

Dissolve the crude acyl azide in 1,4-dioxane (10 mL) and place in an addition funnel which is attached to a flask containing Dowtherm A® (15 mL) and a Dean-Stark trap with a condenser. Heat the Dowtherm A® mixture to 230° C., and add the acyl azide solution dropwise. The internal temperature of the reaction drops to 160° C. during the addition and raises to 230° C. afterwards. Collect the low boiling solvent in the Dean-Stark trap. Stir the reaction at 230° C. for 1 h. Cool to RT and dilute with hexane (40 mL). Collect the precipitate by filtration and wash with hexanes (2×20 mL) to give 1.838 g (91%) of the title compound. $^1$H NMR (DMSO-$d_6$) δ 6.64 (d, 1H, J=6.8 Hz), 7.29 (d, 1H, J=6.8 Hz), 7.57 (s, 1H), 11.64 (bs, 1H). MS/ES m/z ($^{81}$Br) 229.8 [M−H]$^-$.

Preparation 26

5-Chloro-thiophene-2-carboxylic acid (2,2-diethoxyethyl) amide

Add 5-chlorothiophene-2-carboxylic acid (100 g, 0.60 mol) and dichloromethane (1000 mL) to a 3 L three-necked round bottom flask equipped with an overhead stirrer, nitrogen inlet/outlet, addition funnel, and thermocouple. Stir the resulting solution under nitrogen while cooling to 4° C. Add via addition funnel 2,2-diethyoxyethylamine (88.5 ml, 0.60 mol) in dichloromethane (35 mL) over 12 minutes. Add 1-(3-dimethylaminopropyl)-3-ethylcarbodiimide hydrochloride (123 g, 0.64 mol) to the chilled mixture. Add additional dichloromethane (165 mL) and stir the reaction mixture for 22 h at room temperature. Quench the reaction with water (1000 mL) and separate the resulting layers. Back extract the aqueous layer with dichloromethane (500 mL) and combine the organic layers. Dry over sodium sulfate and purify through a silica gel bed eluting with dichloromethane followed by a mixture of 1% MeOH in dichloromethane and then a mixture of 10% MeOH in dichloromethane to afford 108 g (65%) of the title compound as a white solid. $^1$H NMR (500 MHz, CDCl$_3$): δ 7.26 (d, J=3.5 Hz, 1H), 6.85 (d, J=3.5 Hz, 1H), 6.37 (bs, 1H), 4.57 (t, J=5.5 Hz, 1H), 3.68-3.74 (m, 2H), 3.48-3.57 (m, 4H), 1.19 (t, J=7.5 Hz, 6H).

Preparation 27

5-(4-chlorophenyl)-thiophene-2-carboxylic acid (2,2-diethyoxyethyl) amide

Add 5-chloro-thiophene-2-carboxylic acid (2,2-diethoxyethyl) amide (50.15 g, 0.18 mol), 4-chlorophenylboronic acid (29.84 g, 0.18 mol), potassium carbonate (50 g, 0.36 mol), [1,3-bis(2,6-diisopropylphenyl)imidazol-2-ylidene)(3-chloropyridyl)] palladium (II) dichloride (4.40 g, 0.006 mol), and EtOH (1000 mL) to a 2 L three-necked round bottom flask equipped with a overhead stirrer, reflux condenser, nitrogen inlet/outlet, addition funnel, and thermocouple. Heat the resulting slurry for 35 minutes, then add activated carbon (5.8 g) and heat for an additional 0.5 h. Filter the resulting slurry through glass microfibre filter and rinse solids with EtOH (500 mL). Remove solvent from the filtrate under reduced pressure until 15-20% solvent remains. To this filtrate, add water (1300 mL) and stir the resulting slurry at room temperature for 1 h, then at 0-5° C. for 0.5 h. Filter the slurry, rinse the solids with water (1000 mL), and dry to afford 66 g of crude 5-(4-chlorophenyl)-thiophene-2-carboxylic acid (2,2-diethoxyethyl) amide. Reflux the crude 5-(4-chlorophenyl)-thiophene-2-carboxylic acid (2,2-diethyoxyethyl) amide in heptane (1625 mL) for 1 h then filter through a glass microfibre filter. Transfer the filtrate to a round bottom flask and remove solvent until 725 mL of solvent remained. Stir the mixture under chilled conditions for 40 min. Filter the resulting slurry, rinse with heptane (100 mL), and dry to afford 41 g (64%) as a white solid. $^1$H NMR (500 MHz, CDCl$_3$): δ 7.54 (d, J=9.0 Hz, 2H), 7.45 (d, J=4.5 Hz, 1H), 7.38 (d, J=9.0 Hz, 2H), 7.24 (d, J=4.5 Hz, 1H), 6.20 (bs, 1H), 4.62 (t, J=5.5 Hz, 1H), 3.73-3.79 (m, 2H), 3.57-3.62 (m, 4H), 1.25 (t, J=7.0 Hz, 6H), Preparation 28

5-(4-Chlorophenyl)-thiophene-2-carboxylic acid (2-oxoethyl) amide

Add water (21 mL) followed by trifluoroacetic acid (100 g) to a 250 mL three-necked round bottom flask equipped with an overhead stirrer, nitrogen inlet/outlet, and thermocouple. To the stirring TFA solution, add 5-(4-chlorophenyl)-thiophene-2-carboxylic acid (2,2-diethyoxyethyl) amide (25 g, 0.07 mol) in one portion. Stir the reaction mixture for 4 h, pour onto ice/water (1200 mL), and stir for 1.25 h. Filter the resulting slurry and rinse the solid with water (500 mL) and heptane (500 mL), and then dry to give 18.65 g (95%) of the title compound as a yellow-white solid. LC-MS/ES m/z ($^{35}$Cl)=278 (M−H)$^-$. $^1$H NMR (500 MHz, CDCl$_3$): δ 4.40 (d, J=4.0 Hz, 2H), 6.69 (bs, 1H), 7.26 (d, J=3.0 Hz, 1H), 7.40 (d, J=9.0 Hz, 2H), 7.53-7.58 (m, 3H), 9.78 (s, 1H).

Preparation 29

2-(4-Chloro-phenyl)-6H-thieno[2,3-c]pyridin-7-one

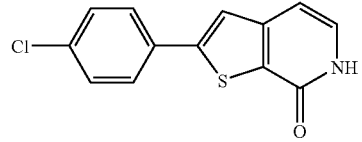

Combine 2-bromo-6H-thieno[2,3-c]pyridin-7-one (25.0 g, 108.7 mmol), 4-chlorophenylboronic acid (18.7 g, 119.5 mmol), sodium carbonate (23.5 g, 217.3 mmol), ethanol (121 mL), 1,2-dimethoxyethane (604 mL), and water (121 mL). Purge the mixture with nitrogen for 20 min. Add tetrakis (triphenylphosphine)palladium (3.77 g, 3.26 mmol). Heat the reaction mixture at 85° C. overnight. Allow the reaction to cool to RT. Reduce the reaction solvent volume to half on a rotory evaporator. Filter the mixture with water (2×400 mL), ether (400 mL), and ethylacetate (20 mL) and dry the solids in vacuo at 40° C. to give 25.4 g (89%) of the title compound. LC-MS/ES m/z ($^{35}$Cl) 262.0 [M+H]$^+$.
Alternate Preparation:
Add trifluoromethane sulfonic acid (3 mL, 0.03 mol) and 5-(4-chlorophenyl)-thiophene-2-carboxylic acid (2-oxoethyl) amide (1 g, 0.004 mol) to a 25 mL three-necked round bottom flask equipped with a stir bar, Dean-Stark trap, nitrogen inlet/outlet, and thermocouple. Heat the reaction mixture to 95° C. for 2 h, then cool to 40° C., and pour onto cold water (20 mL, 1.11 mol). Stir the mixture for 10 min. Filter the resulting slurry and rinse the solids with water (100 mL). Dry to afford crude 2-(4-chlorophenyl)-6H-thieno[2,3-c]pyridine-7-one (0.95 g, 0.004 mol) as a brown solid. LC-MS/ES m/z ($^{35}$Cl) 262 [M+1]$^+$.

Preparation 30

Toluene-4-sulfonic acid 4-bromo-2-methoxy-phenyl ester

Dissolve 4-bromo-2-methoxy-phenol (1.032 g, 5.08 mmol) in CH$_2$Cl$_2$ (10 mL), and treat with TsCl (0.969 g, 5.08 mmol) followed by Et$_3$N (1.06 mL, 7.62 mmol). Stir the reaction at RT for 2 h. Dilute with EtOAc (100 mL) and wash with water (2×30 mL). Dry with Na$_2$SO$_4$, filter, and concentrate to give 1.81 g (100%) of the title compound. MS/ES m/z ($^{81}$Br) 380.9 [M+Na]$^+$.

Preparation 31

Toluene-4-sulfonic acid 4-bromo-phenyl ester

Prepare the title compound by essentially following the procedure as described for Preparation 30, using 4-bromophenol (1.58 g, 9.13 mmol) to give 2.76 g (92%) of product. $^1$H NMR (400 MHz, CDCl$_3$) δ 2.45 (s, 3H), 6.84-6.89 (m, 2H), 7.32 (d, J=8.7 Hz, 2H), 7.38-7.43 (m, 2H), 7.68-7.72 (m, 2H).

Preparation 32

Toluene-4-sulfonic acid 2-methoxy-4-[2-(4-methoxy-phenyl)-7-oxo-4,7-dihydro-5H-thieno[2,3-c]pyridin-6-yl]-phenyl ester

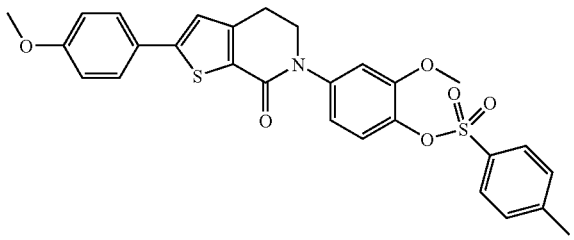

Combine 2-(4-methoxy-phenyl)-5,6-dihydro-4H-thieno[2,3-c]pyridin-7-one (0.245 g, 0.943 mmol), toluene-4-sulfonic acid 4-bromo-2-methoxy-phenyl ester (0.404 g, 1.13 mmol), 4,5-bis(diphenylphosphino)-9,9-dimethylxanthene (xantphos) (27.3 mg, 0.05 mmol), and Cs$_2$CO$_3$ (0.461 g, 1.41 mmol) in dioxane (25 mL). Purge the reaction vessel with nitrogen for 5 min, and then add Pd$_2$(dba)$_3$ (8.6 mg, 0.09 mmol). Reflux the reaction mixture and stir 16 h. Dilute with EtOAc (100 mL), wash with water (2×30 mL), dry with Na$_2$SO$_4$, filter and concentrate. Purify the crude material by chromatography, eluting with 30-50% EtOAc/hexanes to give 0.432 g (86%) of the title compound. LC-MS/ES m/z 536.0 [M+H]$^+$.

Prepare the compounds in the table below by essentially following the procedure as described in Preparation 32, using the appropriate thienopyridinone with the appropriate arylbromide or heteroarylbromide.

| Prep | Chemical Name | MS/ES (m/z) |
|---|---|---|
| 33 | Toluene-4-sulfonic acid 4-[2-(4-methoxy-phenyl)-7-oxo-4,7-dihydro-5H-thieno[2,3-c]pyridin-6-yl]-phenyl ester | 506.0 [M + H]$^+$ |
| 34* | 4-[2-(4-Chloro-phenyl)-7-oxo-4,7-dihydro-5H-thieno[2,3-c]pyridin-6-yl]-2-methoxy-benzoic acid methyl ester | ($^{35}$Cl) 428.0 [M + H]$^+$ |
| 35 | 2-Chloro-4-[2-(4-Chloro-phenyl)-7-oxo-4,7-dihydro-5H-thieno[2,3-c]pyridin-6-yl]-benzoic acid methyl ester | ($^{35}$Cl$^{37}$C) 433.9 [M + H]$^+$ |
| 36 | 4-[2-(4-Fluoro-phenyl)-7-oxo-4,7-dihydro-5H-thieno[2,3-c]pyridin-6-yl]-2-methoxy-benzoic acid methyl ester | 412.0 [M + H]$^+$ |
| 37 | 4-[2-(4-Trifluoromethoxy-phenyl)-7-oxo-4,7-dihydro-5H-thieno[2,3-c]pyridin-6-yl]-2-methoxy-benzoic acid methyl ester | 478.0 [M + H]$^+$ |

*Workup: Dilute with EtOAc, filter through Celite ®, and concentrate. Suspend residue in Et$_2$O and filter.

Preparation 38

6-(4-Hydroxy-3-methoxy-phenyl)-2-(4-methoxy-phenyl)-5,6-dihydro-4H-thieno[2,3-c]pyridin-7-one Combine toluene-4-sulfonic acid 2-methoxy-4-[2-(4-methoxy-phenyl)-7-oxo-4,7-dihydro-5H-thieno[2,3-c]pyridin-6-yl]-phenyl ester (1.029 g, 1.92 mmol) and KOH (2.15 g, 38.48 mmol) with EtOH (30 mL) and water (20 mL). Reflux the reaction for 10 h and dilute with water (50 mL). Acidify with 5.0 M HCl (8 mL). Remove the organic solvent in vacuo and dilute the residue with water (10 mL). Collect the solid material by filtration and wash with water (3×10 mL) and Et$_2$O (2×15 mL) then dry in a vacuum oven to give 0.646 g (88%) of the title compound. MS/ES m/z 382.0 [M+H]$^+$.

Preparation 39

6-(4-Hydroxy-phenyl)-2-(4-methoxy-phenyl)-5,6-dihydro-4H-thieno[2,3-c]pyridin-7-one Prepare the title compound by essentially following the procedure as described for Preparation 38, using toluene-4-sulfonic acid 4-[2-(4-methoxy-phenyl)-7-oxo-4,7-dihydro-5H-thieno[2,3-c]pyridin-6-yl]-phenyl ester (0.256 g, 0.51 mmol) to give 0.135 g, (76%) of the product. LC-MS/ES m/z 352.3 [M+H]$^+$.

Example 1

2-(4-Methoxy-phenyl)-6-[3-methoxy-4-(2-pyrrolidin-1-yl-ethoxy)-phenyl]-5,6-dihydro-4H-thieno[2,3-c]pyridin-7-one, hydrochloride Combine 2-(4-methoxy-phenyl)-5,6-dihydro-4H-thieno[2,3-c]pyridin-7-one (0.234 g, 0.90 mmol), 1-[2-(4-bromo-2-methoxy-phenoxy)-ethyl]-pyrrolidine (Bastian, J. A., et al WO 9725033 A1) (0.271 g, 0.90 mmol), N,N'-dimethylethane-1,2-diamine (16 mg, 0.18 mmol), K$_2$CO$_3$ (0.249 g, 1.81 mmol), and CuI (17 mmol, 0.09 mmol) in toluene (10 mL) and stir at 110° C. for 48 h. Dilute with EtOAc (100 mL) and wash with water (50 mL), containing NH$_3$—H$_2$O (5 mL) three times. Dry over Na$_2$SO$_4$, filter and purify the material by chromatography, eluting with 7% 2 M NH$_3$ in CH$_3$OH, and 93% CH$_2$Cl$_2$ to give 0.125 g. Dissolve the material in CH$_3$OH (5 mL) and treat with 1.0 M HCl in EtOH (270 µL, 0.27 mmol). Stir at RT for 5 min and concentrate to give the title compound (0.133 g, 0.26 mmol, 100%). LC-MS/ES m/z 479.3 [M+H]$^+$.

Example 2

6-[3-Methoxy-4-(2-morpholin-4-yl-ethoxy)-phenyl]-2-(4-methoxy-phenyl)-5,6-dihydro-4H-thieno[2,3-c]pyridin-7-one, hydrochloride Treat 6-(4-hydroxy-3-methoxy-phenyl)-2-(4-methoxy-phenyl)-5,6-dihydro-4H-thieno[2,3-c]pyridin-7-one (0.12 g, 0.31 mmol) in DMF (5 mL) with 4-(2-chloro-ethyl)-morpholine hydrochloride salt (59 mg, 0.31 mmol) and 60% NaH (38 mg, 0.94 mmol). Stir the reaction at 85° C. overnight. Quench with water (5 mL) and dilute with EtOAc (150 mL). Separate the phases and wash the organic phase with water (3×50 mL), dry over $Na_2SO_4$, filter, and concentrate. Purify the crude material by chromatography, eluting with 1% $NH_3$—$H_2O$, 10% $CH_3OH$ and 90% EtOAc to give 31 mg. Dissolve the material in $CH_3OH$ (2 mL), and treat with 1.0 M HCl in EtOAc (65 µL, 0.065 mmol), with stirring at RT for 5 min. Remove the solvent in vacuo to give 33 mg (20%) of the title compound. LC-MS/ES m/z 495.0 [M+H]$^+$.

Example 3

2-(4-Methoxy-phenyl)-6-[4-(2-morpholin-4-yl-ethoxy)-phenyl]-5,6-dihydro-4H-thieno[2,3-c]pyridin-7-one, hydrochloride Prepare the title compound by essentially following the procedure as described for Example 2, using 6-(4-hydroxy-phenyl)-2-(4-methoxy-phenyl)-5,6-dihydro-4H-thieno[2,3-c]pyridin-7-one (0.177 g, 0.51 mmol) to give 0.135 g (53%). LC-MS/ES m/z 465.3 [M+H]$^+$.

Example 4

2-(2,4-Dichloro-phenyl)-6-[3-methoxy-4-(2-pyrrolidin-1-yl-ethoxy)-phenyl]-5,6-dihydro-4H-benzo[b]thiophen-7-one

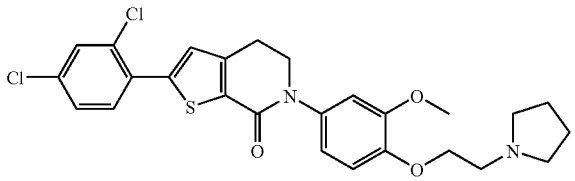

Add $K_2CO_3$ (200 mg, 1.43 mmol) to a RT slurry of 2-iodo-6-[3-methoxy-4-(2-pyrrolidin-1-yl-ethoxy)-phenyl]-5,6-dihydro-4H-thieno[2,3-c]pyridin-7-one (357 mg, 0.72 mmol) in acetonitrile (3 mL) and water (0.5 mL). Add 2,4-dichlorophenyl boronic acid (151 mg, 0.79 mmol) followed by triphenylphosphine (55 mg, 0.21 mmol). Add Pd(OAc)$_2$ (16 mg, 0.7 mmol) and heat to 80° C. under a nitrogen atmosphere for 1.5 h. Cool to RT and load directly onto a silica plug. Purify via silica gel chromatography using a 0-30% gradient of (2 N $NH_3$ in MeOH)/CHCl$_3$ to give 155 mg (42%) of the desired final product. MS/ES m/z ($^{35}Cl^{35}Cl$) 517.0 [M+H]$^+$.

Prepare the examples in the table below, by essentially following the procedures as described in Example 4, using 4-(N,N-dimethylamino)phenylboronic acid, 4-(methanesulfonyl)phenylboronic acid, 4-chlorophenylboronic acid, and p-tolylboronic acid respectively.

| Example | Chemical Name | MS/ES (m/z) |
|---|---|---|
| 5 | 2-(4-Dimethylamino-phenyl)-6-[3-methoxy-4-(2-pyrrolidin-1-yl-ethoxy)-phenyl]-5,6-dihydro-4H-thieno[2,3-c]pyridin-7-one | 492.0 [M + H]$^+$ |
| 6 | 2-(4-Methanesulfonyl-phenyl)-6-[3-methoxy-4-(2-pyrrolidin-1-yl-ethoxy)-phenyl]-5,6-dihydro-4H-thieno[2,3-c]pyridin-7-one | 527.0 [M + H]$^+$ |
| 7 | 2-(4-Chloro-phenyl)-6-[3-methoxy-4-(2-pyrrolidin-1-yl-ethoxy)-phenyl]-5,6-dihydro-4H-thieno[2,3-c]pyridin-7-one | ($^{35}Cl$) 483.0 [M + H]$^+$ |
| 8* | 6-[3-Methoxy-4-(2-pyrrolidin-1-yl-ethoxy)-phenyl]-2-p-tolyl-5,6-dihydro-4H-thieno[2,3-c]pyridin-7-one, hydrochloride | 463.0 [M + H]$^+$ |

*Prepare the hydrochloride salt by dissolving the free base in $CH_2Cl_2$ and treating with 2.0 M HCl in diethyl ether.

Alternatively, prepare 2-(4-chloro-phenyl)-6-[3-methoxy-4-(2-pyrrolidin-1-yl-ethoxy)-phenyl]-5,6-dihydro-4H-thieno[2,3-c]pyridin-7-one (Example 7) as described in Preparation 40, 41, and 44, followed by alkylation as described in Example 9.

Preparation 40

2-Bromo-6-(3-methoxy-4-triisopropylsilanyloxy-phenyl)-5,6-dihydro-4H-thieno[2,3-c]pyridin-7-one Dissolve 6-(3-methoxy-4-triisopropylsilanyloxy-phenyl)-5,6-dihydro-4H-thieno[2,3-c]pyridin-7-one (5 g, 11.6 mmol) in THF (100 mL) in a three neck round bottom flask. Cool the solution in a dry ice/acetone bath. In one neck, set up a chilled (dry ice/acetone) addition funnel containing 1,2-dibromo-1,1,2,2-tetrafluoro-ethane (2.8 mL, 23.2 mmol) in 10 mL THF. Add t-BuLi (9.7 mL of 1.2 M solution in pentane, 11.6 mmol) quickly through one of the side necks allowing the solution to run down the inside of the flask. Within 30 sec of completion of the t-BuLi addition, open the addition funnel containing the electrophile. Stir 5-10 min, then pour into aqueous NaHCO$_3$ (300 mL) and extract with EtOAc (2×300 mL). Wash the combined organic layers with brine (200 mL). Concentrate and purify via silica gel chromatography using a 0-25% gradient of EtOAc/hexanes to give 2.78 g (47%) of the desired product. MS/ES m/z (79Br) δ 10.0 [M+H]$^+$; R$_f$=0.52 in 4:1 Hexanes:EtOAc.

Preparation 41

2-(4-Chloro-phenyl)-6-(3-methoxy-4-triisopropylsilanyloxy-phenyl)-5,6-dihydro-4H-thieno[2,3-c]pyridin-7-one Dissolve 2-bromo-6-(3-methoxy-4-triisopropylsilanyloxy-phenyl)-5,6-dihydro-4H-thieno[2,3-c]pyridin-7-one (2.87 g, 5.46 mmol) in dimethoxyethane (28 mL) followed by addition of EtOH (4 mL) and water (8 mL). Add 4-chlorophenylboronic acid (1.28 g, 8.19 mmol) followed by 2M Na$_2$CO$_3$ (4 mL, 8.19 mmol). Allow dry argon gas to bubble through the reaction mixture for 15-20 min. Add Pd(PPh$_3$)$_4$ (315 mg, 0.27 mmol) and then warm to 90° C. under an argon atmosphere. After 3 h, filter the reaction through Celite® and elute with CH$_2$Cl$_2$. Concentrate and purify via silica gel chromatography using a 0-25% gradient of EtOAc/hexanes to give 2.37 g (80% yield) of the desired product. MS/ES m/z ($^{35}Cl$) 542.1 [M+H]$^-$.

Prepare the intermediates in the table below by essentially following the procedures as described in Preparation 41, using p-tolylboronic acid and 4-cylcopropoxyphenylboronic acid (prepared as described in Olofsson, K. et al, WO 2005123673).

| Prep | Chemical Name | MS/ES (m/z) |
|---|---|---|
| 42 | 6-(3-Methoxy-4-triisopropylsilanyloxy-phenyl)-2-p-tolyl-5,6-dihydro-4H-thieno[2,3-c]pyridin-7-one | 522.1 [M + H]$^+$ |
| 43* | 2-(4-Cyclopropoxy-phenyl)-6-(3-methoxy-4-triisopropylsilanyloxy-phenyl)-5,6-dihydro-4H-thieno[2,3-c]pyridin-7-one | 546.0 [M + H]$^+$ |

*Variations: DME/EtOH/2M Na$_2$CO$_3$ (no water). Microwave at 100° C. for 3 h. Workup with CH$_2$Cl$_2$ and 1 N NaOH.

Preparation 44

2-(4-Chloro-phenyl)-6-(4-hydroxy-3-methoxy-phenyl)-5,6-dihydro-4H-thieno[2,3-c]pyridin-7-one Dissolve 2-(4-chloro-phenyl)-6-(3-methoxy-4-triisopropylsilanyloxy-phenyl)-5,6-dihydro-4H-thieno[2,3-c]pyridin-7-one (1.68 g, 3.1 mmol) in THF (20 mL) and add 1.0 M solution of tetrabutyl ammonium fluoride in THF (3.1 mL, 3.1 mmol). Stir at RT for 1 h. Slowly add 1N HCl until pH is approximately 1. A precipitate begins to form. Allow to sit at RT for 2-3 h. Filter the resulting solid to yield 850 mg (71% yield) of the desired product. MS/ES m/z ($^{35}$Cl) 386.0 [M+H]$^+$.

Prepare the intermediates in the table below by essentially following the procedure as described for Preparation 44.

| Prep | Chemical Name | MS/ES (m/z) |
|---|---|---|
| 45 | 6-(4-Hydroxy-3-methoxy-phenyl)-2-p-tolyl-5,6-dihydro-4H-thieno[2,3-c]pyridin-7-one | 366.0 [M + H]$^+$ |
| 46 | 2-Bromo-6-(4-hydroxy-3-methoxy-phenyl)-5,6-dihydro-4H-thieno[2,3-c]pyridin-7-one | ($^{79}$Br) 353.9 [M + H]$^+$ |
| 47 | 2-(4-Cyclopropoxy-phenyl)-6-(4-hydroxy-3-methoxy-phenyl)-5,6-dihydro-4H-thieno[2,3-c]pyridin-7-one | 408.0 [M + H]$^+$ |

Example 9

2-(4-Chloro-phenyl)-6-[3-methoxy-4-(2-pyrrolidin-1-yl-ethoxy)-phenyl]-5,6-dihydro-4H-thieno[2,3-c]pyridin-7-one, hydrochloride

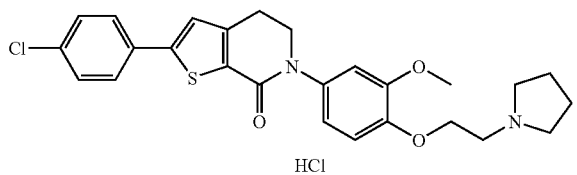

HCl

Cool a slurry of DMF (8 mL) and of 2-(4-chloro-phenyl)-6-(4-hydroxy-3-methoxy-phenyl)-5,6-dihydro-4H-thieno[2,3-c]pyridin-7-one (850 mg, 2.21 mmol) to 0° C. Add NaH (97 mg, 2.43 mmol) and stir 2 min. In a separatory funnel, make the free base of 1-(2-chloro-ethyl)-pyrrolidine hydrochloride by washing a slurry of the commercially available salt (500 mg) in CH$_2$Cl$_2$ (50 mL) with 1N NaOH (50 mL). Combine the organic layers and wash with brine (50 mL). Dry over Na$_2$SO$_4$ and concentrate to give 1-(2-chloro-ethyl)-pyrrolidine. Add the free base (391 mg, 2.94 mmol) to the reaction and warm to 60° C. overnight. Pour the reaction into a separatory funnel containing 1 N NaOH (100 mL). Extract with CH$_2$Cl$_2$ (2×100 mL). Wash the combined organic layers with brine (100 mL). Purify part of this material via silica gel chromatography using a 0-7% (2 N NH$_3$ in MeOH)/CHCl$_3$ gradient to give 330 mg (30% yield) of the pure freebase which is identical to Example 8. MS/ES m/z 483.0 [M+H]$^+$.

Alternatively, convert the product to the hydrochloride salt by dissolving the free base in CH$_2$Cl$_2$ (approximately 10 mg/mL), and adding 2.0 M HCl in diethyl ether (1.5 equivalents). Either concentrate the solution or precipitate with diethyl ether and then filter to provide 493 mg (43% yield) of the hydrochloride salt. MS/ES m/z ($^{35}$Cl) 483.0 [M+H]$^+$.

Prepare the compounds in the table below, Example 10 and Preparation 48, by essentially following the alkylation procedures as described in Example 9 using the appropriate phenol. Prepare Example 10 using N-(2-chloroethyl)morpholine hydrochloride in place of 1-(2-chloro-ethyl)-pyrrolidine hydrochloride.

| Example or Prep | Chemical Name | MS (ES) (m/z) |
|---|---|---|
| 10 | 2-(4-Chloro-phenyl)-6-[3-methoxy-4-(2-morpholin-4-yl-ethoxy)-phenyl]-5,6-dihydro-4H-thieno[2,3-c]pyridin-7-one, hydrochloride | ($^{35}$Cl) 499.0 [M + H]$^+$ |
| Prep 48 | 2-Bromo-6-[3-methoxy-4-(2-pyrrolidin-1-yl-ethoxy)-phenyl]-5,6-dihydro-4H-thieno[2,3-c]pyridin-7-one | ($^{79}$Br) 451.0 [M + H]$^+$ |

Example 11

2-(4-Chloro-phenyl)-6-[3-methoxy-4-(2-pyrrolidin-1-yl-ethoxy)-phenyl]-3-methyl-5,6-dihydro-4H-thieno[2,3-c]pyridin-7-one Prepare the titled compound by essentially following procedures as described in Preparation 17, using 5-(4-chloro-phenyl)-3-(2-hydroxy-ethyl)-4-methyl-thiophene-2-carboxylic acid [3-methoxy-4-(2-pyrrolidin-1-yl-ethoxy)-phenyl]-amide. ES/MS m/z ($^{35}$Cl) 497.0 [M+H]$^+$.

Example 12

2-(4-Cyclopropoxy-phenyl)-6-[3-methoxy-4-(2-pyrrolidin-1-yl-ethoxy)-phenyl]-5,6-dihydro-4H-thieno[2,3-c]pyridin-7-one hydrochloride Make the free base of 2-chloroethylpyrrolidine by adding the hydrochloride salt (84 mg, 0.49 mmol) to a separatory funnel containing 1 N NaOH (75 mL) and CH$_2$Cl$_2$ (75 mL). Wash the organic layer with brine then dry over Na$_2$SO$_4$ and concentrate. In a separate microwave vessel, mix 2-(4-cyclopropoxy-phenyl)-6-(4-hydroxy-3-methoxy-phenyl)-5,6-dihydro-4H-thieno[2,3-c]pyridin-7-one (100 mg, 0.24 mmol) in DMF (1 mL). Warm the mixture slightly with a heat gun until the phenol is in solution. Add powdered K$_2$CO$_3$ (68 mg, 0.49 mmol). Stir 5-10 min at RT and then add the chloride mentioned above as a solution in DMF (500 µL). Cap the vessel and heat under microwave irradiation to 110° C. for 2 h. Load the reaction directly onto a silica gel plug and purify

Example 13

2-(4-Fluoro-phenyl)-6-[3-methoxy-4-(2-pyrrolidin-1-yl-ethoxy)-phenyl]-5,6-dihydro-4H-thieno[2,3-c]pyridin-7-one, hydrochloride

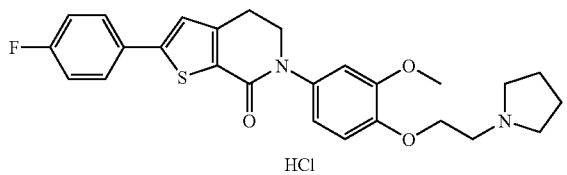

HCl

Dissolve 2-bromo-6-[3-methoxy-4-(2-pyrrolidin-1-yl-ethoxy)-phenyl]-5,6-dihydro-4H-thieno[2,3-c]pyridin-7-one (156 mg, 0.35 mmol) in a mixture of dimethoxyethane:EtOH:water, 7:2:1 (2 mL). Add 4-fluorophenyl boronic acid (63 mg, 0.45 mL) followed by 2 M $Na_2CO_3$ (225 μL, 0.45 mmol). Bubble dry argon gas through the reaction for 2-3 min and then add $Pd(PPh_3)_4$ (20 mg, 0.18 mmol). Seal the reaction and treat with microwave irradiation at 100° C. for 40 min. Load the reaction mixture directly onto a silica plug and purify using chromatography with a gradient of 0-10% (2N $NH_3$ in MeOH)/$CHCl_3$ to give 139 mg (85%) of the desired product as the free base. Prepare the HCl salt by dissolving the free base in $CH_2Cl_2$ (approx 0.1-0.3 M). Add 1.5 eq of a 4.0 M HCl in dioxane solution. Isolate the salt by either precipitating with diethyl ether and filtering the solid product or by simply concentrating the $CH_2Cl_2$ solution. MS/ES m/z 467.0 $[M+H]^+$.

Prepare the compounds in the table below, essentially as described in Example 13, using the appropriate boronic acid and 2-bromo-6-[3-methoxy-4-(2-pyrrolidin-1-yl-ethoxy)-phenyl]-5,6-dihydro-4H-thieno[2,3-c]pyridin-7-one.

| Example | Chemical Name | MS (ES) (m/z) |
|---|---|---|
| 14 | 6-[3-Methoxy-4-(2-pyrrolidin-1-yl-ethoxy)-phenyl]-2-(4-trifluoromethoxy-phenyl)-5,6-dihydro-4H-thieno[2,3-c]pyridin-7-one, hydrochloride | 533.0 $[M + H]^+$ |
| 15 | 2-(2,4-Dimethoxy-phenyl)-6-[3-methoxy-4-(2-pyrrolidin-1-yl-ethoxy)-phenyl]-5,6-dihydro-4H-thieno[2,3-c]pyridin-7-one, hydrochloride | 509.0 $[M + H]^+$ |
| 16 | 6-[3-Methoxy-4-(2-pyrrolidin-1-yl-ethoxy)-phenyl]-2-(4-trifluoromethyl-phenyl)-5,6-dihydro-4H-thieno[2,3-c]pyridin-7-one, hydrochloride | 517.0 $[M + H]^+$ |

Preparation 49

Trifluoro-methanesulfonic acid 2-methoxy-4-[2-(4-methoxy-phenyl)-7-oxo-4,7-dihydro-5H-thieno[2,3-c]pyridin-6-yl]-phenyl ester Dissolve 6-(4-hydroxy-3-methoxy-phenyl)-2-(4-methoxy-phenyl)-5,6-dihydro-4H-thieno[2,3-c]pyridin-7-one (0.486 g, 1.28 mmol) in pyridine (5 mL). Add trifluoromethanesulfonic anhydride (0.26 mL, 1.53 mmol) and stir the reaction at RT overnight. Remove the excess reagent and solvent in vacuo. Dissolve the resulting residue in $CH_2Cl_2$ (50 mL). Wash with saturated $CuSO_4$ (2×30 mL) and dry over $Na_2SO_4$. Filter and concentrate to give 0.649 g (100%) of the title compound. LC-MS/ES m/z 514.0 $[M+H]^+$.

Preparation 50

2-Methoxy-4-[2-(4-methoxy-phenyl)-7-oxo-4,7-dihydro-5H-thieno[2,3-c]pyridin-6-yl]-benzoic acid methyl ester Combine palladium acetate (0.015 g, 0.067 mmol), 1,4-bis(diphenylphosphino)butane (DPPB) (0.035 g, 0.080 mmol), trifluoro-methansulfonic acid 2-methoxy-4-[2-(4-methoxy-phenyl)-7-oxo-4,7-dihydro-5H-thieno[2,3-c]pyridin-6-yl]-phenyl ester (0.352 g, 0.685 mmol), dry methanol (10 mL, 0.249 mmol), dry triethylamine (0.50 mL, 3.5 mmol) and dry acetonitrile (15 mL) in a Parr pressure reactor equipped with a teflon coated stir bar. Purge the reaction vessel with nitrogen (4×) and with carbon monoxide (4×). Pressurize with carbon monoxide (100 psig, 690 KPa), seal, and agitate at 100° C. for 6 h while maintaining the carbon monoxide pressure at 100 psig. Allow the reaction to cool to ambient temperature and vent the carbon monoxide from the reaction vessel. Filter the reaction mixture through silica gel, wash with EtOAc (100 mL), and concentrate. Purify the crude material by chromatography, eluting with 50% EtOAc/hexanes to give 0.227 g (78%) of the title compound. MS/ES m/z 424.0 $[M+H]^+$.

Preparation 51

2-Methoxy-4-[2-(4-methoxy-phenyl)-7-oxo-4,7-dihydro-5H-thieno[2,3-c]pyridin-6-yl]-benzoic acid Dissolve 2-methoxy-4-[2-(4-methoxy-phenyl)-7-oxo-4,7-dihydro-5H-thieno[2,3-c]pyridin-6-yl]-benzoic acid methyl ester (0.2274 g, 0.54 mmol) in dioxane (10 mL) and add lithium hydroxide monohydrate (124 mg, 2.69 mmol) followed by water (5 mL). Stir the reaction at RT overnight, dilute with water (10 mL), and acidify with 1 N HCl. Collect the solid by filtration and wash with water (2×10 mL) and $Et_2O$ (2×10 mL). Dry the solid in a vacuum oven to give 0.145 g (66%). LC-MS/ES m/z 410.3 $[M+H]^+$.

Preparation 52

4-[2-(4-Chloro-phenyl)-7-oxo-4,7-dihydro-5H-thieno[2,3-c]pyridin-6-yl]-2-methoxy-benzoic acid Suspend 4-[2-(4-chloro-phenyl)-7-oxo-4,7-dihydro-5H-thieno[2,3-c]pyridin-6-yl]-2-methoxy-benzoic acid methyl ester (0.4 g, 0.94 mmol) in methanol (5 mL) and tetrahydrofuran (5 mL) and add 1 N NaOH (1.13 mL, 1.13 mmol). Heat the mixture at reflux for 16 h, cool to RT, and concentrate in vacuo. Suspend the residue in water (25 mL) and acidify with 10% sodium bisulfate. Extract the mixture with ethyl acetate (4×20 mL) to give a suspension in the organic portion. Filter the solid and dry in vacuo to give 0.19 g (49%) of the title compound. Concentrate the filtrate in vacuo to give 0.09 g (23%) more of the title compound. MS/ES m/z ($^{35}$Cl) 414.0 $[M+H]^+$.

Example 17

2-Methoxy-4-[2-(4-methoxy-phenyl)-7-oxo-4,7-dihydro-5H-thieno[2,3-c]pyridin-6-yl]-N-(2-pyrrolidin-1-yl-ethyl)-benzamide Suspend 2-methoxy-4-[2-(4-methoxy-phenyl)-7-oxo-4,7-dihydro-5H-thieno[2,3-c]pyridin-6-yl]-benzoic acid (0.1451 g, 0.35 mmol) in DMF (5 mL) and add 2-pyrrolidin-1-yl-ethylamine (45 mg, 0.39 mmol), EDCI (81 mg, 0.42 mmol), HOBt (57 mg, 0.42 mmol) and Et$_3$N (0.15 mL, 1.06 mmol). Stir the reaction at RT overnight. Dilute with EtOAc (100 mL), wash with water (2×30 mL), and dry over Na$_2$SO$_4$. Purify the crude material by silica gel chromatography, eluting with 2% NH$_3$—H$_2$O, 50% CH$_3$OH/EtOAc to give 9 mg (5%) of the title compound. LC-MS/ES m/z 506.2 [M+H]$^+$.

Example 18

4-[2-(4-Chloro-phenyl)-7-oxo-4,7-dihydro-5H-thieno[2,3-c]pyridin-6-yl]-2-methoxy-N-(2-morpholin-4-yl-ethyl)-benzamide, hydrochloride Heat a solution of 4-[2-(4-chloro-phenyl)-7-oxo-4,7-dihydro-5H-thieno[2,3-c]pyridin-6-yl]-2-methoxy-benzoic acid (0.10 g, 0.24 mmol) in thionyl chloride (1 mL) at reflux for one hour. Cool and concentrate the reaction in vacuo. Dissolve the residue in dichloromethane (0.5 mL) and add to a 0° C. solution of 4-(2-aminoethyl)morpholine (0.038 g, 0.29 mmol) and triethylamine (0.029 g, 0.29 mmol) in dichloromethane (0.5 mL). Stir the reaction at RT for 16 h. Wash the reaction with water (2 mL) and back extract the aqueous portion with dichloromethane (2×2 mL). Dry the combined organics (Na$_2$SO$_4$), filter, and concentrate in vacuo. Purify the material by silica gel chromatography, eluting with a gradient of dichloromethane to 5% 2 M ammonia in methanol/dichloromethane to give 0.085 g of the free amine. Dissolve the amine in dichloromethane (0.5 mL) and add 1 N HCl in ethanol (0.16 mL). Add diethyl ether (2 mL), filter the resulting solid, and dry in vacuo at 80° C. to give 0.08 g (59%) of the title compound. MS/ES m/z ($^{35}$Cl) 526.2 [M+H]$^+$.

Example 19

4-[2-(4-Chloro-phenyl)-7-oxo-4,7-dihydro-5H-thieno[2,3-c]pyridin-6-yl]-2-methoxy-N-(2-pyrrolidinl-yl-ethyl)-benzamide hydrochloride

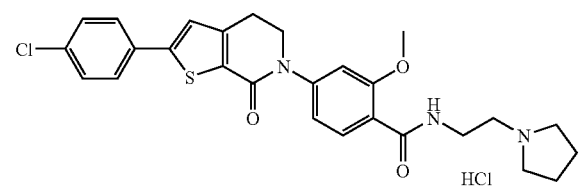

Add 2.0 M trimethylaluminum in toluene (0.26 mL, 0.53 mmol) to a solution of 1-(2-aminoethyl)pyrrolidine (0.042 g, 0.37 mmol) in toluene (7 mL) and stir the mixture for min. Add a suspension of 4-[2-(4-chloro-phenyl)-7-oxo-4,7-dihydro-5H-thieno[2,3-c]pyridin-6-yl]-2-methoxy-benzoic acid methyl ester (0.15 g, 0.35 mmol) in toluene (2 mL) and heat the reaction at 100° C. for 3 h. Cool the reaction to room temperature and slowly quench with water until no foaming is observed. Dilute the mixture with 1 N NaOH and extract with ethyl acetate (3×10 mL). Dry the combined organic portions (Na$_2$SO$_4$), filter and concentrate in vacuo to afford the free amine (63 mg). Dissolve the amine in dichloromethane (0.5 mL) and add 1 N hydrogen chloride in ethanol (0.117 mL). Add diethyl ether (5 mL), filter and dry the resulting white solid in vacuo to give 0.053 g (28%) of the title compound. MS/ES m/z ($^{37}$Cl) 511.3 [M+].

Prepare the compounds in the table below, Examples 20, 21 and Preparations 53, 54, by following the procedures as essentially described for Example 19, using the appropriate ester and amine.

| Example | Chemical Name | LC-MS/ES (m/z) |
|---|---|---|
| 20 | 4-[2-(4-Fluoro-phenyl)-7-oxo-4,7-dihydro-5H-thieno[2,3-c]pyridin-6-yl]-2-methoxy-N-(2-pyrrolidin1-yl-ethyl)-benzamide, hydrochloride | 494.0 [M + H]$^+$ |
| 21 | 4-[2-(4-Trifluoromethoxy-phenyl)-7-oxo-4,7-dihydro-5H-thieno[2,3-c]pyridin-6-yl]-2-methoxy-N-(2-pyrrolidin1-yl-ethyl)-benzamide, hydrochloride | 560.0 [M + H]$^+$ |
| Prep 53** | (±)-4-[2-(4-Chloro-phenyl)-7-oxo-4,7-dihydro-5H-thieno[2,3-c]pyridin-6-yl]-2-methoxy-benzoylamino}-methyl)-morpholine-4-carboxylic acid tert-butyl ester | ($^{37}$Cl) 613.3 [M+] |
| Prep 54** | 4-{4-[2-(4-Chloro-phenyl)-7-oxo-4,7-dihydro-5H-thieno[2,3-c]pyridin-6-yl]-2-methoxy-benzoylamino}-piperidine-1-carboxylic acid tert-butyl ester | ($^{37}$Cl) 597.3 [M+] |

**Purified by silica gel chromatography eluting with a gradient of 0% to 75% or 80% EtOAc/hexanes.

Example 22

(±)-4-[2-(4-Chloro-phenyl)-7-oxo-4,7-dihydro-5H-thieno[2,3-c]pyridin-6-yl]-2-methoxy-N-morpholin-2-ylmethyl-benzamide, hydrochloride Stir a solution of 4-[2-(4-chloro-phenyl)-7-oxo-4,7-dihydro-5H-thieno[2,3-c]pyridin-6-yl]-2-methoxy-benzoylamino}-methyl)-morpholine-4-carboxylic acid tert-butyl ester (0.20 g, 0.33 mmol) in 4 M HCl in 1,4-dioxane (3 mL) at RT for 2 h. Add diethyl ether (5 mL), filter and dry in vacuo at 80° C. to give 0.153 g (85%) of the title compound. MS/ES m/z ($^{37}$Cl) 513.0 [M+].

Example 23

4-[2-(4-Chloro-phenyl)-7-oxo-4,7-dihydro-5H-thieno[2,3-c]pyridin-6-yl]-2-methoxy-N-piperidin-4-yl benzamide, hydrochloride Prepare the titled compound by following the procedure as essentially described for Example 22, using 4-{4-[2-(4-chloro-phenyl)-7-oxo-4,7-dihydro-5H-thieno[2,3-c]pyridin-6-yl]-2-methoxy-benzoylamino}-piperidine-1-carboxylic acid tert-butyl ester to obtain 0.122 g (76%) of product. MS/ES m/z ($^{37}$Cl) 497.0 [M+].

Example 24

2-Chloro-4-[2-(4-chloro-phenyl)-7-oxo-4,7-dihydro-5H-thieno[2,3-c]pyridin-6-yl]-N-(2-pyrrolidin-1-yl-ethyl)-benzamide, hydrochloride Add indium(III) chloride (0.046 g, 0.093 mmol) to a suspension of 2-chloro-4-[2-(4-chloro-phenyl)-7-oxo-4,7-dihydro-5H-thieno[2,3-c]pyridin-6-yl]-benzoic acid methyl ester (0.2 g, 0.46 mmol) in 1-(2-aminoethyl)pyrrolidine (0.9 mL, 7.1 mmol), and heat the mixture at 120° C. for 16 h. Cool to RT and dilute with water (10 mL). Extract the mixture with dichloromethane (3×10 mL). Dry the combined organics (Na$_2$SO$_4$), filter, and concentrate in vacuo. Purify the residue by silica gel chromatography, eluting with dichloromethane to 6% 2 M ammonia in methanol/dichloromethane to give 71 mg (30%) of the free amine. Dissolve the free amine in chloroform (0.5 mL) and add 1 N HCl in ethanol (0.138 mL). Dilute the solution with diethyl ether (5 mL), filter and dry the resulting white solid in vacuo at 80° C. to give 0.06 g (24%) of the title compound. MS/ES m/z ($^{35}$Cl$^{35}$Cl) 514.0 [M+H]$^+$.

Preparation 55

1-(2-methoxy-4-nitro-phenyl)-4-methyl-piperazine

Heat 1-chloro-2-methoxy-4-nitro-benzene (1.0 g, 5.33 mmol) and 1-methylpiperazine (1.33 g, 13.30 mmol) at 100° C. in a sealed tube for 16 h. Cool the mixture to room temperature and partition between dichloromethane (50 mL) and water (50 mL). Separate the organic portion and extract the aqueous portion with dichlorormethane (2×20 mL). Dry the combined organic portions (Na$_2$SO$_4$), filter and concentrate in vacuo to give 1.05 g (78%) of the title compound. MS/ES m/z 252.0 [M+H]$^+$.

Preparation 56

3-methoxy-4-(methyl-piperazin-1-yl)-phenylamine

Dissolve 1-(2-methoxy-4-nitro-phenyl)-4-methyl-piperazine (1.05 g, 4.18 mmol) in ethyl acetate (50 mL) and add 10% Pd/C (0.20 g). Hydrogenate the slurry at room temperature under a hydrogen filled balloon for 16 h. Filter the slurry through a pad of Celite® and rinse with ethyl acetate. Concentrate the filtrate in vacuo to give a reddish solid (0.66 g, 71% yield). MS/ES m/z 220.0 (M+1)$^+$.

Preparation 57

4-(2-Fluoro-4-nitro-phenyl)-piperazine-1-carboxylic acid tert-butyl ester

Dissolve 3,4-difluoronitrobenzene (2.0 g, 12.6 mmol) in acetonitrile (35 mL) and add piperazine-1-carboxylic acid tert-butyl ester (4.7 g, 25.2 mmol). Heat the mixture at reflux for 16 h. Cool the mixture to room temperature and concentrate in vacuo. Partition the residue between dichloromethane (75 mL) and water (75 mL), separate the organic portion and extract the aqueous portion with dichloromethane (2×25 mL). Combine the organics and dry (Na$_2$SO$_4$), filter, and concentrate in vacuo to give 2.83 g (72%) of the title compound. MS/ES m/z 270.2 [M-tertBu+H]$^+$.

Preparation 58

(S)-3-(2-Methoxy-4-nitro-phenoxy)-pyrrolidine-1-carboxylic acid tert-butyl ester Dissolve N-tert-butyl-(S)-3-hydroxypyrrolidine (35 g, 187 mmol) in dry DMF (500 ml) at 0° C. for 10 min. Add NaH (60% in mineral oil, 8.98 g, 224 mmol) portionwise. Allow the reaction to stir for 30 min at 0° C. and then add a solution of 2-chloro-5-nitroanisole (35.1 g, 187 mmol) in DMF (120 ml) dropwise via cannula under a nitrogen atmosphere. Allow the reaction to stir overnight at 130° C. Remove the organic solvent via reduced pressure. Dilute in water (1 L) and extract with EtOAc (3×200 ml). Wash the combined organic portions with water (2×200 ml), dry (Na$_2$SO$_4$), filter and concentrate in vacuo. Purify the resulting residue by silica gel chromatography using a solvent gradient of 0-50% EtOAc in hexanes. Collect the desired material and triturate with Et$_2$O overnight. Filter the solid via vacuum filteration to give 37 g (58%) of the title compound. $^1$H NMR (CDCl$_3$) δ 1.43 (s, 9H), 2.27-2.05 (m, 2H), 3.69-3.48 (m, 4H), 4.98 (m, 1H), 3.89 (s, 3H), 6.85-6.83 (d, J=9.2 Hz, 1H), 7.73-7.72 (d, J=2.6 Hz, 1H), 7.85-7.83 (br d, J=9.0 Hz, 2H).

Preparation 59

(R)-3-(2-Methoxy-4-nitro-phenoxy)-piperidine-1-carboxylic acid tert-butyl ester

Prepare the title compound by essentially following the procedure as described for Preparation 58, using (R)-3-hydroxy-piperidine-1-carboxylic acid tert-butyl ester (35.0 g, 174 mmol) to give 47.0 g (76%) of the title compound. MS/ES m/z 297.2 [M-tBu+H]$^+$.

Preparation 60

3-(2-Methoxy-4-nitro-phenoxy)-azetidine-1-carboxylic acid tert-butyl ester

Dissolve 1-fluoro-2-methoxy-4-nitro-benzene (118 g, 689 mmol) and 3-hydroxy-azetidine-1-carboxylic acid tert-butyl ester (125 g, 724 mmol) in THF (800 mL) and cool to 0° C. To the above solution under a nitrogen atmosphere, add dropwise a 1M solution of tBuOK (1 L, solution in THF). After addition is complete, stir the dark brown solution for 30 min at 0° C., then dilute with water (1 L) over a 10 min period. Stir the mixture for 5 min, then extract with MTBE twice. Combine the organic solutions and wash with brine (2×700 mL), then dry and concentrate. Dry the solid in vacuo at 45° C. for 20 h to obtain 216 g (95%) of the title compounds as a yellow solid. $^1$H NMR (300 MHz, CDCl$_3$) δ1.42 (s, 9H), 3.80 (s, 3H), 4.04 (m, 2H), 4.18 (m, 2H), 4.76 (m, 1H), 6.17 (dd, 1H, J=2.4, 8.5), 6.30 (d, 1H, J=2.6), 6.47 (d, 1H, J=8.5).

Prepare the following compounds using essentially the same procedures as described in Preparation 60, using the appropriate alcohol.

| Prep | Chemical Name | MS/ES (m/z) |
|------|---------------|-------------|
| 61 | (R)-3-(2-Methoxy-4-nitro-phenoxy)-pyrrolidine-1-carboxylic acid tert-butyl ester | 283.0 [M − tBu + H]$^+$ |
| 62 | 4-(2-Methoxy-4-nitro-phenoxy)-piperidine-1-carboxylic acid tert-butyl ester | 297.0 [M − tBu + H]$^+$ |
| 63 | (S)-3-(2-Methoxy-4-nitro-phenoxy)-piperidine-1-carboxylic acid tert-butyl ester | 297.2 [M − tBu + H]$^+$ |
| 64 | 3-(2-Fluoro-4-nitro-phenoxy)-azetidine-1-carboxylic acid tert-butyl ester | 257.0 [M − tBu + H]$^+$ |

Preparation 65

N-(2-Methoxy-4-nitro-phenyl)-2-pyrrolidin-1-yl-acetamide

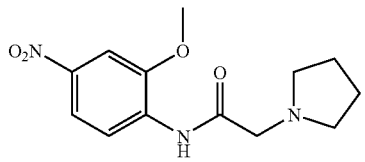

Dissolve 2-methoxy-4-nitro-phenylamine (1.0 g, 5.95 mmol), pyrrolidin-1-yl-acetic acid hydrochloride (0.99 g, 5.95 mmol) and N,N-diisopropylethylamine (1.08 mL, 6.55 mmol) in N,N-dimethylformamide (20 mL) and add O-(7-azabenzotriazol-1-yl)-N,N,N',N'-tetramethyluronium hexafluorophosphate (2.49 g, 6.55 mmol). Stir the mixture at room temperature for 16 h. Dilute the mixture with water (50 mL) and extract with dichloromethane (3×25 mL). Dry the combined organics (Na$_2$SO$_4$), filter, and concentrate in vacuo. Purify by chromatography (0% to 4% MeOH/CH$_2$Cl$_2$) to afford 0.77 g (46%) of the title compound. MS/ES m/z 280.0 [M+H]$^+$.

Preparation 66

(R)-1-(2-Methoxy-4-nitro-phenyl)-3-triisopropylsilanyloxy-pyrrolidine

Combine 1-chloro-2-methoxy-4-nitro-benzene (10 g, 53.3 mmol) and (R)-3-pyrrolidinol (9.3 g, 106.6 mmol). Heat the mixture to 100° C. overnight. Cool the mixture and dissolve in CH$_2$Cl$_2$ (200 mL) and wash with 1 N NaOH (100 mL). Wash the extract with brine (3×50 mL). Dry the organic layer with Na$_2$SO$_4$, filter, and concentrate to give the intermediate pyrrolidinol as a crude dark reddish wet solid (12.17 g, 95%). MS (ES$^+$) 239.1 (M+1)$^+$.

Dissolve the crude (R)-1-(2-methoxy-4-nitro-phenyl)-pyrrolidin-3-ol (10.9 g, 45.5 mmol) in dry pyridine (50 mL) and chill to 0° C. Add chloro-triisopropyl-silane (19.8 mL, 91 mmol) dropwise and then heat to 80° C. overnight. Remove the pyridine via reduced pressure and then wash the crude material with NaHSO$_3$ solution and extract with EtOAc (3×100 mL). Combine the organic solutions, then dry and concentrate to give the crude product. Purify over a silica plug with hexanes (300 mL) and flush with 10% EtOAc in hexanes (800 mL) to give the title compound as a reddish oil (17.85 g, 99%). MS/ES m/z 395.2 [M+H]$^+$.

Preparation 67

(S)-1-(2-Methoxy-4-nitro-phenyl)-3-triisopropylsilanyloxy-pyrrolidine

Prepare the titled compound by essentially following the procedures as described in Preparation 56 using (S)-3-pyrrolidinol. MS/ES m/z 395.3 [M+H]$^+$.

Preparation 68

(S)-3-(4-amino-2-methoxy-phenoxy)-pyrrolidine-1-carboxylic acid tert-butyl ester Dissolve (S)-3-(2-methoxy-4-nitro-phenoxy)-pyrrolidine-1-carboxylic acid tert-butyl ester (2.0 g, 5.91 mmol) in ethyl acetate (50 mL) and add 10% Pd/C (0.20 g). Hydrogenate the slurry at room temperature under a hydrogen filled balloon for 16 h. Filter the slurry through a pad of Celite® and rinse with ethyl acetate. Concentrate the filtrate in vacuo to give a reddish solid (1.82 g, 100% yield). MS/ES m/z 253.0 [M−t-butyl+H]$^+$.

Prepare the following compounds using essentially the same procedure as described in Preparation 68 except using methanol as the solvent for Preparations 72 and 73 and using 5% Pd/C for Preparation 72.

| Prep | Chemical Name | MS/ES (m/z) |
|------|---------------|-------------|
| 69 | 4-(4-Amino-2-fluoro-phenyl)-piperazine-1-carboxylic acid tert-butyl ester | 296.0 [M + H]$^+$ |
| 70 | (R)-3-(4-Amino-2-methoxy-phenoxy)-piperidine-1-carboxylic acid tert-butyl ester | 345.0 [M + Na]$^+$ |
| 71 | N-(4-Amino-2-methoxy-phenyl)-2-pyrrolidin-1-yl-acetamide | 250.0 [M + H]$^+$ |
| 72 | 3-(4-Amino-2-methoxy-phenoxy)-azetidine-1-carboxylic acid tert-butyl ester | 239.0 [M − tBu + H]$^+$ |
| 73* | 3-(4-Amino-2-fluoro-phenoxy)-azetidine-1-carboxylic acid tert-butyl ester | 227.0 [M − tBu + H]$^+$ |

-continued

| Prep | Chemical Name | MS/ES (m/z) |
|---|---|---|
| 74 | (R)-3-(4-Amino-2-methoxy-phenoxy)-pyrrolidine-1-carboxylic acid tert-butyl ester | 253.0 [M − tBu + H]$^-$ |
| 75 | 4-(4-Amino-2-methoxy-phenoxy)-piperidine-1-carboxylic acid tert-butyl ester | 267.0 [M − tBu + H]$^+$ |
| 76 | (S)-3-(4-Amino-2-methoxy-phenoxy)-piperidine-1-carboxylic acid tert-butyl ester | 267.3 [M − tBu + H]$^-$ |
| 77 | (R)-3-Methoxy-4-(3-triisopropylsilanyloxy-pyrrolidin-1-yl)-phenylamine | 365.2 [M + H]$^+$ |
| 78 | (S)-3-Methoxy-4-(3-triisopropylsilanyloxy-pyrrolidin-1-yl)-phenylamine | 365.0 [M + H]$^+$ |

*Purify by silica gel chromatography using 50% EtOAc/hexane.

Preparation 79

5-(4-Chloro-phenyl)-3-(2-hydroxy-ethyl)-thiophene-2-carboxylic acid [3-methoxy-4-(2-pyrrolidin-1-yl-acetamide Dissolve N-(4-amino-2-methoxy-phenyl)-2-pyrrolidin-1-yl-acetamide (1.32 mmol, 330 mg) in toluene (14 mL) and add 2M trimethylaluminum in toluene (1.32 mmol, 661 µL) via syringe. After 5 min, add 2-(4-chloro-phenyl)-4,5-dihydro-thieno[2,3-c]pyran-7-one (944 µmol, 250 mg) and heat the reaction at 80° C. for 17 h. Cool the reaction to room temperature and slowly quench with 5 mL of saturated aqueous Rochelle's salt. Dilute the mixture with 10 mL of water and extract with dichloromethane (4×10 mL). Dry the combined organics over Na$_2$SO$_4$, filter, and concentrate to dryness. Purify by chromatography (0% to 5% MeOH/CH$_2$Cl$_2$) to afford 321 mg (66%) of the title compound. MS/ES m/z ($^{35}$Cl) 513.0 [M+].

Preparation 80

4-Bromo-2-methoxy-phenylamine

Add dropwise a solution of bromine (0.83 mL, 16.2 mmol) in CH$_2$Cl$_2$ (130 mL) to a solution of 2-methoxy-phenylamine (2.0 g, 16.2 mmol) in dichloromethane (100 mL) at 0° C. over a period of 45 min. Stir the mixture at 0° C. to RT overnight. Wash the mixture with water, dry over Na$_2$SO$_4$, filter, and concentrate. Purify the crude material by flash chromatography eluting with 10% EtOAc/hexane to give 1.95 g (59%) of the title compound. GC m/z ($^{81}$Br) 203 [M+].

Preparation 81

N-(4-Bromo-2-methoxy-phenyl)-2-chloro-acetamide

Add chloroacetic anhydride (1.78 g, 10.1 mmol) to a solution of 4-bromo-2-methoxy-phenylamine (1.94 g, 9.60 mmol) in CH$_2$Cl$_2$ (48 mL) at 0° C. Stir the mixture at RT for 2 h. Dilute the mixture with CH$_2$Cl$_2$, then wash with 1N NaOH, brine, and water. Dry the organic layer over Na$_2$SO$_4$, filter, and concentrate to give 2.6 g (97%) of the title compound. LC-ES/MS m/z ($^{81}$Br, $^{35}$Cl) 280.0 [M+H]$^+$.

Preparation 82

N-(4-Bromo-2-methoxy-phenyl)-2-pyrrolidin-1-yl-acetamide

Add pyrrolidine (7.5 mL, 90 mmol) to a mixture of N-(4-bromo-2-methoxy-phenyl)-2-chloro-acetamide (5.0 g, 18 mmol) and potassium carbonate (4.96 g, 36 mmol) in acetonitrile (180 mL). Heat the mixture at 80° C. for 4 h. Cool the mixture to RT and filter with CH$_2$Cl$_2$ (300 mL). Wash the filtrate with brine (400 mL), back extract the aqueous twice with CH$_2$Cl$_2$ (300 mL). Wash the combined organic layer with water (250 mL). Dry the organic portion over Na$_2$SO$_4$, filter, and concentrate. Dry the resulting solid on house vacuum overnight to give 5.6 g (99%) of the title compound. LC-ES/MS m/z ($^{81}$Br) 314.0 [M+].

Example 25

N-{4-[2-(4-Chloro-phenyl)-7-oxo-4,7-dihydro-5H-thieno[2,3-c]pyridin-6-yl]-2-methoxy-phenyl}-2-pyrrolidin-1-yl-acetamide hydrochloride

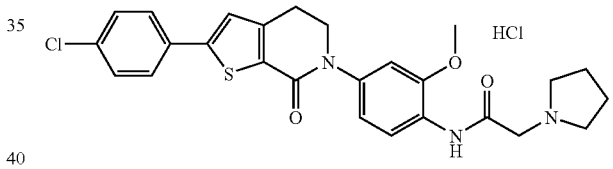

Dissolve 5-(4-chloro-phenyl)-3-(2-hydroxy-ethyl)-thiophene-2-carboxylic acid [3-methoxy-4-(2-pyrrolidin-1-yl-acetylamino)-phenyl]-amide (623 µmol, 320 mg) and tri-n-butylphosphine (934 µmol, 233 µL) in tetrahydrofuran (5 mL) then add dropwise via syringe diisopropyl azodicarboxylate (934 µmol, 185 µL). Stir the mixture at room temperature for 4 h. Dilute the mixture with 15 mL of Et$_2$O, filter the resulting solid, and dry under vacuum at 60° C. to afford 195 mg (63%) of N-{4-[2-(4-chloro-phenyl)-7-oxo-4,7-dihydro-5H-thieno[2,3-c]pyridin-6-yl]-2-methoxy-phenyl}-2-pyrrolidin-1-yl-acetamide. Prepare the hydrochloride salt of the free base using 1N HCl in ethanol. Dilute the salt solution in ether then filter off the product. Dry in vacuo to obtain the title compound. MS/ES m/z ($^{35}$Cl) 496.2 [M+H]$^+$.

Example 25

Alternate procedure

Combine 2-(4-chloro-phenyl)-5,6-dihydro-4H-thieno[2,3-c]pyridin-7-one (2.0 g, 7.58 mmol), N-(4-bromo-2-methoxy-phenyl)-2-pyrrolidin-1-yl-acetamide (2.85 g, 9.10 mmol), Cs$_2$CO$_3$ (4.94 g, 15.2 mmol), 1,4-dioxane (76 mL), and CuI (0.578 g, 3.03 mmol). Purge the mixture with nitrogen for 10 min. Add sym-dimethylethylene diamine (0.53 g, 6.01 mmol) and heat the mixture at 100° C. overnight. Cool the mixture to RT, dilute with CH$_2$Cl$_2$, and wash twice with a solution of 5% NH$_4$OH/H$_2$O. Dry the organic layer over Na$_2$SO$_4$, filter, and concentrate. Filter the crude with H$_2$O and Et$_2$O. Prepare the HCl salt by dissolving the solid with CH$_2$Cl$_2$. Add 1 eq of 1 M HCl/ether, allow the solution to stir for 15 min, and concentrate to give 2.92 g (72%) of the title compound. LC-ES/MS m/z ($^{35}$Cl) 496.2 [M+H]$^+$.

Example 26

N-{4-[2-(4-Chloro-phenyl)-7-oxo-7H-thieno[2,3-c]pyridin-6-yl]-2-methoxy-phenyl}-2-pyrrolidin-1-yl-acetamide, hydrochloride

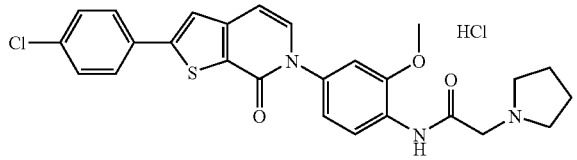

Combine 2-(4-chloro-phenyl)-6H-thieno[2,3-c]pyridin-7-one (1.8 g, 6.88 mmol), N-(4-bromo-2-methoxy-phenyl)-2-pyrrolidin-1-yl-acetamide (2.58 g, 8.25 mmol), Cs$_2$CO$_3$ (4.48 g, 13.8 mmol), 1,4-dioxane (69 mL), and CuI (0.520 g, 2.75 mmol). Purge the mixture with nitrogen for 10 min. Add sym-dimethylethylene diamine (0.49 g, 5.50 mmol) and heat the mixture at 100° C. overnight. Cool the mixture to RT, dilute with CH$_2$Cl$_2$, and wash twice with a solution of 5% NH$_4$OH/H$_2$O (2×). Dry the organic layer over Na$_2$SO$_4$, filter, and concentrate. Filter the crude with H$_2$O and Et$_2$O. Purify the crude material by chromatography using a gradient of 20-50% acetone in hexane. Prepare the HCl salt by dissolving the solid with CH$_2$Cl$_2$. Add 1 eq of 1 M HCl/ether, allow the solution to stir for 15 min, and concentrate to give 1.95 g (53%) of the title compound. LC-ES/MS m/z ($^{35}$Cl) 494.0 [M+H]$^+$.

Preparation 83

2-(4-Chloro-phenyl)-4-methyl-thiophene

Prepare the title compound by essentially following the procedure as described in Preparation 21, using 1-chloro-4-iodo-benzene and 4-methylthiophene-2-boronic acid to give 4.34 g (95%) of product. $^1$H NMR (400 MHz, CDCl$_3$) δ 2.28 (d, J=0.9 Hz, 3H), 6.87 (pent, J=1.3 Hz, 1H), 7.10 (d, J=1.3 Hz, 1H), 7.33 (d, J=8.6 Hz, 2H), 7.50 (d, J=8.6 Hz, 2H).

Preparation 84

5-(4-Chloro-phenyl)-3-methyl-thiophene-2-carboxylic acid

Dissolve 2-(4-chloro-phenyl)-4-methyl-thiophene (0.53 g, 1.85 mmol) in THF (25 mL) and cool to −78° C. Add t-BuLi (1.7 M, 2.3 mL, 3.88 mmol) dropwise. Stir the solution at −78° C. for 20 min. Cannulate the solution into a flask containing powdered dry ice (10 g). Stir the reaction and allow to warm to RT. Quench the reaction with saturated NH$_4$Cl (10 mL), dilute with water (40 mL), and extract with EtOAc (2×50 mL). Dry the combined organic layers over Na$_2$SO$_4$, filter, and concentrate. Purify the crude material by washing with hexane (2×20 mL) to give 0.35 g (74%) of the title compound. LC-MS/ES m/z ($^{35}$Cl) 251.0 [M−H]$^−$.

Preparation 85

5-(4-Chloro-phenyl)-3-methyl-thiophene-2-carboxylic acid (3-methoxy-4-triisopropylsilanyloxy-phenyl)-amide

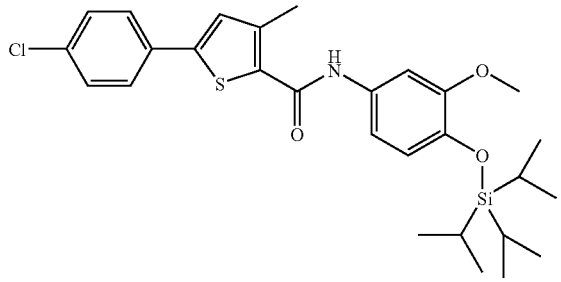

Suspend 5-(4-chloro-phenyl)-3-methyl-thiophene-2-carboxylic acid (2.13 g, 8.44 mmol) in CH$_2$Cl$_2$ (15 mL) and treat with oxalyl chloride (1.5 mL, 16.87 mmol), followed by the addition of DMF (2 drops). Stir the mixture at RT for 2 h and then evaporate down in vacuo. Dissolve the resulting solid material in CH$_2$Cl$_2$ (30 mL) and cool to 0° C. Add 3-methoxy-4-triisopropylsilanyloxy-phenylamine (2.62 g, 8.86 mmol) and Et$_3$N (1.8 mL, 12.66 mol) in CH$_2$Cl$_2$ (10 mL) dropwise at 0° C. Stir the reaction at 0° C. for 10 min and at RT for 30 min. Dilute the reaction with CH$_2$Cl$_2$ (100 mL), wash with 0.1 M HCl (2×30 mL), 1.0 M NaOH (2×30 mL), dry over Na$_2$SO$_4$, filter, and concentrate. Purify the crude material by chromatography, eluting with 20% EtOAc/hexane to give 3.53 g (79%) of the title compound. LC-MS/ES m/z ($^{37}$Cl) 531.2 [M+].

Prepare the compounds in the table below, by essentially following the procedures as described in Preparation 85, using 5-(4-chloro-phenyl)-3-methyl-thiophene-2-carboxylic acid and the appropriate phenylamine.

| Prep | Chemical Name | MS/ES (m/z) |
|---|---|---|
| 86* | 5-(4-Chloro-phenyl)-3-methyl-thiophene-2-carboxylic acid [3-methoxy-4-(4-methyl-piperazin-1-yl)-phenyl]-amide | ($^{35}$Cl) 456.3 (M + H)$^+$ |
| 87* | (S)-3-(4-{[5-(4-chloro-phenyl)-3-methyl-thiophene-2-carbonyl]-amino}-2-methoxy-phenoxy)-pyrrolidine-1-carboxylic acid tert-butyl ester | ($^{37}$Cl) 487.0 (M − tBu + H)$^+$ |
| 88 | (R)-3-(4-{[5-(4-Chloro-phenyl)-3-methyl-thiophene-2-carbonyl]-amino}-2-methoxy-phenoxy)-piperidine-1-carboxylic acid tert-butyl ester | ($^{35}$Cl) 555.0 [M − H]$^−$ |
| 89 | 4-(4-{[5-(4-Chloro-phenyl)-3-methyl-thiophene-2-carbonyl]-amino}-2-fluoro-phenyl)-piperazine-1-carboxylic acid tert-butyl ester | ($^{35}$Cl) 530.0 [M + H]$^+$ |

-continued

| Prep | Chemical Name | MS/ES (m/z) |
|---|---|---|
| 90 | 4-(4-{[5-(4-Chloro-phenyl)-3-methyl-thiophene-2-carbonyl]-amino}-2-methoxy-phenoxy)-piperidine-1-carboxylic acid tert-butyl ester | LC-MS/ES m/z ($^{35}$Cl) 555.3 [M− |
| 91 | (S)-3-(4-{[5-(4-Chloro-phenyl)-3-methyl-thiophene-2-carbonyl]-amino}-2-methoxy-phenoxy)-piperidine-1-carboxylic acid tert-butyl ester | LC-MS/ES m/z ($^{35}$Cl) 555.0 [M− |
| 92 | (R)-3-(4-{[5-(4-Chloro-phenyl)-3-methyl-thiophene-2-carbonyl]-amino}-2-methoxy-phenoxy)-pyrrolidine-1-carboxylic acid tert-butyl ester | LC-MS/ES m/z ($^{35}$Cl) 541.0 [M− |
| 93 | 5-(4-Chloro-phenyl)-3-methyl-thiophene-2-carboxylic acid [3-methoxy-4-((R)-3-triisopropylsilanyloxy-pyrrolidin-1-yl)-phenyl]-amide | ($^{35}$Cl) 599.3 [M + H]$^+$ |
| 94 | 5-(4-Chloro-phenyl)-3-methyl-thiophene-2-carboxylic acid [3-methoxy-4-((S)-3-triisopropylsilanyloxy-pyrrolidin-1-yl)-phenyl]-amide | ($^{35}$Cl) 599.3 [M + H]$^+$ |

*Stir coupling 16 h at RT. Workup with 10% sodium bisulfate. Purify by silica gel chromatography using 0-5% gradient of (2 N NH$_3$ in MeOH)/CHCl$_3$.

Preparation 95

3-(4-{[5-(4-Chloro-phenyl)-3-(2-hydroxy-ethyl)-thiophene-2-carbonyl]-amino}-2-methoxy-phenoxy)-azetidine-1-carboxylic acid tert-butyl ester Dissolve 3-(4-amino-2-methoxy-phenoxy)-azetidine-1-carboxylic acid tert-butyl ester (2.27 mmol, 667 mg) in toluene (35 mL) and add 2M trimethylaluminum in toluene (2.27 mmol 1.13 mL). Add to this solution 2-(4-chloro-phenyl)-4,5-dihydro-thieno[2,3-c]pyran-7-one (1.51 mmol 400 mg) and heat the reaction at 80° C. for 5 h. Cool the reaction to room temperature and slowly quench with 10 mL of saturated Rochelle's salt. Stir the mixture for 10 min and dilute with 40 mL of water. Separate the organic portion and extract the aqueous portion with EtOAc (2×25 mL). Dry the combined organics over Na$_2$SO$_4$, filter, and concentrate to dryness. Purify by chromatography (hexane to 70% ethyl acetate/hexane) to afford 840 mg (99%) of the title compound. MS/ES m/z ($^{35}$Cl) 557.0 [M−H]$^−$.

Preparation 96

2-(4-Chloro-phenyl)-6-(3-methoxy-4-triisopropylsilanyloxy-phenyl)-3 a,7a-dihydro-6H-thieno[2,3-c]pyridin-7-one

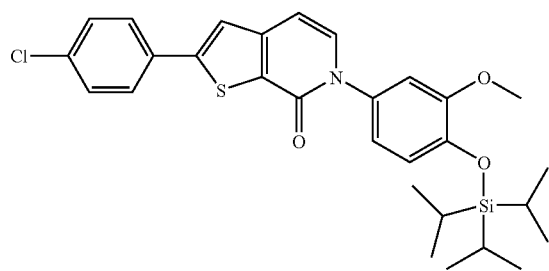

Dissolve 5-(4-chloro-phenyl)-3-methyl-thiophene-2-carboxylic acid (3-methoxy-4-triisopropyl-silanyloxy-phenyl)-amide (3.53 g, 6.66 mmol) in THF (70 mL). Cool the solution to −78° C. Add t-BuLi (1.7 M, 8.6 mL, 14.65 mmol) dropwise while maintaining the internal temperature below −70° C. Stir the resulting blue solution at −78° C. for 15 min. Add DMF (5 mL) dropwise and stir the reaction at −78° C. for 10 min and then warm gradually to 0° C. and stir at 0° C. for 30 min. Quench with 1.0 M HCl (20 mL) at 0° C. with stirring for 5 min and then at RT for 15 min. Dilute with water (50 mL) and EtOAc (100 mL). Separate the organic layer, wash with 0.1 M HCl (2×50 mL), dry over Na$_2$SO$_4$, filter, and concentrate. Purify the crude material by chromatography, eluting with 20% EtOAc/hexane to give 2.86 g (80%) of the title compound. LC-MS/ES m/z ($^{35}$Cl) 540.0 [M+H]$^+$.

Prepare the examples in the table below, by essentially following the procedures as described in Preparation 96, using the appropriate amide precursor. To make the HCl salt dissolve the free amine in CH$_2$Cl$_2$, add 1 M HCl in EtOH (1 eq), stir, precipitate with diethyl ether, and filter.

| Examples | Chemical Name | MS (m/z) |
|---|---|---|
| 27 | 2-(4-Chloro-phenyl)-6-[3-methoxy-4-(4-methyl-piperazin-1-yl)-phenyl]-6H-thieno[2,3-c]pyridine-7-one, hydrochloride | ($^{35}$Cl) 466.3 (M + H)$^+$ |
| 28 | (S)-2-(4-Chloro-phenyl)-6-[3-methoxy-4-(pyrrolidin-3-yloxy)-phenyl]-6H-thieno[2,3-c]pyridin-7-one, hydrochloride | ($^{35}$Cl) 453.0 (M + H)$^+$ |

Example 29

2-(4-Chloro-phenyl)-6-[4-((R)-3-hydroxy-pyrrolidin-1-yl)-3-methoxy-phenyl]-6H-thieno[2,3-c]pyridin-7-one hydrochloride Dissolve 5-(4-chloro-phenyl)-3-methyl-thiophene-2-carboxylic acid [3-methoxy-4-((R)-3-triisopropylsilanyloxy-pyrrolidin-1-yl)-phenyl]-amide (0.573 g, 0.958 mmol) in THF (10 mL). Cool the mixture to −78° C. under argon. Add t-BuLi (1.2 mL, 2.11 mmol) dropwise and stir at −78° C. for 20 min. Add DMF (1.5 mL) and stir at −78° C. for 10 min, then warm gradually to 0° C. Quench the mixture with saturated NH₄Cl (10 mL) then dilute with EtOAc (100 mL) and wash with water (2×30 mL). Dry the solution with Na₂SO₄, filter, and concentrate. Suspend the resulting crude material in toluene (40 mL) and treat with p-toluenesulfonic acid-H₂O (0.45 g, 2.37 mmol). Reflux the mixture using a Dean-Stark trap. Dilute the mixture with EtOAc (150 mL) and wash with saturated NaHCO₃ (2×50 mL). Dry the solution with Na₂SO₄, filter, and concentrate. Purify the crude material by chromatography, eluting with 100% EtOAc to give 0.144 g (33%) of 2-(4-chloro-phenyl)-6-[4-((R)-3-hydroxy-pyrrolidin-1-yl)-3-methoxy-phenyl]-6H-thieno[2,3-c]pyridin-7-one.

Prepare the HCl salt by dissolving the free base in dichloromethane and MeOH. Treat the mixture with 1.0 M HCl in EtOH. Add Et₂O, filter, and wash with Et₂O. Dry in a vacuum oven at RT for 2 days to give 0.123 g (79%) of the title compound. LC-MS/ES m/z (³⁵Cl) 453.0 [M+H]⁺.

Preparation 97

2-(4-Chloro-phenyl)-6-[4-((S)-3-hydroxy-pyrrolidin-1-yl)-3-methoxy-phenyl]-6H-thieno[2,3-c]pyridin-7-one Prepare the title compound by essentially following the procedures as described in Example 28, using 5-(4-chloro-phenyl)-3-methyl-thiophene-2-carboxylic acid [3-methoxy-4-((S)-3-triisopropylsilanyloxy-pyrrolidin-1-yl)-phenyl]-amide, except do not prepare the hydrochloride salt (0.338 g, 26%). LC-MS/ES m/z (³⁵Cl) 452.8 [M+H]⁺.

Preparation 98

3-{4-[2-(4-Chloro-phenyl)-7-oxo-4,7-dihydro-5H-thieno[2,3-c]pyridin-6-yl]-2-methoxy-phenoxy}-azetidine-1-carboxylic acid tert-butyl ester Dissolve 3-(4-{[5-(4-chloro-phenyl)-3-(2-hydroxy-ethyl)-thiophene-2-carbonyl]-amino}-2-methoxy-phenoxy)-azetidine-1-carboxylic acid tert-butyl ester (840 mg, 1.50 mmol) and tri-n-butylphosphine (2.25 mmol, 562 μL) in tetrahydrofuran (15 mL) and add slowly dropwise diisopropyl azodicarboxylate (2.25 mmol, 447 μL). Stir the mixture overnight and concentrate in vacuo. Triturate the residue with Et₂O, filter, and dry in vacuo to afford 550 mg (62%) of the title compound as a white solid. LC-MS/ES m/z (³⁵Cl) 441.0 [M-tBuCO₂+H]⁺.

Example 30

2-(4-Chloro-phenyl)-6-[3-methoxy-4-((R)-piperidin-3-yloxy)-phenyl]-6H-thieno[2,3-c]pyridine-7-one, hydrochloride

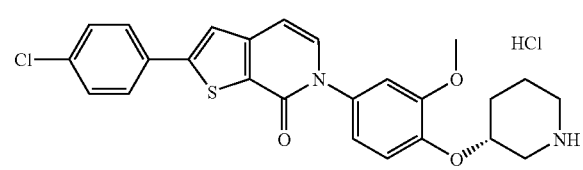

Dissolve (R)-3-(4-{[5-(4-chloro-phenyl)-3-methyl-thiophene-2-carbonyl]-amino}-2-methoxy-phenoxy)-piperidine-1-carboxylic acid tert-butyl ester (2.63 g, 4.72 mmol) in tetrahydrofuran (35 mL) under argon and cool to −78° C. Add 1.7 M tert-butyllithium in pentane (6.1 mL, 10.38 mmol) while maintaining the temperature below −70° C. Stir the solution at −78° C. for 20 min. Add N,N-dimethylformamide (2.68 mL, 34.46 mmol) to the solution maintaining temperature below −70° C. Remove the cooling bath after 5 min and stir the reaction for 30 min. Quench the reaction with saturated aqueous ammonium chloride (20 mL). Dilute the mixture with water (10 mL) and extract with ethyl acetate (3×30 mL). Dry the combined organics (Na₂SO₄), filter, and concentrate in vacuo. Dissolve the residue in 30 mL of ethyl acetate and add p-toluenesulfonic acid (1.41 g, 7.08 mmol). Heat the mixture at reflux overnight, cool, and dilute with water (30 mL). Make the mixture basic with 1 N NaOH and extract with ethyl acetate (3×40 mL). Dry the combined organics (Na₂SO₄), filter, and concentrate in vacuo. Purify by chromatography (dichloromethane to 7% 2 M ammonia in methanol/dichloromethane) to afford 0.77 g (35%) of 2-(4-chloro-phenyl)-6-[3-methoxy-4-((R)-piperidin-3-yloxy)-phenyl]-6H-thieno[2,3-c]pyridine-7-one.

Dissolve the free base (305 mg, 0.65 mmol) in dichloromethane (3 mL) and add 1 N hydrogen chloride in ethanol (0.65 mL, 0.65 mmol). Add diethyl ether (10 mL) of the resulting suspension. Filter the resulting solid and dry to afford 269 mg (82%) of the title compound. LC-MS/ES m/z (³⁵Cl) 467.3 [M+H]⁺.

Prepare the compounds in the table by essentially following the procedures as described in Example 30 using the appropriate amide.

| Examples | Chemical Name | MS (m/z) |
| --- | --- | --- |
| 31 | 2-(4-Chloro-phenyl)-6-(3-fluoro-4-piperazin-1-yl-phenyl)-6H-thieno[2,3-c]pyridin-7-one, hydrochloride | (³⁵Cl) 440.0 [M + H]⁺ |
| 32 | 2-(4-Chloro-phenyl)-6-[3-methoxy-4-((S)-piperidin-3-yloxy)-phenyl]-6H-thieno[2,3-c]pyridin-7-one, hydrochloride | LC-MS/ES m/z (³⁵Cl) 467.0 [M + H]⁺ |
| 33 | 2-(4-Chloro-phenyl)-6-[3-methoxy-4-((R)-pyrrolidin-3-yloxy)-phenyl]-6H-thieno[2,3-c]pyridin-7-one, hydrochloride | LC-MS/ES m/z (³⁵Cl) 453.0 [M + H]⁺ |
| 34 | 2-(4-Chloro-phenyl)-6-[3-methoxy-4-(piperidin-4-yloxy)-phenyl]-6H-thieno[2,3-c]pyridin-7-one, hydrochloride | LC-MS/ES m/z (³⁵Cl) 467.0 [M + H]⁺ |

Example 35

6-[4-(Azetidin-3-yloxy)-3-methoxy-phenyl]-2-(4-chloro-phenyl)-5,6-dihydro-4H-thieno[2,3-c]pyridin-7-one hydrochloride Dissolve 3-{4-[2-(4-chloro-phenyl)-7-oxo-4,7-dihydro-5H-thieno[2,3-c]pyridin-6-yl]-2-methoxy-phenoxy}-azetidine-1-carboxylic acid tert-butyl ester (924 μmol, 500 mg) in dichloromethane (10 mL), add trifluoroacetic acid (5 mL), and stir the reaction at room temperature for 2 h. Concentrate the material in vacuo and partition the residue between 1N NaOH (10 mL) and CH₂Cl₂ (15 mL). Separate the organic portion and extract the aqueous portion with CH₂Cl₂ (3×10 mL). Dry the combined organics over Na₂SO₄, filter, and concentrate to dryness to afford 320 mg of 6-[4-(azetidin-3-yloxy)-3-methoxy-phenyl]-2-(4-chloro-phenyl)-5,6-dihydro-4H-thieno[2,3-c]pyridin-7-one as a white solid.

Prepare the HCl salt by dissolving the residue in CH$_2$Cl$_2$ and adding HCl in ethanol. Add ether to the mixture then filter and dry the solid to obtain the title compound. LC-MS/ES m/z ($^{35}$Cl) 441.0 [M+H]$^+$.

Example 36

2-(4-Chloro-phenyl)-6-[3-methoxy-4-((R)-1-methyl-piperidin-3-yloxy)-phenyl]-6H-thieno[2,3-c]pyridin-7-one hydrochloride

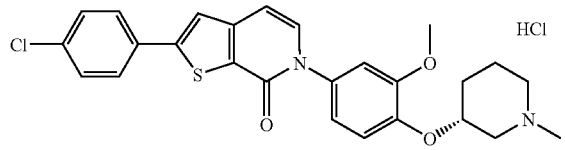

Stir a solution of 2-(4-chloro-phenyl)-6-[3-methoxy-4-((R)-piperidin-3-yloxy)-phenyl]-6H-thieno[2,3-c]pyridine-7-one (446 mg, 0.96 mmol), formaldehyde (0.38 mL, 37% aqueous solution), and acetic acid (0.22 mL, 3.84 mmol) in methanol (34 mL) at room temperature for 5 min. Add sodium cyanoborohydride (150 mg, 2.4 mmol) to this solution and stir the reaction for 2 h. Concentrate the mixture in vacuo and partition the residue between dichloromethane (20 mL) and saturated sodium bicarbonate (20 mL). Separate the organic portion and extract the aqueous portion with dichloromethane (2×10 mL). Dry the combined organics (Na$_2$SO$_4$), filter, and concentrate in vacuo. Purify by chromatography (dichloromethane to 5% 2 M ammonia in methanol/dichloromethane) to afford 158 mg (34%) of 2-(4-chloro-phenyl)-6-[3-methoxy-4-((R)-1-methyl-piperidin-3-yloxy)-phenyl]-6H-thieno[2,3-c]pyridin-7-one.

Prepare the HCl salt by dissolving the residue in CH$_2$Cl$_2$ and adding HCl in ethanol. Add ether to the mixture then filter and dry the solid to obtain the title compound. LC-MS/ES m/z ($^{35}$Cl) 481.0 [M+H]$^+$.

Prepare the compounds in the table below by essentially following the procedures as described in Example 36 using the appropriate amine.

| Examples | Chemical Name | MS/ES (m/z) |
|---|---|---|
| 37 | 2-(4-Chloro-phenyl)-6-[3-methoxy-4-((S)-1-methyl-piperidin-3-yloxy)-phenyl]-6H-thieno[2,3-c]pyridin-7-one, hydrochloride | ($^{35}$Cl) 481.2 [M + H]$^+$ |
| 38 | 2-(4-Chloro-phenyl)-6-[3-methoxy-4-(1-methyl-azetidin-3-yloxy)-phenyl]-5,6-dihydro-4H-thieno[2,3-c]pyridin-7-one, hydrochloride | ($^{35}$Cl) 455.0 [M + H]$^+$ |

Preparation 99

3-Bromo-5-(4-chloro-phenyl)-thiophene-2-carboxylic acid methyl ester

Suspend CuBr$_2$ (1.0 g, 4.44 mmol) and tert-butyl nitrite (0.66 mL, 5.55 mmol) in CH$_3$CN (15 mL) then stir at RT for 30 min. Add 3-amino-5-(4-chloro-phenyl)-thiophene-2-carboxylic acid methyl ester (1.0 g, 3.7 mmol) and warm the reaction to 70° C. for 4 h. Cool the reaction mixture to RT and pour into 20% HCl (200 mL) then extract with CH$_2$Cl$_2$ (200 mL). Wash the organic layer with 20% HCl then dry over sodium sulfate and concentrate. Purify the crude material by chromatography, eluting with 10% EtOAc/hexane to give 0.65 g (53%) of the title compound. LC-MS/ES m/z ($^{79}$Br) 332.0 [M+H]$^+$.

Preparation 100

5-(4-Chloro-phenyl)-3-trimethylsilanylethynyl-thiophene-2-carboxylic acid methyl ester React 3-bromo-5-(4-chloro-phenyl)-thiophene-2-carboxylic acid methyl ester (0.66 g, 2.0 mmol) with (trimethylsilyl)acetylene (216 mg, 2.2 mmol), Pd(PPh$_3$)$_2$Cl$_2$ (140 mg, 0.20 mmol), CuI (38.2 mg, 0.20 mmol), PPh$_3$ (210 mg, 0.80 mmol) and diisopropyl amine (3.3 mL, 30 mmol) in DMF (1.0 mL) at 120° C. for 30 min in a microwave reactor. Treat the mixture with Et$_2$O (15 mL), filter, pour into 0.1 M HCl (15 mL), and extract with Et$_2$O (3×10 mL). Wash the combined organic layers with saturated NaHCO$_3$ (20 mL) and water (20 mL). Purify the crude material by chromatography, eluting with 30% CH$_2$Cl$_2$/hexane to give 400 mg (57%) of the title compound. LC-MS/ES m/z ($^{35}$Cl) 349.0 [M+H]$^+$.

Preparation 101

3-{4-[2-(4-Chloro-phenyl)-7-oxo-7H-thieno[2,3-c]pyridin-6-yl]-2-fluoro-phenoxy}-azetidine-1-carboxylic acid tert-butyl ester Add 2.0 M Al(CH$_3$)$_3$ (1.28 mL, 2.56 mmol) to a suspension of 5-(4-chloro-phenyl)-3-trimethylsilanylethynyl-thiophene-2-carboxylic acid methyl ester (0.851 g, 2.44 mmol) and 3-(4-amino-2-fluoro-phenoxy)-azetidine-1-carboxylic acid tert-butyl ester (0.688 g, 2.44 mmol) in toluene (20 mL). Stir the reaction at 60° C. for 4 h. Cool the mixture to 0° C., quench with 2.0 M NaOH (5 mL) and water (20 mL) and then extract with CHCl$_3$ (3×50 mL). Dry with Na$_2$SO$_4$, filter, and concentrate. Dissolve the crude material in THF (50 mL), treat with 1.0 M TBAF (2.93 mL, 2.93 mmol) and stir at RT overnight. Dilute with EtOAc (100 mL), wash with water (3×40 mL), dry with Na$_2$SO$_4$, filter, and concentrate. Purify the crude material by chromatography, eluting with 5% CH$_3$OH/CHCl$_3$ to give 1.03 g (80%) of the title compound. LC-MS/ES m/z ($^{35}$Cl) 526.9 [M+H]$^+$.

Example 39

2-(4-Chloro-phenyl)-6-[3-fluoro-4-(1-methyl-azetidin-3-yloxy)-phenyl]-6H-thieno[2,3-c]pyridin-7-one hydrochloride Dissolve 3-{4-[2-(4-chloro-phenyl)-7-oxo-7H-thieno[2,3-c]pyridin-6-yl]-2-fluoro-phenoxy}-azetidine-1-carboxylic acid tert-butyl ester (0.491 g, 0.932 mmol) in CH$_2$Cl$_2$ (10 mL) and treat with TFA (3 mL), with stirring at RT for 2 h. Remove the excess reagent and solvent in vacuo. Dissolve the crude material in CH$_3$OH (15 mL), treat with formaldehyde (0.28 mL, 3.71 mmol, 37% aqueous solution), HOAc (0.21 mL, 3.71 mmol) and NaBH$_3$CN (0.233 g, 3.71 mmol). Stir the mixture at RT for 30 min followed by reflux for 4 h. Quench the mixture with saturated NH$_4$Cl solution (10 mL). Dilute with water (10 mL) and saturated NaHCO$_3$ (30 mL). Extract with EtOAc (3×50 mL). Dry the combined organic layers with Na$_2$SO$_4$, filter, and concentrate. Purify the crude material by chromatography, eluting with 1% Et$_3$N, 10% CH$_3$OH/CHCl$_3$ to give 2-(4-chloro-phenyl)-6-[3-fluoro-4-(1-methylazetidin-3-yloxy)-phenyl]-6H-thieno[2,3-c]pyridin-7-one (0.3012 g, 0.683 mmol, 74%). Dissolve the free base (0.152 g, 344.7 µmoles) in CH$_2$Cl$_2$ (5 mL) and CH$_3$OH (0.5 mL). Treat the mixture with 1.0 M HCl in EtOH (344.7 µmoles; 344.7 µL). Add Et$_2$O (50 mL), filter, and wash with Et$_2$O (2×20 mL). Dry in a vacuum oven at RT for 2 days to give 0.14 g (83%) of the title compound. LC-MS/ES m/z ($^{35}$Cl) 441.0 [M+H]$^+$.

Preparation 102

3-(4-{[5-(4-Chloro-phenyl)-3-trimethylsilanylethynyl-thiophene-2-carbonyl]-amino}-2-methoxy-phenoxy)-azetidine-1-carboxylic acid tert-butyl ester Dissolve 3-(4-amino-2-methoxy-phenoxy)-azetidine-1-carboxylic acid tert-butyl ester (320 mg, 1.09 mmol) in toluene (11 mL) and add 2 M trimethylaluminum (0.65 mL, 1.30 mmol, solution in toluene). Stir the solution at RT for 1 h and then add 5-(4-chloro-phenyl)-3-trimethylsilanylethynyl-thiophene-2-carboxylic acid methyl ester (380 mg, 1.09 mmol). Stir the solution at 50° C. overnight, then carefully quench with saturated Rochelle's salt solution. Stir the mixture for 1 h and then extract with CH$_2$Cl$_2$ (3×30 mL). Combine the organic solutions, dry, filter, and concentrate the filtrate. Purify the crude material by flash chromatography, using 8% MeOH (2 N NH$_3$) in CH$_2$Cl$_2$ as eluent, to give 425 mg (64%) of the title compound as a white solid. LC-MS/ES m/z ($^{35}$Cl) 555.0 [M−t-butyl+H]$^+$.

Preparation 103

3-{4-[2-(4-Chloro-phenyl)-7-oxo-7H-thieno[2,3-c]pyridin-6-yl]-2-methoxy-phenoxy}-azetidine-1-carboxylic acid tert-butyl ester Dissolve 3-(4-{[5-(4-chloro-phenyl)-3-trimethylsilanylethynyl-thiophene-2-carbonyl]-amino}-2-methoxy-phenoxy)-azetidine-1-carboxylic acid tert-butyl ester (420 mg, 0.69 mmol) in THF (11 mL) and add 1 M tetrabutylammonium fluoride (1.50 mL, 1.50 mmol, solution in THF). Stir the solution at RT overnight. Dilute the solution with EtOAc (100 mL) and wash with water (3×50 mL) and brine (50 mL). Dry the organic solution, filter, and concentrate the filtrate. Purify the crude material by flash chromatography, using a linear gradiant of 30-70% EtOAc/hexanes, to give 280 mg (75%) of the title compound. LC-MS/ES m/z ($^{35}$Cl) 483.0 [M−t-butyl+H]$^+$.

Preparation 104

6-[4-(Azetidin-3-yloxy)-3-methoxy-phenyl]-2-(4-chloro-phenyl)-6H-thieno[2,3-c]pyridin-7-one trifluoroacetate Dissolve 3-{4-[2-(4-chloro-phenyl)-7-oxo-7H-thieno[2,3-c]pyridin-6-yl]-2-methoxy-phenoxy}-azetidine-1-carboxylic acid tert-butyl ester (280 mg, 0.52 mmol) in trifluoroacetic acid (5 mL) and stir the solution at RT for 1 h. Concentrate the solution in vacuo and purify the crude material by flash chromatography, using 8% MeOH (2 N NH$_3$) in CH$_2$Cl$_2$ as eluent, to give 213 mg (93%) of the title compound. LC-MS/ES m/z ($^{35}$Cl) 439.0 [M+H]$^+$.

Example 40

2-(4-Chloro-phenyl)-6-[3-methoxy-4-(1-methyl-azetidin-3-yloxy)-phenyl]-6H-thieno[2,3-c]pyridin-7-one hydrochloride Mix 6-[4-(azetidin-3-yloxy)-3-methoxy-phenyl]-2-(4-chloro-phenyl)-6H-thieno[2,3-c]pyridin-7-one trifluoroacetic acid salt (210 mg, 0.48 mmol) with methanol (10 mL) and acetic acid (0.3 mL). Add a solution of formaldehyde (0.20 mL, 2.66 mmol, 37% aqueous solution) and stir the mixture for 15 min. Add sodium cyanoborohydride (110 mg, 1.75 mmol) and stir the mixture at RT overnight. Concentrate the mixture in vacuo and partition the crude material between saturated NaHCO$_3$ (25 mL) and CH$_2$Cl$_2$ (25 mL). Remove the organic solution and extract the aqueous phase with additional CH$_2$Cl$_2$ (2×25 mL). Combine the organic solutions and concentrate in vacuo. Purify the crude material by flash chromatography, using 5% MeOH (2N NH$_3$) in CH$_2$Cl$_2$ as eluent, to give 133 mg (61%) of 2-(4-chloro-phenyl)-6-[3-methoxy-4-(1-methyl-azetidin-3-yloxy)-phenyl]-6H-thieno[2,3-c]pyridin-7-one as a white solid.

Mix the free base (128 mg, 0.28 mmol) with methanol (3 mL) and add 4M HCl (0.1 mL, 0.4 mmol, solution in 1,4-dioxane) and CH$_2$Cl$_2$ (3 mL). Stir the solution at RT for 30 min and dilute with diethyl ether (15 mL). Stir the mixture at RT for 30 min, collect the white solid by filtration, and dry under vacuum to give 123 mg (89%) of the title compound. LC-MS/ES m/z ($^{35}$Cl) 453.0 [M+H]$^+$.

Preparation 105

2-(4-Chloro-phenyl)-6-(4-hydroxy-3-methoxy-phenyl)-3 a,7a-dihydro-6H-thieno[2,3-c]pyridin-7-one Dissolve 2-(4-chloro-phenyl)-6-(3-methoxy-4-triisopropylsilanyloxy-phenyl)-3a,7 a-dihydro-6H-thieno[2,3-c]pyridin-7-one (2.86 g, 5.29 mmol) in THF (55 mL), cool to 0° C., and treat with 1.0 M TBAF (5.8 mL, 5.8 mmol). Stir the reaction at 0° C. for 10 min and at RT for 2 h. Dilute the reaction with EtOAc (150 mL), wash with saturated NH$_4$Cl (100 mL), water (100 mL), and brine (100 mL). Dry the organic portion over Na$_2$SO$_4$, filter, and concentrate. Wash the resulting crude material with refluxing hexanes (2×40 mL) and dry in vacuo to give 1.95 g (96%) of the title compound. LC-MS/ES m/z ($^{35}$Cl) 384.0 [M−H]$^-$.

Example 41

2-(4-Chloro-phenyl)-6-[3-methoxy-4-(2-pyrrolidin-1-yl-ethoxy)-phenyl]-6H-thieno[2,3-c]pyridin-7-one, hydrochloride Suspend 2-(4-chloro-phenyl)-6-(4-hydroxy-3-methoxy-phenyl)-3 a,7a-dihydro-6H-thieno[2,3-c]pyridin-7-one (0.233 g, 0.61 mmol) in acetonitrile (12 mL). Add Cs$_2$CO$_3$ (0.40 g, 1.22 mol) and reflux for 1 h. Add a solution of 1-(2-chloro-ethyl)-pyrrolidine hydroloride salt (114 mg, 0.67 mmol) in acetonitrile (5 mL) dropwise over a period of 5 min.

Reflux the reaction for 2.5 h. Allow to cool to RT and dilute with EtOAc (50 mL). Wash with water (2×30 mL), dry over Na$_2$SO$_4$, filter, and concentrate. Purify the crude material by chromatography, eluting with 2% NH$_3$—H$_2$O, 50% CH$_3$OH/ EtOAc to give 0.164 g. Dissolve the material in CH$_2$Cl$_2$ (5 mL) and treat with 1.0 M HCl in EtOH (340 μL). Stir at RT for 5 min and concentrate to give 0.172 g, (59%) of the title compound. LC-MS/ES m/z ($^{37}$Cl) 482.0 [M+]. $^1$H NMR (DMSO-d$_6$) δ 1.82-1.96 (m, 2H), 1.98-2.12 (m, 2H), 3.08-3.23 (m, 2H), 3.58-3.70 (m, 4H), 3.82 (s, 3H), 4.04 (t, J=4.8 Hz, 2H), 6.82 (d, J=7.1 Hz, 1H), 7.02 (dd, J=8.3, 2.4 Hz, 1H), 7.17 (d, J=2.4 Hz, 1H), 7.19 (d, J=8.8 Hz, 1H), 7.56 (d, J=7.1 Hz, 1H), 7.58 (d, J=8.3 Hz, 2H), 7.84-7.89 (m, 3H), 10.69 (bs, 1H).

Example 42

2-(4-Chloro-phenyl)-6-[3-methoxy-4-(3-methyl-3H-imidazol-4-ylmethoxy)-phenyl]-6H-thieno[2,3-c]pyridin-7-one, hydrochloride Dissolve 2-(4-chloro-phenyl)-6-(4-hydroxy-3-methoxy-phenyl)-3a,7a-dihydro-6H-thieno[2,3-c]pyridin-7-one (0.271 g, 0.71 mmol) in NMP (10 mL) and treat with K$_2$CO$_3$ (0.39 g, 2.83 mmol), and 5-chloromethyl-1-methyl-1H-imidazole hydrochloride salt (123 mg, 0.74 mmol). Stir the mixture at 80° C. overnight. Dilute the reaction with EtOAc (100 mL), wash with water (3×25 mL), dry over Na$_2$SO$_4$, filter and concentrate. Purify the crude material by chromatography, eluting with 1% NH$_3$—H$_2$O, 30% CH$_3$OH/EtOAc to give 0.105 g. Dissolve the material in CHCl$_3$ (5 mL) and CH$_3$OH (2 mL). Add 1.0 M HCl in EtOH (213 μL) stir. Concentrate and dry in vacuo to give 0.104 g (28%) of the title compound. LC-MS/ES m/z ($^{37}$Cl) 479.0 [M+]. $^1$H NMR (DMSO-d$_6$) δ 3.79 (s, 3H), 3.92 (s, 3H), 5.30 (s, 2H), 6.83 (d, J=7.2 Hz, 1H), 7.03 (dd, J=8.3, 2.1 Hz, 1H), 7.17 (d, J=2.1 Hz, 1H), 7.30 (d, J=8.7 Hz, 1H), 7.5 (d, J=7.2 Hz, 1H), 7.58 (d, J=8.5 Hz, 2H), 7.83 (d, J=8.5 Hz, 2H), 7.88 (s, 3H), 9.07 (bs, 1H).

Preparation 106

Methanesulfonic acid (R)-1-{4-[2-(4-chloro-phenyl)-7-oxo-7H-thieno[2,3-c]pyridin-6-yl]-2-methoxy-phenyl}-pyrrolidin-3-yl ester Dissolve 2-(4-chloro-phenyl)-6-[4-((R)-3-hydroxy-pyrrolidin-1-yl)-3-methoxy-phenyl]-6H-thieno[2,3-c]pyridin-7-one (2.407 g, 5.34 mmol) in CH$_2$Cl$_2$ (50 mL) and add MsCl (0.46 mL, 5.87 mmol) and Et$_3$N (1.0 mL, 7.32 mmol). Stir the mixture at RT for one hour. Dilute the mixture with CH$_2$Cl$_2$ (50 mL) and wash with water (30 mL). Dry the solution with Na$_2$SO$_4$, filter, and concentrate. Purify the crude material by chromatography, eluting with 10% EtOAc/CH$_2$Cl$_2$ to give 1.05 g (37%) of the title compound. LC-MS/ES m/z ($^{35}$Cl) 531.8 [M+H]$^+$.

Preparation 107

Methanesulfonic acid (S)-1-{4-[2-(4-chloro-phenyl)-7-oxo-7H-thieno[2,3-c]pyridin-6-yl]-2-methoxy-phenyl}-pyrrolidin-3-yl ester Prepare the title compound by essentially following the procedures as described in Preparation 105 to obtain 0.397 g (100%). LC-MS/ES m/z ($^{35}$Cl) 531.8 [M+H]$^+$.

Example 43

2-(4-Chloro-phenyl)-6-[4-((S)-3-dimethylamino-pyrrolidin-1-yl)-3-methoxy-phenyl]-6H-thieno[2,3-c]pyridin-7-one hydrochloride

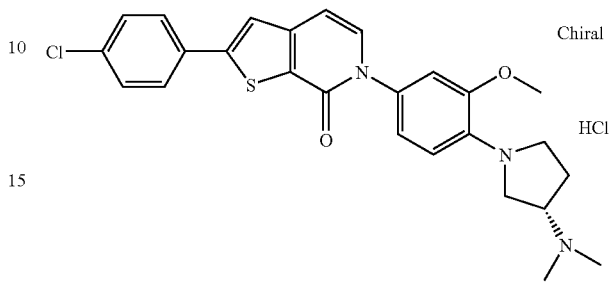

Dissolve methanesulfonic acid (R)-1-{4-[2-(4-chloro-phenyl)-7-oxo-7H-thieno[2,3-c]pyridin-6-yl]-2-methoxy-phenyl}-pyrrolidin-3-yl ester (0.504 g, 0.952 mmol) in 2 M dimethylamine in THF (10 mL). Stir the mixture at 75° C. overnight in a sealed pressure tube. Dilute the mixture with EtOAc (50 mL) and wash with saturated NaHCO$_3$ (2×20 mL) and brine (20 mL). Dry the solution with Na$_2$SO$_4$, filter, and concentrate. Purify the crude material by chromatograghy, eluting with 2% NH$_3$—H$_2$O/50% CH$_3$OH/EtOAc to give 0.293 g (64%) of 2-(4-chloro-phenyl)-6-[4-((S)-3-dimethylamino-pyrrolidin-1-yl)-3-methoxy-phenyl]-6H-thieno[2,3-c]pyridin-7-one.

Prepare the HCl salt by dissolving the free base in dichloromethane and MeOH. Treat the mixture with 1.0 M HCl in EtOH, add Et$_2$O, filter, and wash with Et$_2$O. Dry in a vacuum oven at RT for 2 days to give 0.249 g (79%) of the title compound. LC-MS/ES m/z ($^{35}$Cl) 480.2 [M+H]$^+$.

Prepare the compounds in the table below by essentially following the procedures as described in Example 43 using the corresponding mesylate and either methylamine or dimethylamine.

| Example | Chemical Name | LC-MS/ES (m/z) |
|---|---|---|
| 44 | 2-(4-Chloro-phenyl)-6-[3-methoxy-4-((S)-3-methylamino-pyrrolidin-1-yl)-phenyl]-6H-thieno[2,3-c]pyridin-7-one, hydrochloride | ($^{35}$Cl) 466.2 [M + H]$^+$ |
| 45 | 2-(4-Chloro-phenyl)-6-[4-((R)-3-dimethylamino-pyrrolidin-1-yl)-3-methoxy-phenyl]-6H-thieno[2,3-c]pyridin-7-one, hydrochloride | ($^{35}$Cl) 480.2 [M + H]$^+$. |

Preparation 108

(R)-5-Benzyloxymethyl-4-methyl-morpholin-3-one

Add triethylamine (7.0 mL, 50.6 mmol) to a RT slurry of (S)-2-amino-3-benzyloxy-propan-1-ol hydrochloride (5 g, 23.0 mmol) in CH$_2$Cl$_2$ (75 mL). Stir until all the solid dissolves and then cool to 0° C. Add chloroacetylchloride (2.0 mL, 25.3 mmol). Stir 1 h and add more TEA (960 μL, 6.9 mmol) and chloroacetylchloride (549 μL, 6.9 mmol) to consume all the starting amine with continued stirring for 2 h. Pour into a separatory funnel containing 1 N HCl (200 mL) and extract with CH$_2$Cl$_2$ (2×250 mL). Wash the combined organic extracts with brine (200 mL), dry over Na$_2$SO$_4$, and concentrate to give crude N—((S)-1-benzyloxymethyl-2-hydroxy-ethyl)-2-chloro-acetamide. Dissolve this intermediate in THF (75 mL), cool to 0° C., and treat with NaH (1.1 g, 27.6 mmol). Stir 6 h at 0° C. to form the NH morpholinone. Add additional NaH 1.1 g (27.6 mmol) followed by MeI (3.6 mL, 57.5 mmol). Stir at 0° C. for 30 min and then pour into a separatory funnel containing 0.1 M HCl (200 mL). Extract with EtOAc (2×250 mL). Wash the combined organic extracts with brine (200 mL), dry over Na$_2$SO$_4$, filter, and concentrate to give the crude methylated product. Purify via silica gel chromatography using a gradient of 0-100% EtOAc/hexanes to yield 1.3 g (24%, 3 steps) of the title compound. MS/ES m/z 236.1 [M+H]$^+$.

Preparation 109

(R)-5-Hydroxymethyl-4-methyl-morpholin-3-one

Prepare a slurry containing 10% Pd/C (137 mg) in MeOH (50 mL). Add a solution of (R)-5-benzyloxymethyl-4-methyl-morpholin-3-one (1.3 g, 5.5 mmol) in MeOH (100 mL). Pressurize with hydrogen gas (50 psi) and stir for 2 h. Filter the reaction through Celite® and elute with MeOH. Concentrate the filtrate to give 767 mg (96%) of the title compound. MS/ES m/z 146.1 [M+H]$^+$.

Preparation 110

Toluene-4-sulfonic acid (S)-4-methyl-5-oxo-morpholin-3-ylmethyl ester

Dissolve (R)-5-hydroxymethyl-4-methyl-morpholin-3-one (767 mg, 5.29 mmol) in pyridine (18 mL). Cool the reaction to 0° C., add 1.3 g (6.9 mmol) of p-toluenesulfonyl chloride (1.3 g, 6.9 mmol), and stir for 90 min. Pour into 1N HCl (50 mL) and extract with EtOAc (2×100 mL). Wash the combined organic layers with brine (50 mL), dry over Na$_2$SO$_4$, and concentrate to give the crude product. Purify via silica gel chromatography using a 0-100% EtOAc/hexanes gradient to yield 684 mg (43%) of the title compound. MS/ES m/z 300.0 [M+H]$^+$.

Example 46

2-(4-Chloro-phenyl)-6-[3-methoxy-4-((S)-4-methyl-5-oxo-morpholin-3-ylmethoxy)-phenyl]-6H-thieno[2,3-c]pyridin-7-one Add Cs$_2$CO$_3$ (339 mg, 1.04 mmol) to a slurry of 2-(4-chloro-phenyl)-6-(4-hydroxy-3-methoxy-phenyl)-6H-thieno[2,3-c]pyridin-7-one, (Preparation 47) (200 mg, 0.522 mmol), in 10 mL CH$_3$CN (10 mL). Stir 1 h and then add toluene-4-sulfonic acid (S)-4-methyl-5-oxo-morpholin-3-ylmethyl ester (172 mg, 0.57 mmol). Warm to reflux overnight. Cool to RT, pour into 1 M NaOH (100 mL) and extract with CH$_2$Cl$_2$ (3×100 mL). Wash the combined organic extracts with brine (100 mL). Purify via silica gel chromatography using 0-5-20% (2 N NH$_3$ in MeOH)/CHCl$_3$ to give 41 mg of product that is 86% pure. Recrystallize from CH$_2$Cl$_2$/hexanes to give 28 mg of the desired product in good purity. MS/ES m/z ($^{35}$Cl) 511.0 [M+H]$^+$.

Preparation 111

1,4-Dibromo-2-methoxy-benzene

Add dropwise potassium tert-butoxide (118.2 ml, 118.2 mmol, 1 M in hexane) to a solution of 1,4-dibromo-2-fluorobenzene (25.0 g, 98.5 mmol) in THF (492 mL) and MeOH (40 mL, 984.7 mmol) at RT. Heat the mixture at 70° C. overnight. Quench the mixture with water (50 mL), dilute with Et$_2$O (400 mL), wash once with saturated NH$_4$Cl (300 mL) and back extract the aqueous with Et$_2$O (200 mL). Dry the combined organic phase over Na$_2$SO$_4$, filter, and concentrate. Purify the crude material by flash chromatograph, eluting with 5-10% ethylacetate/hexane to give 22.0 g (84%) of the title compound. GC m/z ($^{79}$Br$^{81}$Br) 266 [M]$^+$.

Preparation 112

(±)-3-(Methoxy-methyl-carbamoyl)-pyrrolidine-1-carboxylic acid tert-butyl ester

Add portionwise 1,1'-carbonyldiimidazole (4.14 g, 25.6 mmol) to a solution of pyrrolidine-1,3-dicarboxylic acid 1-tert-butyl ester (5.0 g, 23.2 mmol) in dichloromethane (77 mL) at RT. Allow the mixture to stir for 15 min. Add slowly N,O-dimethylhydroxylamine hydrochloride (2.7 g, 27.9 mmol). Stir the reaction mixture at RT overnight. Dilute the mixture with dichloromethane (200 mL), wash with water (2×300 mL), brine (200 mL), dry over Na$_2$SO$_4$, filter, and concentrate. Purify the crude material by flash chromatograph, eluting with 50-100% ethylacetate/hexane to give 5.36 g (89%) of the title compound. LC-MS/ES m/z 203.0 [M−tertBu+H]$^+$.

Preparation 113

3-(Methoxy-methyl-carbamoyl)-azetidine-1-carboxylic acid tert-butyl ester

Prepare the title compound by essentially following the procedures as described in Preparation 111, using azetidine-1,3-dicarboxylic acid mono-tert-butyl ester. GC-MS/ES m/z 244 [M+].

Preparation 114

(±)-3-(4-Bromo-benzoyl)-pyrrolidine-1-carboxylic acid tert-butyl ester

Add dropwise n-BuLi (9.6 mL, 15.4 mmol, 1.6 M in hexane) to a solution of 1,4-dibromo-phenyl (3.7 g, 15.4 mmol) in diethyl ether (140 mL) at −78° C. under nitrogen. Allow the mixture to stir at −78° C. for one hour. Add dropwise a solution of 3-(methoxy-methyl-carbamoyl)-pyrrolidine-1-carboxylic acid tert-butyl ester (3.97 g, 15.4 mmol) in diethyl ether (10 mL). Allow the reaction mixture to stir for one hour at −78° C. Warm the mixture to −10° C. and quench with saturated NH$_4$Cl solution (1 mL). Allow the mixture warm to RT, separate the organic layer, and concentrate. Purify the crude material by flash chromatograph, eluting with 15-25% ethylacetate/hexane to give 3.79 g (70%) of the title compound. LC-MS/ES m/z ($^{79}$Br) 298 [M−tertBu+H]$^+$.

Prepare the intermediates in the table below by essentially following the procedures as described in Preparation 114, using the corresponding dibromides and 3-(methoxy-methyl-carbamoyl)-azetidine-1-carboxylic acid tert-butyl ester or 3-(methoxy-methyl-carbamoyl)-pyrrolidine-1-carboxylic acid tert-butyl ester.

| Prep | Chemical Name | LC-MS/ES (m/z) |
|---|---|---|
| 115 | 3-(4-Bromo-benzoyl)-azetidine-1-carboxylic acid tert-butyl ester | ($^{81}$Br) 286 [M − tertBu + H]$^+$ |
| 116 | 3-(4-Bromo-2-methoxy-benzoyl)-azetidine-1-carboxylic acid tert-butyl ester | ($^{79}$Br) 314.0 [M − tertBu + H]$^+$ |
| 117 | (±)-3-(4-Bromo-2-methoxy-benzoyl)-pyrrolidine-1-carboxylic acid tert-butyl ester | ($^{81}$Br) 330 [M − tertBu + H]$^+$ |

Preparation 118

(±)-(4-Bromo-phenyl)-pyrrolidin-3-yl-methanone

Stir a solution of 3-(4-bromo-benzoyl)-pyrrolidine-1-carboxylic acid tert-butyl ester (3.79 g, 10.7 mmol) in 4 M HCl in dioxane (21.4 mL) at 0° C. for one hour. Concentrate the reaction mixture, dilute the mixture with CH$_2$Cl$_2$, wash with 5 N NaOH (15 mL), and back extract the aqueous with CH$_2$Cl$_2$. Wash the combined organic layer with brine, dry over Na$_2$SO$_4$, filter, and concentrate. Purify the crude material by flash chromatograph, eluting with 5-10% in MeOH (2N NH$_3$)/CH$_2$Cl$_2$ to give 2.24 g (82%) of the title compound. LC-MS m/z ($^{79}$Br) 254.0 [M+H]$^+$.

Preparation 119

Azetidin-3-yl-(4-bromo-phenyl)-methanone

Prepare the title compound by essentially following the procedures as described in Preparation 117, using 3-(4-bromo-benzoyl)-azetidine-1-carboxylic acid tert-butyl ester. LC-MS/ES m/z ($^{81}$Br) 242 [M+H]$^+$.

Preparation 120

(±)-(4-Bromo-phenyl)-(1-methyl-pyrrolidin-3-yl)-methanone

To a solution (4-bromo-phenyl)-pyrrolidin-3-yl-methanone (2.24 g, 8.81 mmol) in methanol (44 mL), add acetic acid (1.01 mL, 17.6 mmol) and formaldehyde (2.15 g, 26.4 mmol, 37% aqueous solution). After 15 min, add sodium triacetoxyborohydride (5.60 g, 26.4 mmol) and allow the mixture to stir at RT for one hour. Concentrate the reaction mixture. Add water and adjust the solution to pH=10 with 2 N NaOH. Extract the aqueous with ethylacetate. Dry the combined organic layers over Na$_2$SO$_4$, filter, and concentrate. Purify the crude material by flash chromatography, eluting with 5-10% MeOH (2N NH$_3$)/CH$_2$Cl$_2$ to give 1.61 g (68%) of the title compound. LC-MS/ES m/z ($^{79}$Br) 268.0 [M+H]$^+$.

Preparation 121

(4-Bromo-phenyl)-(1-methyl-azetidin-3-yl)-methanone

Prepare the title compound essentially by following the procedure for Preparation 119, using azetidin-3-yl-(4-bromo-phenyl)-methanone. LC-MS/ES m/z ($^{79}$Br) 254.0 [M+H]$^+$.

Preparation 122

(±)-[(4-Bromo-phenyl)-difluoro-methyl]-1-methyl-pyrrolidine

Add dropwise a solution of DAST (1.50 g, 9.32 mmol) in CH$_2$Cl$_2$ (5 mL) to a solution of (4-bromo-phenyl)-(1-methyl-pyrrolidin-3-yl)-methanone (0.5 g, 1.86 mmol) in CH$_2$Cl$_2$ (20 mL) at 0° C. Allow the mixture to warm RT, then heat at 40° C. for 48 h. Cool the mixture to RT and carefully quench with saturated NaHCO$_3$ (exothermic and gas evolution). Extract the mixture with CH$_2$Cl$_2$. Dry the combined organic layer over Na$_2$SO$_4$, filter, and concentrate. Purify the crude material by flash chromatography collecting all the fractions as the product does not show by UV. Elute with 3-5% MeOH (2N NH$_3$)/CH$_2$Cl$_2$ to give 0.081 g (15%) of the title compound. LC-MS/ES m/z ($^{81}$Br) 292.0 [M+H]$^+$.

Preparation 123

(±)-(4-Bromo-phenyl)-(1-methyl-pyrrolidin-3-yl)-methanol

Add sodium tetrahydroborate (0.36 g, 9.52 mmol) in portions to a solution of (4-bromo-phenyl)-(1-methyl-azetidin-3-yl)-methanone (0.64 g, 2.38 mmol) in CH$_2$Cl$_2$ at 0° C. Stir the mixture at RT overnight and quench with water. Adjust the aqueous to pH=10 by using 1 N NaOH and extract with ethylacetate (2×150 mL). Dry the combined organic layers over Na$_2$SO$_4$, filter, and concentrate. Purify the crude material by flash chromatography, collecting all the fractions as the product does not show by UV. Elute with 10% MeOH (2 N NH$_3$)/CH$_2$Cl$_2$ to give 0.22 g (34%) of the title compound. LC-MS/ES m/z ($^{79}$Br) 270.0 [M+H]$^+$.

Preparation 124

(±)-3-[(4-Bromo-phenyl)-fluoro-methyl]-1-methyl-pyrrolidine

Cool a solution of (4-bromo-phenyl)-(1-methyl-pyrrolidin-3-yl)-methanol in CH$_2$Cl$_2$ (6.5 mL) to 0° C. Add slowly a solution of DAST (0.1 mL, 0.78 mmol) in CH$_2$Cl$_2$. Stir the mixture at RT overnight. Cool the mixture to 0° C., then carefully quench with saturated NaHCO$_3$ (exothermic and gas evolution). Extract the aqueous layer with CH$_2$Cl$_2$. Dry the combined organic phases with Na$_2$SO$_4$, filter, and concentrate. Purify the crude material by flash chromatography, collecting all the fractions as the product does not show by UV. Elute with 5-10% MeOH (2 N NH$_3$)/CH$_2$Cl$_2$ to give 0.049 g (35%) of the title compound. LC-MS/ES m/z (79Br) 272.0 [M+H]$^+$.

Preparation 125

(±)-trans-3-(4-Bromo-2-methoxy-phenoxy)-4-hydroxy-pyrrolidine-1-carboxylic acid tert-butyl ester Suspend 4-bromoguaiacol (1.19 g, 5.72 mmol) and 6-oxa-3-aza-bicyclo[3.1.0]hexane-3-carboxylic acid tert-butyl ester (prepared according to Syn. Comm. V26, Is8, p 1499, 1996) (530 mg, 2.86 mmol) in ethanol (6 mL) and add cesium carbonate (2.33 g, 7.15 mmol) and 18-crown-6 (5 mg). Heat the reaction mixture at reflux temperature for four days. Filter the mixture and evaporate the filtrate. Purify by silica gel chromatography, eluting with 0-65% EtOAc in hexanes to give 760 mg (69%) of the title compound as a yellow solid. $^1$H NMR (DMSO-d$_6$): δ 7.13 (d, J=2.3 Hz, 1H), 7.04 (dd, J=8.8, 2.3 Hz, 1H), 6.97 (d, J=8.8 Hz, 1H), 5.42 (bs, 1H), 4.54 (m, 1H), 4.10 (m, 1H), 3.74 (s, 3H), 3.54 (td, J=12.6, 4.1, 1H), 3.40 (td, J=12.6, 4.1, 1H), 3.31 (m, 1H), 3.22 (m, 1H), 2.47 (m, 9H).

Preparation 126

(±)-trans-4-(4-Bromo-2-methoxy-phenoxy)-pyrrolidin-3-ol

Dissolve 3-(4-bromo-2-methoxy-phenoxy)-4-hydroxy-pyrrolidine-1-carboxylic acid tert-butyl ester (603 mg, 1.55 mmol) in dichloromethane (10 mL) and cool the mixture to 0° C. Add trifluoroacetic acid (2.0 mL, 26.45 mmol) and warm the mixture to room temperature for one hour. Remove the volatiles via reduced pressure and then apply to two 10 g SCX cartridges. Wash the material with methanol then elute the material with 2N ammonia in methanol to give 420 mg (93%) of the title compound as a clear oil. LC-MS/ES m/z ($^{81}$Br) 290.0 [M+H]$^+$.

Preparation 127

(±)-trans-4-(4-Bromo-2-methoxy-phenoxy)-1-methyl-pyrrolidin-3-ol

Dissolve 4-(4-bromo-2-methoxy-phenoxy)-pyrrolidin-3-ol (409 mg, 1.42 mmol) in dichloroethane (15 mL) and add formaldehyde (0.117 mL, 1.56 mmol, 37% aqueous solution), sodium triacetoxyborohydride (451 mg, 2.13 mmol), and acetic acid (0.325 mL, 5.68 mmol). Stir the mixture overnight. Dilute with saturated sodium bicarbonate and extract three times with dichloromethane. Combine all the organics and dry over sodium sulfate, filter, and evaporate the filtrate. Purify by silica gel chromatography, eluting with 0-6% MeOH in dichloromethane with 2 N ammonia to give 410 mg (95%) of the title compound as a clear oil. LC-MS/ES m/z ($^{81}$Br) 304.0 [M+H]$^-$.

Preparation 128

(±)-cis-3-(4-Bromo-2-methoxy-phenoxy)-4-fluoro-1-methyl-pyrrolidine

Add diethylaminosulfur trifluoride (0.173 mL, 1.31 mmol) to a solution of 4-(4-bromo-2-methoxy-phenoxy)-1-methyl-pyrrolidin-3-ol (0.329 g, 1.09 mmol) in dichloromethane (7 mL) at −78° C. Warm the mixture to room temperature and stir overnight. Evaporate the mixture and purify the resulting residue by silica gel chromatography, eluting with 0-70% ethyl acetate/hexane to give 130 mg (39%) of the title compound as a light brown oil. LC-MS/ES m/z ($^{81}$Br) 306.0 [M+H]$^+$.

Preparation 129

1-(4-Bromo-2-methoxy-phenyl)-piperazine

Dissolve 1-(2-methoxy-phenyl)-piperazine (5.0 g, 26.0 mmol) in dichloromethane 450 mL) and cool to 0° C. Add bromine (4.16 g, 26.0 mmol) slowly dropwise. After 2 h wash the reaction mixture with 1 N sodium hydroxide (250 mL). Separate the organic portion, dry (Na$_2$SO$_4$), filter and concentrate in vacuo to afford 7.0 g (99%) of the title compound. MS/ES m/z ($^{81}$Br) 273.0 [M+H]$^+$.

Preparation 130

1-(4-bromo-2-methoxy-phenyl)-4-methyl-piperazine

Dissolve 1-(4-bromo-2-methoxy-phenyl)-piperazine (7.0 g, 25.8 mmol) and acetic acid (5.9 mL, 103.2 mmol) in methanol (500 mL) and add aqueous formaldehyde (37%, 5.3 mL). After 5 min, add sodium cyanoborohydride (4.05 g, 64.5 mmol) and stir the mixture at room temperature overnight. Concentrate the reaction mixture in vacuo and partition between dichloromethane (200 mL) and 1 N sodium hydroxide (200 mL). Separate the organic portion and extract the aqueous portion with dichloromethane (2×100 mL). Dry the combined organics (Na$_2$SO$_4$), filter, and concentrate in vacuo to afford 7.1 g (96%) of the title compound. MS/ES m/z ($^{79}$Br) 285.0 [M+H]$^-$.

Preparation 131

3-(4-Bromo-phenoxy)-azetidine-1-carboxylic acid tert-butyl ester

Add dropwise potassium tert-butoxide in THF (34.6 mL, 34.6 mmol) to a solution of p-bromofluorobenzene (6.1 g, 34.6 mmol) in THF (144 mL) and 3-hydroxy-azetidine-1-carboxylic acid tert-butyl ester (5.0 g, 28.9 mmol) at RT. Heat the mixture at 70° C. overnight. Cool the mixture to RT, quench with water, dilute with Et$_2$O, and wash once with saturated NH$_4$Cl. Back extract the aqueous with Et$_2$O, dry the combined organics over Na$_2$SO$_4$, filter, and concentrate. Purify the crude material by flash chromatography, eluting with 25% EtOAc/hexane to give 4.4 g (46%) of the title compound. LC-MS/ES m/z ($^{81}$Br) 274 [M−tertBu+H]$^+$.

Preparation 132

N-(4-Bromo-phenyl)-2-pyrrolidin-1-yl-acetamide

Add potassium carbonate (2.1 g, 15.5 mmol) and pyrrolidine (9.65 mL, 116 mmol) to a solution of N-(4-bromophenyl)-2-chloroacetamide (2.0 g, 7.7 mmol) in acetonitrile (78 mL) at RT. Heat the mixture at 80° C. for 4 h. Cool the mixture to RT, dilute with CH$_2$Cl$_2$, and wash with brine and water. Dry the organic layer over Na$_2$SO$_4$, filter, and concentrate to give 2.17 g (99%) of the title compound. LC-ES/MS m/z ($^{79}$Br) 283.0 [M+H]$^+$.

Preparation 133

6-(4-Bromo-phenyl)-2-(4-chloro-phenyl)-6H-thieno[2,3-c]pyridin-7-one

Add pyridine (0.62 mL, 7.64 mmol) and triethylamine (0.53 mL, 3.82 mmol) to a mixture of 2-(4-chloro-phenyl)-6H-thieno[2,3-c]pyridin-7-one (0.5 g, 1.91 mmol), 4-bromobenzeneboronic acid (1.15 g, 5.73 mmol), cupric acetate (1.05 g, 5.73 mmol), and 4A molecular sieves (0.4 g) in dichloromethane (38 mL). Stir the mixture at RT for 2 days. Dilute the mixture with CH$_2$Cl$_2$, wash twice with a solution of 5% NH$_4$OH/H$_2$O, and H$_2$O. Dry the organics over Na$_2$SO$_4$, filter, wash with Et$_2$O, and concentrate. Purify the crude material by flash chromatography eluting with 10-15%

EtOAc/CH$_2$Cl$_2$ to give 0.2 g (25%) of the title compound. LC-ES/MS m/z ($^{81}$Br, $^{35}$Cl) 417.8 [M+H]$^+$.

Example 47

2-(4-Chloro-phenyl)-6-[4-(1-methyl-pyrrolidine-3-carbonyl)-phenyl]-6H-thieno[2,3-c]pyridin-7-one, hydrochloride

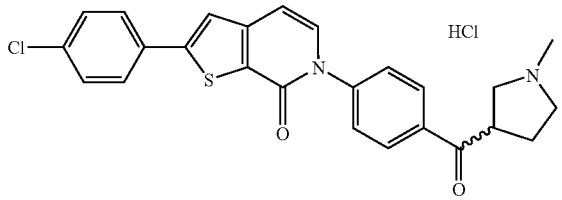

Combine 2-(4-chloro-phenyl)-6H-thieno[2,3-c]pyridin-7-one (0.15 g, 0.57 mmol), (4-bromo-phenyl)-(1-methyl-pyrrolidin-3-yl)-methanone (0.16 g, 0.60 mmol), Cs$_2$CO$_3$ (0.37 g, 1.15 mmol), 1,4-dioxane (6 mL), and CuI (0.044 g, 0.23 mmol). Purge the mixture with nitrogen for 10 min. Add sym-dimethylethylene diamine (0.040 g, 0.46 mmol). Heat the mixture at 100° C. overnight. Cool the mixture to RT, dilute with CH$_2$Cl$_2$ (200 mL), and wash with a solution of 5% NH$_4$OH/H$_2$O (2×30 mL). Dry the organic layer over Na$_2$SO$_4$, filter, and concentrate. Filter the crude with H$_2$O (200 mL) and Et$_2$O (100 mL). Prepare the HCl salt by dissolving the solid in CH$_2$Cl$_2$ and adding 1 eq 1M HCl/ether. Allow the solution to stir for 15 min and concentrate to give 0.21 g (77%) of the title compound. LC-MS/ES m/z ($^{35}$Cl) 449.0 [M+H]$^+$.

Prepare the examples and intermediates in the table below, by essentially following the same procedure as described in Example 47 by coupling the appropriate 5,6-dihydro-4H-thieno[2,3-c]pyridine-7-one or 6H-thieno[2,3-c]pyridin-7-one with the corresponding aryl bromide. Prepare the corresponding HCl salts where indicated.

| Ex or Prep | Chemical Name | LC-MS/ES (m/z) |
|---|---|---|
| 48 | 2-(4-Chloro-phenyl)-6-[4-(1-methyl-azetidine-3-carbonyl)-phenyl]-6H-thieno[2,3-c]pyridin-7-one, hydrochloride | ($^{35}$Cl) 435.0 [M + H]$^+$ |
| 49 | (±)-2-(4-Chloro-phenyl)-6-[4-(1-methyl-pyrrolidine-3-carbonyl)-phenyl]-5,6-dihydro-4H-thieno[2,3-c]pyridin-7-one, hydrochloride | ($^{35}$Cl) 451.0 [M + H]$^+$ |
| 50 | 2-(4-Chloro-phenyl)-6-[4-(1-methyl-azetidine-3-carbonyl)-phenyl]-5,6-dihydro-4H-thieno[2,3-c]pyridin-7-one, hydrochloride | ($^{35}$Cl) 437.0 [M + H]$^+$ |
| 51 | (±)-2-(4-Chloro-phenyl)-6-{4-[difluoro-(1-methyl-pyrrolidin-3-yl)-methyl]-phenyl}-6H-thieno[2,3-c]pyridin-7-one | ($^{35}$Cl) 471.0 [M + H]$^+$ |
| 52 | (±)-2-(4-Chloro-phenyl)-6-{4-[hydroxy-(1-methyl-pyrrolidin-3-yl)-methyl]-phenyl}-6H-thieno[2,3-c]pyridin-7-one | ($^{35}$Cl) 451.2 [M + H]$^+$ |
| 53 | (±)-2-(4-Chloro-phenyl)-6-{4-[hydroxy-(1-methyl-pyrrolidin-3-yl)-methyl]-phenyl}-5,6-dihydro-4H-thieno[2,3-c]pyridin-7-one | ($^{35}$Cl) 453.0 [M + H]$^+$ |
| 54 | (±)-2-(4-Chloro-phenyl)-6-{4-[fluoro-(1-methyl-pyrrolidin-3-yl)-methyl]-phenyl}-6H-thieno[2,3-c]pyridin-7-one | ($^{35}$Cl) 453.2 [M + H]$^+$ |
| 55* | (±)-trans-2-(4-Chloro-phenyl)-6-[4-(4-hydroxy-1-methyl-pyrrolidin-3-yloxy)-3-methoxy-phenyl]-6H-thieno[2,3-c]pyridin-7-one, hydrochloride | ($^{35}$Cl) 483.0 [M + H]$^+$ |
| 56 | (±)-cis-2-(4-Chloro-phenyl)-6-[4-(4-fluoro-1-methyl-pyrrolidin-3-yloxy)-3-methoxy-phenyl]-6H-thieno[2,3-c]pyridin-7-one | ($^{35}$Cl) 485.0 [M + H]$^+$ |
| 57 | 2-(4-Chloro-phenyl)-6-[3-methoxy-4-(4-methyl-piperazin-1-yl)-phenyl]-5,6-dihydro-4H-thieno[2,3-c]pyridin-7-one hydrochloride | ($^{35}$Cl) 468.0 [M + H]$^+$ |
| 58 | N-{4-[2-(4-Chloro-phenyl)-7-oxo-7H-thieno[2,3-c]pyridin-6-yl]-phenyl}-2-pyrrolidin-1-yl-acetamide, hydrochloride | ($^{35}$Cl) 464.0 [M + H]$^+$ |
| Prep 134 | 3-{4-[2-(4-Chloro-phenyl)-7-oxo-7H-thieno[2,3-c]pyridin-6-yl]-2-methoxy-benzoyl}-azetidine-1-carboxylic acid tert-butyl ester | ($^{35}$Cl) 495.0 [M − tert Bu + H]$^+$ |
| Prep 135 | 3-{4-[2-(4-Fluoro-phenyl)-7-oxo-7H-thieno[2,3-c]pyridin-6-yl]-2-methoxy-benzoyl}-azetidine-1-carboxylic acid tert-butyl ester | 479.0 [M − tert Bu + H]$^+$ |
| Prep 136 | (±)-3-{4-[2-(4-Chloro-phenyl)-7-oxo-7H-thieno[2,3-c]pyridin-6-yl]-2-methoxy-benzoyl}-pyrrolidine-1-carboxylic acid tert-butyl ester | ($^{35}$Cl) 509.0 [M − tertBu + H]$^+$ |
| Prep 137 | (±)-trans-3-{4-[2-(4-Chloro-phenyl)-7-oxo-7H-thieno[2,3-c]pyridin-6-yl]-2-methoxy-phenoxy}-4-hydroxy-pyrrolidine-1-carboxylic acid tert-butyl ester | ($^{35}$Cl) 513.0 [M − tertBu + H]$^+$ |
| Prep 138 | 3-{4-[2-(4-Fluoro-phenyl)-7-oxo-7H-thieno[2,3-c]pyridin-6-yl]-phenoxy}-azetidine-1-carboxylic acid tert-butyl ester | 437.0 [M − tert Bu + H]$^+$ |

*Prepare the hydrochloride salt by adding 1 equivalent of ammonium chloride in methanol and dichloromethane.

Preparation 139

(±)-3-{4-[2-(4-Chloro-phenyl)-7-oxo-7H-thieno[2,3-c]pyridin-6-yl]-phenylcarbamoyl}-pyrrolidine-1-carboxylic acid tert-butyl ester Combine 3-carbamoyl-pyrrolidine-1-carboxylic acid tert-butyl ester (0.21 g, 0.96 mmol), 6-(4-bromo-phenyl)-2-(4-chloro-phenyl)-6H-thieno[2,3-c]pyridin-7-one (0.2 g, 0.48 mmol), $Cs_2CO_3$ (0.31 g, 0.96 mmol), 1,4-dioxane (5 mL), and CuI (0.037 g, 0.19 mmol). Purge the mixture with nitrogen for 10 min and then add sym-dimethylethylene diamine (0.034 g, 0.38 mmol). Heat the mixture at 100° C. overnight. Cool the mixture to RT, dilute with $CH_2Cl_2$, and wash twice with a solution of 5% $NH_4OH/H_2O$. Dry the organic layer over $Na_2SO_4$, filter, and concentrate. Filter the crude with $Et_2O$ and water to give 0.117 g (43%) of the title compound. LC-ES/MS m/z ($^{35}Cl$) 494.0 [M−tert Bu+H]$^+$.

Preparation 140

(±)-2-(4-Chloro-phenyl)-6-[3-methoxy-4-(pyrrolidine-3-carbonyl)-phenyl]-6H-thieno[2,3-c]pyridin-7-one, trifluoro-acetic acid

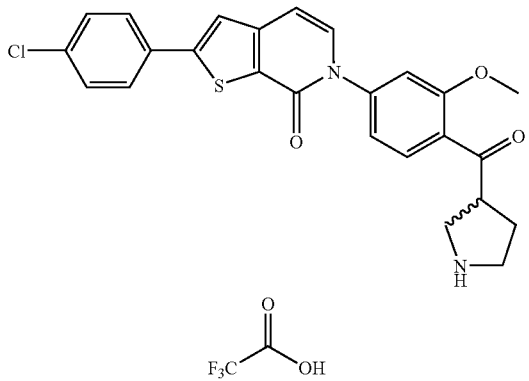

Add trifluoroacetic acid (8.58 mL, 113.5 mmol) to a solution of 3-{4-[2-(4-chloro-phenyl)-7-oxo-7H-thieno[2,3-c]pyridin-6-yl]-2-methoxy-benzoyl}-pyrrolidine-1-carboxylic acid tert-butyl ester (0.97 g, 1.72 mmol) in $CH_2Cl_2$ (17 mL). Stir the mixture at RT for 2 hrs, concentrate to give 1.37 g of the crude. LC-MS/ES m/z ($^{35}Cl$) 465 [M+H]$^+$.

Prepare the compounds in the table below by essentially following the procedure as described in Preparation 140, using the corresponding protected amines.

| Prep | Chemical Name | LC-MS (m/z) |
| --- | --- | --- |
| 141 | 6-[4-(Azetidine-3-carbonyl)-3-methoxy-phenyl]-2-(4-chloro-phenyl)-6H-thieno[2,3-c]pyridin-7-one, trifluoroacetic acid | ($^{35}Cl$) 451.0 [M + H]$^+$ |
| 142 | 6-[4-(Azetidine-3-carbonyl)-3-methoxy-phenyl]-2-(4-fluoro-phenyl)-6H-thieno[2,3-c]pyridin-7-one, trifluoroacetic acid | 435.0 [M + H]$^+$ |
| 143* | 6-[4-(Azetidin-3-yloxy)-phenyl]-2-(4-fluoro-phenyl)-6H-thieno[2,3-c]pyridin-7-one | 393.0 [M + H]$^+$ |

*Dilute the crude residue with $CH_2Cl_2$ then wash with NaOH and water. Dry the solution and evaporate.

Preparation 144

(±)-Pyrrolidine-3-carboxylic acid {4-[2-(4-chloro-phenyl)-7-oxo-7H-thieno[2,3-c]pyridin-6-yl]-phenyl}-amide Add trifluoroacetic (1.06 mL, 14.1 mmol) to a solution of 3-{4-[2-(4-chloro-phenyl)-7-oxo-7H-thieno[2,3-c]pyridin-6-yl]-phenylcarbamoyl}-pyrrolidine-1-carboxylic acid tert-butyl ester (0.12 g, 0.21 mmol) in $CH_2Cl_2$ (2 mL). Stir the mixture at RT for 2 h, and concentrate in vacuo. Dissolve the crude residue in $CH_2Cl_2$, filter through an SCX column with $CH_2Cl_2$ and MeOH, then elute the product with 2 N $NH_3$ in MeOH. Concentrate the solution, then filter the solid with $Et_2O$ to give 0.84 g (88%) of the title compound. LC-ES/MS m/z ($^{35}Cl$) 450.0 [M+H]$^+$.

Example 59

(±)-trans-2-(4-Chloro-phenyl)-6-[4-(4-hydroxy-pyrrolidin-3-yloxy)-3-methoxy-phenyl]-6H-thieno[2,3-c]pyridin-7-one, hydrochloride Dissolve 3-{4-[2-(4-chloro-phenyl)-7-oxo-7H-thieno[2,3-c]pyridin-6-yl]-2-methoxy-phenoxy}-4-hydroxy-pyrrolidine-1-carboxylic acid tert-butyl ester (0.97 g, 1.70 mmol) in dichloromethane (15 mL) and cool the mixture to 0° C. Add trifluoroacetic acid (3 mL). Stir for one hour at 0° C. and one hour at room temperature. Evaporate the mixture and apply the resulting residue to 3×10 g SCX cartridges. Wash the material with methanol then elute with 2 N ammonia in methanol to give a yellow solid (0.54 g, 67%). Dissolve the residue (27 mg, 0.057 mmol) in methanol (2 mL) and add ammonium chloride (3.05 mg, 0.057 mmol). Sonicate the mixture for 5 min then evaporate to give 0.029 g (100%) of a yellow product. LC-MS/ES m/z ($^{35}Cl$) 469 [M+H]$^+$.

Example 60

(±)-2-(4-Chloro-phenyl)-6-[3-methoxy-4-(1-methyl-pyrrolidine-3-carbonyl)-phenyl]-6H-thieno[2,3-c]pyridin-7-one, hydrochloride

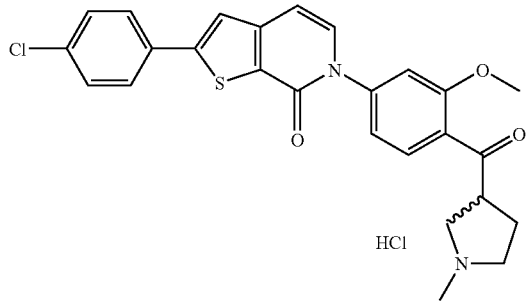

Add acetic acid (1.50 g, 2.48 mmol) and formaldehyde (0.20 g, 2.48 mmol, 37% aqueous solution) to a solution of 2-(4-chloro-phenyl)-6-[3-methoxy-4-(pyrrolidine-3-carbonyl)-phenyl]-6H-thieno[2,3-c]pyridin-7-one, trifluoro-acetic acid (0.36 g, 0.62 mmol) in methanol (31 mL). Stir the mixture at RT for 15 min, then add sodium triacetoxyborohydride (0.55 g, 2.48 mmol), and continue to stir the mixture at RT for 2 h. Dilute the mixture with $CH_2Cl_2$ (200 mL), wash with saturated $NaHCO_3$, and back extract the aqueous with $CH_2Cl_2$ (100 mL). Wash the combined organic phases with water (100 mL), dry over $Na_2SO_4$, filter, and concentrate. Purify the crude material by filtering with $Et_2O$ (100 mL) and water (50 mL). To prepare the HCl salt dissolve the solid in $CH_2Cl_2$, and add 1 eq 1M HCl/ether. Allow the solution to stir for 15 min, and concentrate to give 0.16 g (50%) of the title compound. LC-MS/ES m/z ($^{35}$Cl) 479.0 [M+H]$^+$.

Prepare the compounds in the table below by essentially following the procedure as described in Example 60 with the exception that 4A molecular sieves were added to the mixture. Use the appropriate amine with formaldehyde or cyclobutanone.

| Ex | Chemical Name | LC-MS/ES (m/z) |
|---|---|---|
| 61 | 2-(4-Chloro-phenyl)-6-[3-methoxy-4-(1-methyl-azetidine-3-carbonyl)-phenyl]-6H-thieno[2,3-c]pyridin-7-one, hydrochloride | ($^{35}$Cl) 465.0 [M + H]$^+$ |
| 62 | 2-(4-Chloro-phenyl)-6-[4-(1-cyclobutyl-azetidine-3-carbonyl)-3-methoxy-phenyl]-6H-thieno[2,3-c]pyridin-7-one, hydrochloride | ($^{35}$Cl) 505.0 [M + H]$^+$ |
| 63 | 2-(4-Fluoro-phenyl)-6-[3-methoxy-4-(1-methyl-azetidine-3-carbonyl)-phenyl]-6H-thieno[2,3-c]pyridin-7-one, hydrochloride | 449.0 [M + H]+ |
| 64 | (±)-2-(4-Chloro-phenyl)-6-[4-(1-cyclobutyl-pyrrolidine-3-carbonyl)-3-methoxy-phenyl]-6H-thieno[2,3-c]pyridin-7-one, hydrochloride | ($^{35}$Cl) 519.0 [M + H]$^+$ |
| 65 | 2-(4-Fluoro-phenyl)-6-[4-(1-methyl-azetidin-3-yloxy)-phenyl]-6H-thieno[2,3-c]pyridin-7-one, hydrochloride | 407.0 [M + H]$^+$ |
| 66 | (±)-1-Methyl-pyrrolidine-3-carboxylic acid {4-[2-(4-chloro-phenyl)-7-oxo-7H-thieno[2,3-c]pyridin-6-yl]-phenyl}-amide, hydrochloride | ($^{35}$Cl) 464.0 [M + H]$^+$ |

Example 67 trans-2-(4-Chloro-phenyl)-6-[4-(4-hydroxy-1-methyl-pyrrolidin-3-yloxy)-3-methoxy-phenyl]-6H-thieno[2,3-c]pyridin-7-one, hydrochloride, Isomer 1 and

Example 68 trans-2-(4-Chloro-phenyl)-6-[4-(4-hydroxy-1-methyl-pyrrolidin-3-yloxy)-3-methoxy-phenyl]-6H-thieno[2,3-c]pyridin-7-one, hydrochloride, Isomer 2

Purify the enantiomers of (±)-2-(4-chloro-phenyl)-6-[4-(4-hydroxy-1-methyl-pyrrolidin-3-yloxy)-3-methoxy-phenyl]-6H-thieno[2,3-c]pyridin-7-one using a 4.6×150 mm Chiralcel® OJ-H column eluting with 100% methanol with 0.2% dimethylethylamine to give two trans isomers. Isomer 1: $T_R$=9.3 min; Isomer 2: $T_R$=14.0 min.

Dissolve each isomer in methanol (3 mL) and add ammonium chloride then evaporate the mixture to give the title compounds as white solids. Isomer 1: LC-MS/ES m/z ($^{35}$Cl) 483.0 [M+H]$^+$; Isomer 2: LC-MS/ES m/z ($^{35}$Cl) 483.0 [M+H]$^+$.

We claim:

1. The compound N-{4-[2-(4-Chloro-phenyl)-7-oxo-4,7-dihydro-5H-thieno[2,3-c]pyridin-6-yl]-2-methoxy-phenyl}-2-pyrrolidin-1-yl-acetamide, hydrochloride salt

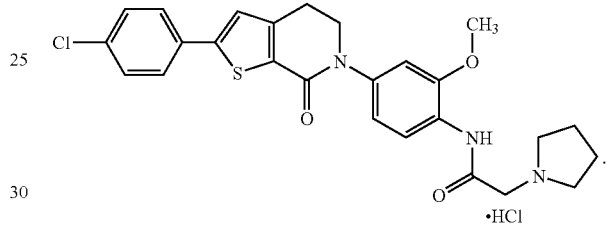

2. A pharmaceutical composition comprising a compound according to claim 1, or a pharmaceutically acceptable salt thereof, and a pharmaceutically acceptable carrier and/or diluent.

* * * * *